(12) United States Patent
Beraja et al.

(10) Patent No.: US 8,165,897 B2
(45) Date of Patent: *Apr. 24, 2012

(54) MEDICAL DECISION SYSTEM INCLUDING INTERACTIVE PROTOCOLS AND ASSOCIATED METHODS

(76) Inventors: Roberto Beraja, Coral Gables, FL (US);
Victor Beraja, Coral Gables, FL (US);
Esther Beraja, Coral Gables, FL (US);
Isidoro Beraja, Coral Gables, FL (US);
Matilde Beraja, Coral Gables, FL (US)

( * ) Notice: Subject to any disclaimer, the term of this patent is extended or adjusted under 35 U.S.C. 154(b) by 6 days.

This patent is subject to a terminal disclaimer.

(21) Appl. No.: 12/614,910

(22) Filed: Nov. 9, 2009

(65) Prior Publication Data

US 2011/0112849 A1    May 12, 2011

(51) Int. Cl.
*G06Q 10/00* (2012.01)
*G06Q 50/00* (2012.01)
*A61B 5/00* (2006.01)
*G06F 19/00* (2011.01)

(52) U.S. Cl. .............................................. 705/2; 705/3
(58) Field of Classification Search .................. 705/2–3
See application file for complete search history.

(56) References Cited

U.S. PATENT DOCUMENTS

| | | | |
|---|---|---|---|
| 5,583,758 A * | 12/1996 | McIlroy et al. | 705/2 |
| 5,924,073 A | 7/1999 | Tyuluman et al. | |
| 5,924,074 A | 7/1999 | Evans | |
| 5,946,659 A | 8/1999 | Lancelot et al. | |
| 6,047,259 A * | 4/2000 | Campbell et al. | 705/3 |
| 618,988 A1 | 2/2001 | Barry et al. | |
| 6,283,761 B1 | 9/2001 | Joao | |
| 6,484,144 B2 | 11/2002 | Martin et al. | |
| 6,341,265 B1 | 1/2004 | Provost et al. | |
| 6,684,276 B2 * | 1/2004 | Walker et al. | |
| 6,827,670 B1 * | 12/2004 | Stark et al. | |
| 6,988,088 B1 * | 1/2006 | Miikkulainen et al. | |
| 7,256,708 B2 * | 8/2007 | Rosenfeld et al. | |
| 2001/0012913 A1 * | 8/2001 | Iliff | |
| 2002/0019749 A1 * | 2/2002 | Becker et al. | |

(Continued)

OTHER PUBLICATIONS

Medical Expert Systems, May 20, 2005. http://www.computer.privateweb.at/judith/name_3.htm.

*Primary Examiner* — Robert Morgan
*Assistant Examiner* — Joy Chng
(74) *Attorney, Agent, or Firm* — Mark R. Malek, Esq.; G. Philip J. Zies, Esq.; Zies Widerman & Malek

(57) ABSTRACT

An interactive protocol system for a medical decision system includes a plurality of medical related information databases containing medical related information and rules, a patient information database including patient information, a medical practices database including information relating to medical practices, a questions database including questions to be presented to a user relating to medical care, and an answers database including answers related to the respective questions in said questions database. The medical practices database may include a plurality of protocols. Each of the plurality of protocols may include a different plurality of narrowing questions to be presented to the user. The questions may relate to at least one of the plurality of protocols and may be presented to the user based on the answers to the questions provided by the user. The narrowing questions in at least one of the plurality of protocols may be answered by the user to provide the user an indication relating to medical practices.

29 Claims, 27 Drawing Sheets

U.S. PATENT DOCUMENTS

| | | |
|---|---|---|
| 2002/0087358 A1* | 7/2002 | Gilbert |
| 2002/0120471 A1* | 8/2002 | Drazen |
| 2002/0143579 A1* | 10/2002 | Docherty et al. |
| 2002/0143582 A1 | 10/2002 | Neuman et al. |
| 2003/0055679 A1 | 3/2003 | Soll et al. |
| 2003/0120512 A1 | 6/2003 | Dengler |
| 2003/0158755 A1 | 8/2003 | Neuman |
| 2003/0212576 A1 | 11/2003 | Kim |
| 2003/0233250 A1 | 12/2003 | Joffee et al. |
| 2004/0015337 A1 | 1/2004 | Thomas et al. |
| 2004/0078220 A1 | 4/2004 | Jackson |
| 2004/0078231 A1* | 4/2004 | Wilkes et al. ............ 705/2 |
| 2004/0153338 A1 | 8/2004 | Kim et al. |
| 2004/0260577 A1 | 12/2004 | Dahlin et al. |
| 2004/0260666 A1* | 12/2004 | Pestotnik et al. ............ 706/46 |
| 2004/0267572 A1 | 12/2004 | Emery et al. |
| 2006/0036619 A1* | 2/2006 | Fuerst et al. ............ 707/100 |

\* cited by examiner

MEDICAL DECISION SYSTEM INCLUDING INTERACTIVE PROTOCOLS AND ASSOCIATED METHODS

RELATED APPLICATIONS

This application is a continuation-in-part of U.S. patent application Ser. No. 11/928,690 filed on Oct. 30, 2007 and titled Medical Professional Monitoring System and Associated Methods, which was a divisional application of U.S. patent application Ser. No. 11/191,304 filed on Jul. 28, 2005 and titled Medical Professional Monitoring System and Associated Methods, and is related to U.S. patent application Ser. No. 12/614,841 filed simultaneously herewith and titled Medical Decision System Including Question Mapping and Cross Referencing System and Associated Methods and U.S. patent application Ser. No. 12/614,937 filed simultaneously herewith and titled Medical Decision System Including Medical Observation Locking and Associated Methods, the entire contents of each of which are incorporated herein by reference.

FIELD OF THE INVENTION

The present invention relates to the field of systems for making medical decisions and, more particularly, to the field of systems for making medical decisions including interactive protocols to provide an indication relating to medical practices, and related methods.

BACKGROUND OF THE INVENTION

Systems and various types of software have been extensively used to assist medical professionals in making diagnoses of patient conditions, and to assist medical professionals in prescribing particular courses of medical treatments for those diagnoses.

For example, a medical software system provided under the trade name "ACORN" is a system that was developed by the Accident & Emergency Department of Westminster Hospital in London that advises on management of chest pain patients in the emergency room. Another medical software system is provided under the trade name "ADE Monitor" and is being developed by the Washington University School of Medicine Department of Internal Medicine division of Medical Informatics. This system was developed to monitor patient clinical data for potential adverse drug events. Yet another similar medical software system is offered under the trade name "CADIAG-II" and has been developed by the Department of Medical Computer Sciences, University of Vienna, the Department of Internal Medicine III, section of Rheumatology and the Department of Internal Medicine I, Divisions of Oncology, University of Vienna Medical School. This system is directed to colon diseases, and is a computer-assisted consultation system to support the differential diagnostic process in internal medicine.

U.S. Published Patent Application No. 2002/0120471 by Drazen discloses a system that includes a database for storing a plurality of different medical guidelines for different health conditions, and for storing historical patient information data for a plurality of patients. The patient information is gathered over a global communications network, i.e., the Internet, and evaluated to provide a patient specific risk report based upon the medical guidelines stored in the database. A physician's treatment plan may be generated to reduce patient risk based on the medical guidelines.

This system, however, may be disadvantageous as it allows a physician to become reliant upon a system, instead of the physician's own medical knowledge. Further, this system fails to monitor performance of the physician with respect to whether the medical treatment prescribed by the physician is proper. Accordingly, such a system may cause a waste in resources.

U.S. Published Patent Application No. 2002/0143579 by Docherty et al. discloses a system that identifies opportunities for direct physician intervention to improve prescribing practices and patient compliance. More specifically, the system collects information relating to a physician's prescription practice, and analyzes that information with respect to expert guidelines. The system identifies deviations from expert guidelines and provides the physician with intervention information.

A system for assessing physician performance that includes a database to store patient/physician contact is disclosed in U.S. Pat. No. 5,924,073 to Tyuluman et al. An evaluator is coupled to the database to evaluate the data using statistical analysis. This system may be used to define a standard of care for a core element of patient population. The standard of care may be updated based upon more efficient and more effective treatments, and the system may identify doctors who perform outside the defined standard of care. These systems, however, do not take into account the several standards that a physician must analyze when prescribing medical treatments, i.e., hospital standards, medical standards, insurance standards, etc.

U.S. Published Patent Application No. 2003/0055679 by Soil et al. discloses a computerized patient management system that includes a patient module, a physician module, and a database. The system allows patients to input their patient information into the patient module. The database includes medical assessment and treatment information used to analyze the patient information and generate a report. The physician may edit the report and add assessment and management plans. The physician may also select patient educational materials to be provided to the patient, along with a health summary, at a patient interview. This system, however, relies heavily on the patients' ability to properly enter their patient information. Further, this system provides access to persons that do not have as much medical knowledge as a trained medical professional.

U.S. Pat. No. 5,924,074 to Evans is directed to a medical records system that creates and maintains patient data electronically. The system includes a graphical user interface that has touch screens. The system captures patient data, such as patient complaints, lab orders, medications, diagnoses, and procedures. A medical professional may use a pen based portable computer with wireless connection to a computer networked to access, analyze, update and electronically annotate patient data. In short, the Evans '074 patent eliminates the need to create and maintain physical data record.

U.S. Pat. No. 6,283,761 to Joao discloses a system that includes a central processing unit for processing symptom information and condition information corresponding to a patient, in conjunction with healthcare information, healthcare theories, healthcare principals, and healthcare research. The processor generates a diagnostic report of the patient that contains a possible diagnosis. The Joao '761 patent discloses providing access to healthcare providers, patients, and insurance companies so that proper updates of patient information may be made. The system may be used to allow a medical professional to ascertain a medical diagnosis, verify diagnosis or treatment, or allow a patient to perform a self diagnosis. The Joao '761 patent also discloses a system for providing training and continuing education services to medical providers that is delivered electronically.

Another issue that has arisen with the above systems is that there may be a need to enter duplicative information. Medical professionals generally follow various protocols depending on a presumed diagnosis. Within various protocols, there may exist requirements to enter duplicative information depending on various medical observations. For example, a medical professional may make an initial observation, and associated diagnosis, but then change the diagnosis. When entering a new protocol, however, it may be necessary for the medical professional to re-enter medical/observatory information that is duplicative. Of course, such duplicative activity is a strain on the tight schedules of medical professionals. Further, when making a change from one diagnosis to another, or when additional medical observations are made, additional medical protocols may not be available to the medical professional for ready viewing, i.e., the medical professional may need to retrieve the new protocol from another database. Again, this may be disadvantageous to the medical professional as it constrains the medical professional's time.

SUMMARY OF THE INVENTION

With the foregoing in mind, it is therefore an object of the present invention to provide an interactive protocol system and method that allows a user to access various medical protocols. It is also an object of the present invention to provide an interactive protocol system that allows a medical professional to readily obtain an indication relating to medical practices that reduces errors. It is further an object of the present invention to provide an interactive protocol system that is efficient and eliminates the duplicate entries.

These and other objects, features and advantages according to the present invention are provided by an interactive protocol system including a plurality of medical related databases containing medical related information and rules governing medical care. The interactive protocol system may also include a patient information database including patient information and a medical practices database including information relating to medical practices.

The interactive protocol system may further include a questions database including questions to be presented to a user relating to medical care, and an answers database including answers related to the respective questions in the questions database. The plurality of medical related information databases, the patient information database, the medical practices database, the questions database and the answers database are preferably stored on a computer readable medium or a computer memory. The databases are accessible by a user using a user interface.

The medical practices database also preferably includes a plurality of protocols. Each of the plurality of protocols includes a different plurality of narrowing questions to be presented to the user. The questions relating to the plurality of protocols are preferably presented to the user based on the answers to the questions provided by the user. The narrowing questions in each of the plurality of protocols are to be answered by the user to provide the user an indication related to medical practices. The indication relating to medical practices may be a diagnosis selected from a plurality of diagnoses stored on one of the plurality of medical related information databases.

The plurality of medical related information databases may include medical analysis information used to make a medical related decision. The medical related decision may include a prescribed medication, a medical test, a medical procedure recommendation, a medical treatment recommendation, and an indication relating to insurance reimbursement. The indication relating to medical practices may provide the user information necessary to make the medical related decision. The indication may be a medical related decision selected from a plurality of medical related decisions stored on one of the medical related information databases. The medical related decision may be based on a comparison of the rules stored on one of the plurality of medical related information databases with the answers to the questions.

The selected medical related decision may represent one of a plurality of best practices. A best practice may be defined as a best available medical related decision as determined by at least one medical professional peer. The best practices may be updated on the plurality of medical related information databases. More specifically, the plurality of medical related information databases may be automatically updated with the best practices.

A user may enter patient information into the patient information database responsive to a prompted indication using the user interface. The interactive protocol system of the present invention preferably includes a duplication prevention system to prevent presentation of a prompted indication requiring entry of patient information that is currently stored in the patient information database. Information entered by the user using the user interface may include medical history information, medication information and insurance information. The information entered by the user may be entered into the medical related information databases and the patient information database.

A method aspect of the present invention is for making a medical related decision using an interactive protocol system. The method may include presenting the user with a question relating to medical care that is stored on a questions database. The method may also include prompting the user for an answer relating to the question. The method may further include determining at least one of the plurality of protocols to be presented to the user based on the answers to the questions, and presenting the user with additional narrowing questions relating to the at least one protocol from the questions database to be answered. The method may still further include providing the user an indication relating to medical practices based on the respective answers to the narrowing questions.

Another method aspect of the present invention is also directed to making a medical decision and includes presenting the user with a question relating to medical care, and prompting the user for an answer relating to the question. The method may also include determining at least one of the plurality of protocols to be presented to the user based on the answers to the questions, and presenting the user with additional narrowing questions relating to the at least one protocol from the questions database to be answered. The method may further include entering patient information into a patient information database using the user interface responsive to a prompted indication and preventing presentation of a prompted indication requiring entry of patient information that is currently stored in the patient information database.

DETAILED DESCRIPTION OF THE PREFERRED EMBODIMENTS

The present invention will now be described more fully hereinafter with reference to the accompanying drawings, in which preferred embodiments of the invention are shown. This invention may, however, be embodied in many different forms and should not be construed as limited to the embodiments set forth herein. Rather, these embodiments are provided so that this disclosure will be thorough and complete, and will fully convey the scope of the invention to those skilled in the art. Like numbers refer to like elements throughout.

The system according to the present invention is a computerized system that requires the performance of one or more steps to be performed on or in association with a computerized device, such as, but not limited to, a server, a computer (i.e., desktop computer, laptop computer, netbook or a machine having a processor), a dumb terminal that provides an interface with a computer or server, a personal digital assistant, mobile communications device, such as an iPhone, Blackberry or other similar device which provides computer or quasi-computer functionality, a mobile reader, such as a Kindle, which provides reader functionality that may be enabled through either internal components or connecting to an external computer, server or global communications network (such as the Internet) to take direction from or engage in processes which are then delivered to the mobile reader. It should be readily apparent to those of skill in the art that other types of devices, individually or in conjunction with an over-arching architecture associated with an internal or external system, may be utilized to provide the "computerized" environment necessary for the at least one process step to be carried out in a machine/system/digital environment. It should be noted that the method aspects of the present invention are preferably computer implemented methods and, more particularly, at least one step is preferably carried out using a computerized device. In short, a computerized system according to the present invention is meant to include any device having a processor and a memory.

Figure 1:
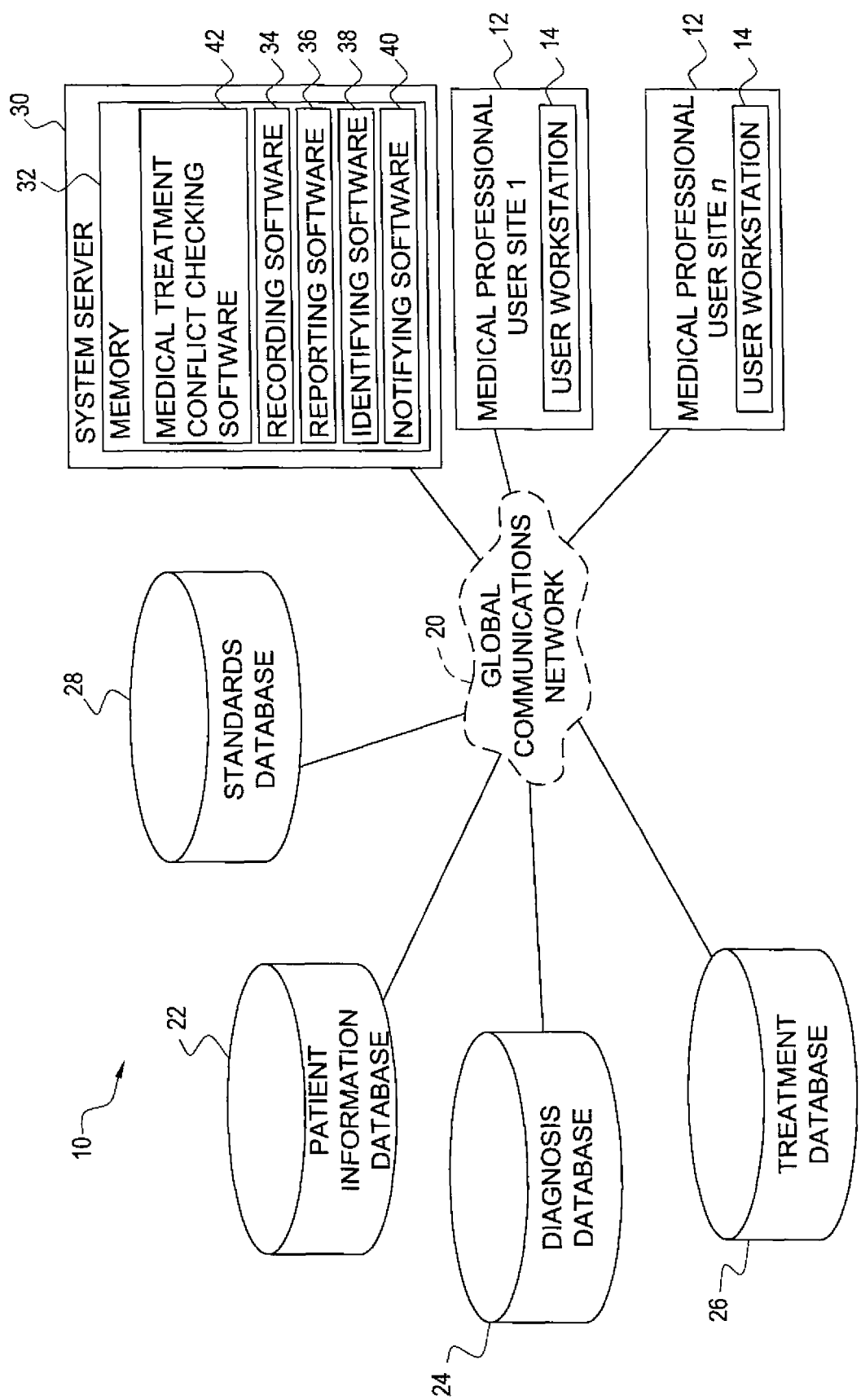
FIG. 1 is a schematic view of a medical professional monitoring system according to the present invention and being accessed by various medical professional user sites.
Figure 2:
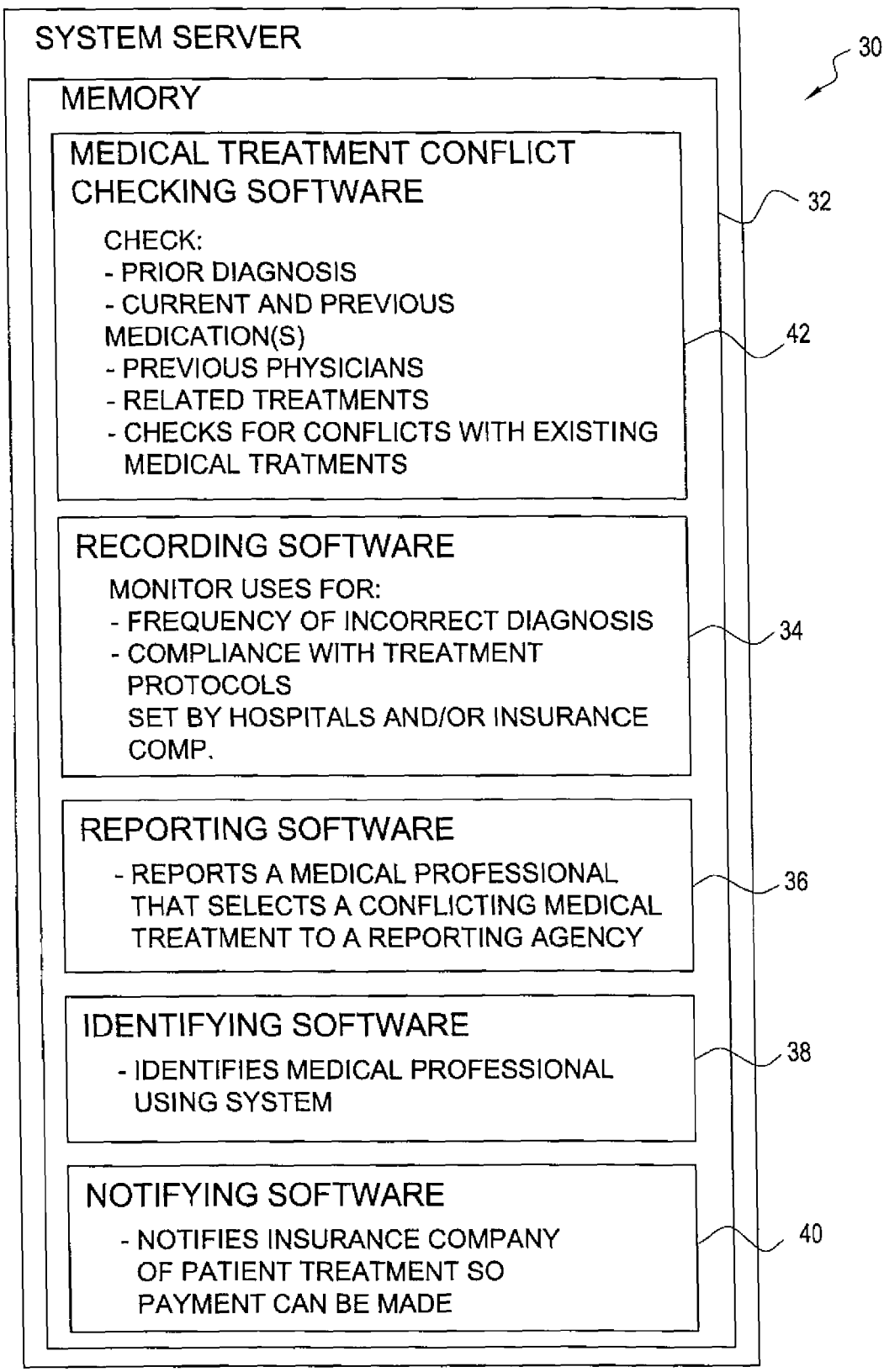
FIG. 2 is a schematic view of the server of the medical professional monitoring system illustrated in FIG. 1.
Figure 3:
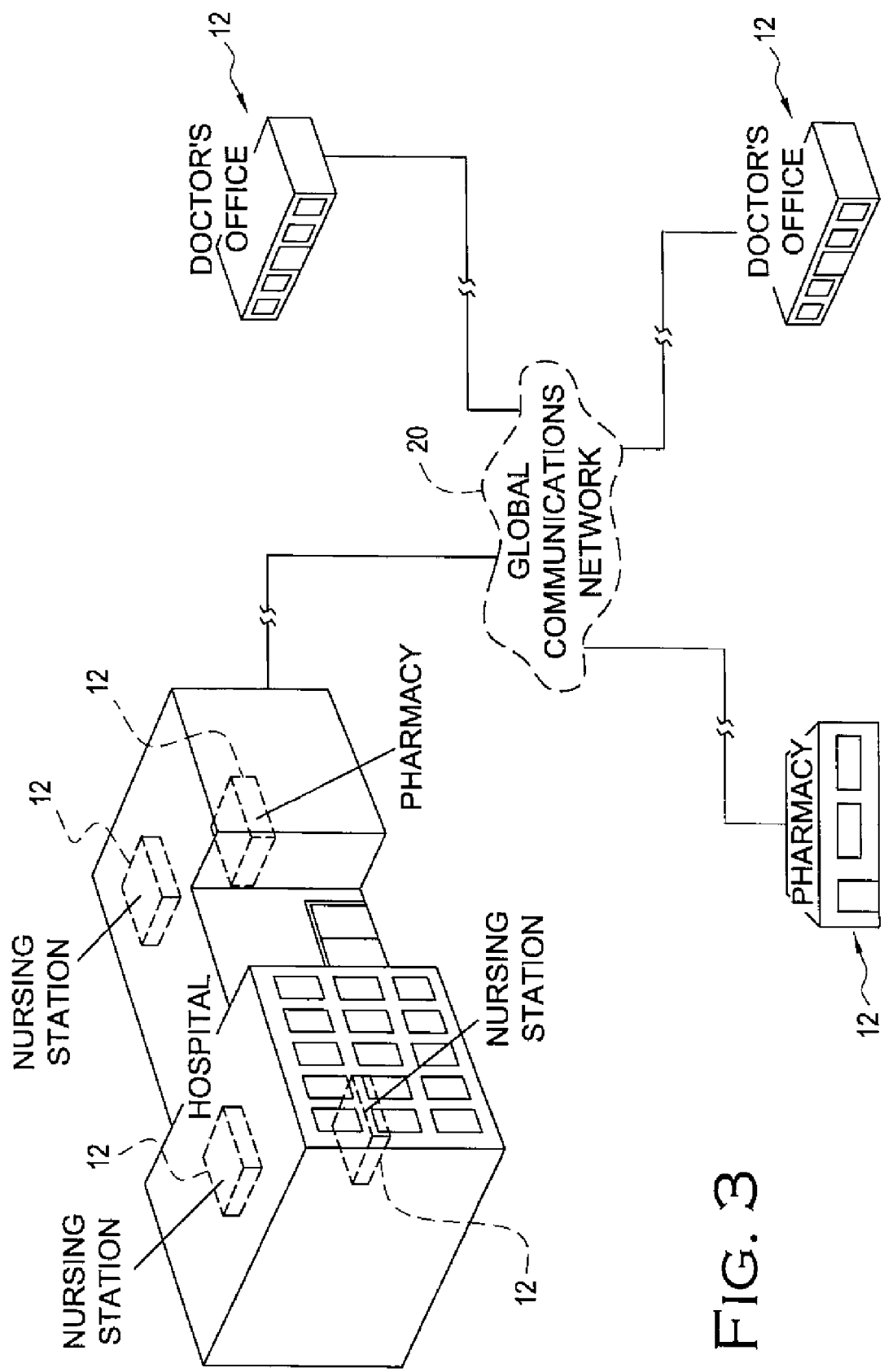
FIG. 3 is a schematic view of the medical professional monitoring system illustrated in FIG. 1 being used in a plurality of locations.
Figure 4:
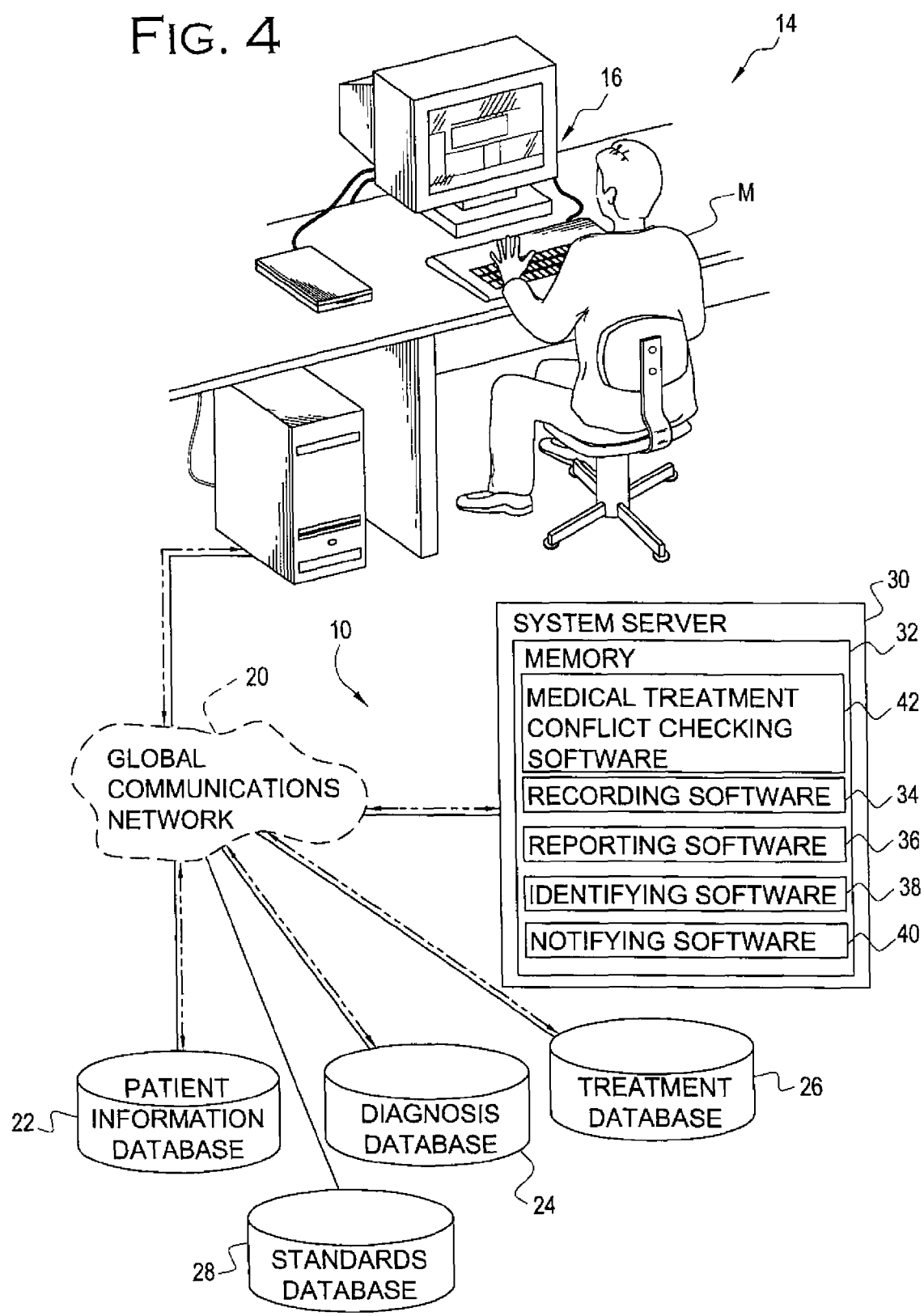
FIGS. 4-6 illustrate the various medical professional user sites illustrated in FIG. 1 using the medical professional monitoring system according to the present invention.
Figure 5:
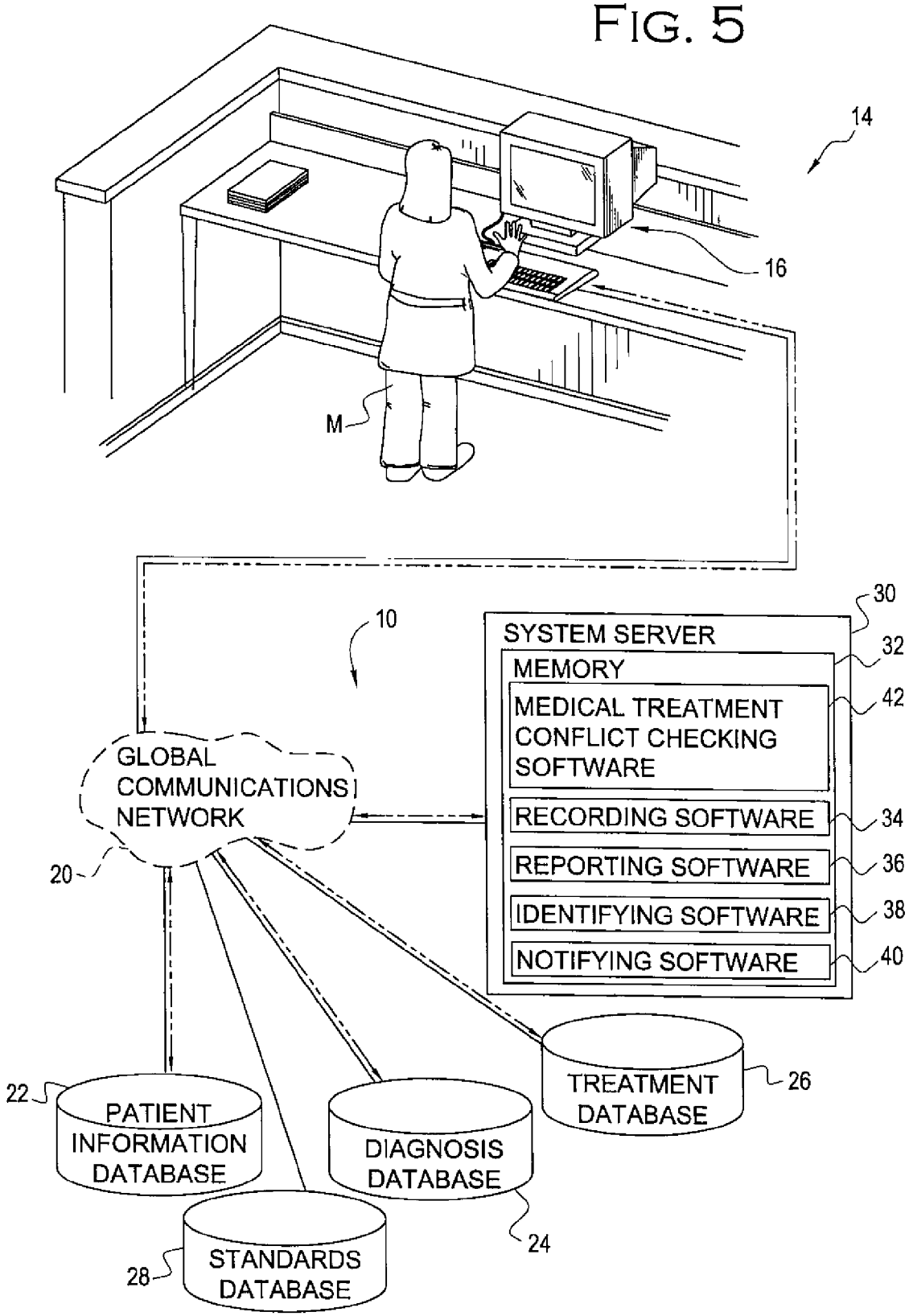
Figure 6:
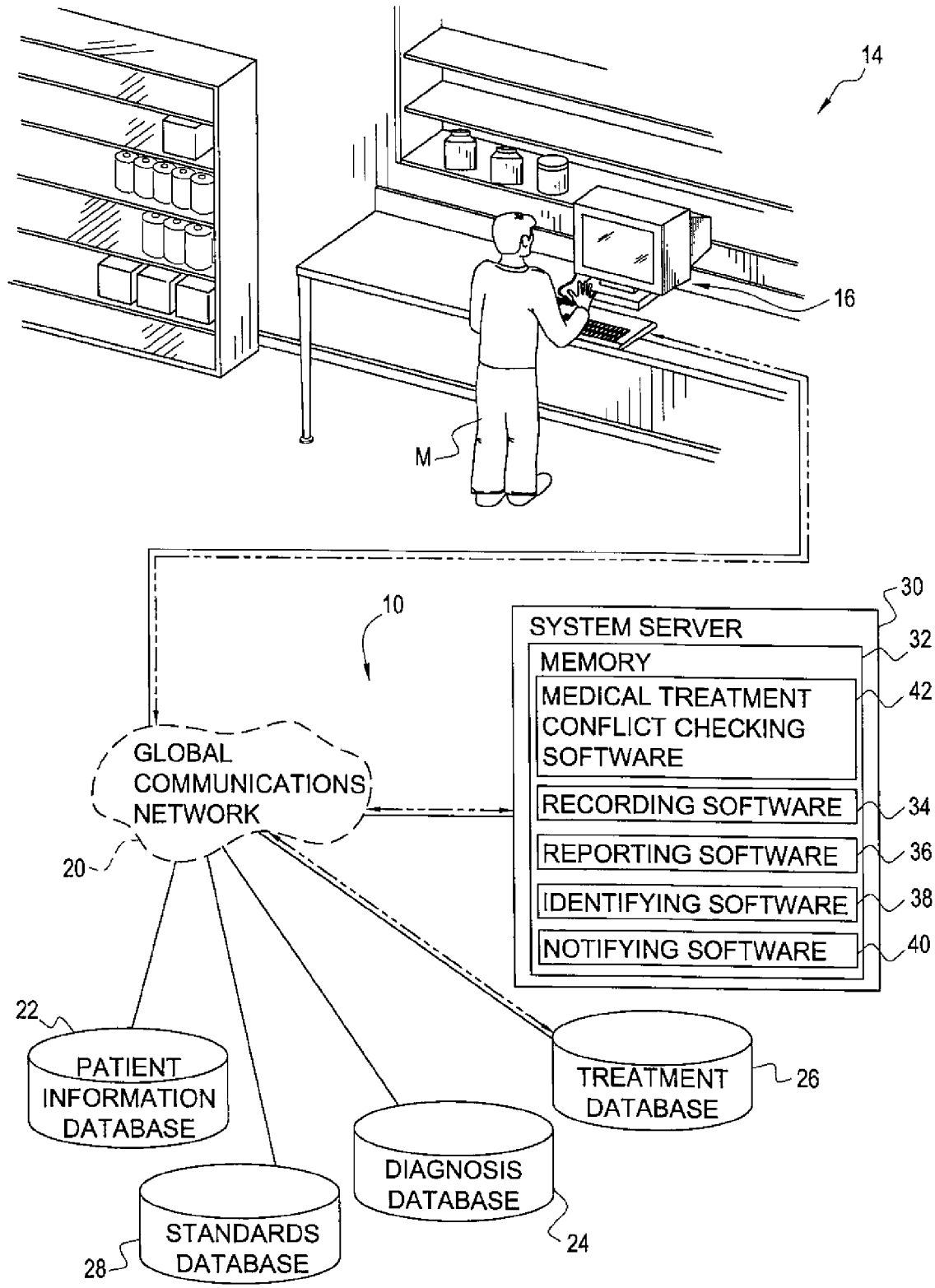

Referring initially to FIGS. 1 and 2, a medical professional monitoring system 10 according to the present invention is now described in greater detail. As illustrated in FIG. 1, the medical professional monitoring system 10 may be used in a plurality of medical professional user sites 12. Each of the medical professional user sites 12 illustratively includes a user workstation 14. Each of the user workstations 14 preferably includes a user interface 16 (illustrated in FIGS. 4-6), such as a computer, for example, that is in communication with a global communications network 20, i.e., the Internet.

The user interface 16 is preferably for use by a medical professional M, and may be provided by a computer, for example. Throughout this disclosure, the term medical professional M may be interchangeably used with the term user. Those skilled in the art, however, will appreciate that any other type of user interface 16 may be provided to accomplish the goals of the present invention. For example, the user interface 16 may be a personal digital assistant (PDA), or any other device that may be used to communicate over a global communications network 20. Another example of a user interface 16 may include a computer having a keyboard. Those skilled in the art will also appreciate that the user interface 16 may, for example, be provided by a scanner. This advantageously allows documents, such as patient charts, x-rays, etc. to be scanned and used in the medical professional monitoring system 10. The user interface 16 may generally be provided by any device that may be used by a medical professional M when conducting a medical examination, collecting patient information, performing a medical procedure or any other device used by a medical professional when making a medical related decision.

Some medical professionals M dictate information to be transcribed into patient charts. There currently exists voice recognition software that automatically transcribes such dictation, or that allows the medical professional to dictate information directly into a patient chart. Accordingly, the user interface 16 may be provided by a dictation-transcription device that is in communication with the global communications network 20 so that the medical professional M may dictate patient information, for example, to be used in the medical professional monitoring system 10.

The medical professional monitoring system 10 illustratively comprises a patient information database 22 in communication with the global communications network 20. The patient information database 22 preferably includes patient information for a plurality of patients. After a patient's information is entered into the patient information database 22, the patient may be defined as a registered patient. The patient information stored in the patient information database 22 is preferably kept strictly confidential, and access to patient information is heavily monitored to ensure patient privacy.

The patient information database 22 is accessible by medical professionals M. Further, the patient information database 22 may include such information as past patient medical history, patient address, prescriptions history, or any other type of patient information that may be necessary for a medical professional M to make an assessment of the patient, as understood by those skilled in the art. If the patient's current medical condition as presented to the medical professional M is not updated in the patient information database 22, the medical professional may still be able to access and utilize the diagnosis information in the diagnosis database 24.

The medical professional monitoring system 10 also illustratively includes a diagnosis database 24 in communication with the global communications network 20. The diagnosis database 24 is accessible by medical professionals M, and may include medical diagnosis information. More specifically, medical professionals M may access the diagnosis database 24 to select one of a plurality of diagnoses based upon patient information in the patient information database 22, and further based upon analysis of the patient as presented to them.

The medical professional monitoring system 10 may advantageously be an interactive system. In other words, the monitoring system 10 may analyze information in the patient information database 22, and compare that information with information in the diagnosis database 24 to suggest one of a plurality of diagnoses. Upon reviewing the suggested diagnosis, the medical professional M may chose to accept, reject, or amend the suggested diagnosis. Of course, a medical professional M will be free to diagnose a patient with a particular diagnosis regardless of whether that diagnosis is presented to the medical professional.

In other words, the medical professional M may override a diagnosis, if necessary. The system 10 according to the present invention advantageously is not advisory in nature, such as other systems that currently exist. In other words, the system of the present invention 10 is not designed to provide advice to a medical professional making a diagnosis. Instead, the system 10 according to the present invention advantageously ensures that the medical professional M follows various rules stored on the databases when carrying out several medical functions. More specifically, and by example only, the medical professional M is required to follow various rules, which may be stored on a medical practices database, when making a diagnosis, when ordering a medical treatment or procedure, when prescribing a medication, or for any other number of medical related decisions. As will be described in greater detail below, if the medical professional M does not follow particular rules, an error message may be generated and presented to the medical professional. The error message would preferably prevent the medical professional from continuing with making medical related decisions but, as described above, the medical professional may use an override function to continue when necessary.

The medical professional monitoring system 10 further illustratively includes a medical treatment database 26 in communication with the global communications network 20 and accessible by medical professionals M. The medical treatment database 26 preferably includes medical treatment information that may be used by the medical professional M to select a medical treatment based on the diagnosis information retrieved from the diagnosis database 24.

Again, since the medical professional monitoring system 10 is an interactive system, the information in the patient information database 22 and the diagnosis database 24 are analyzed so that the system presents a proposed medical treatment to the medical professional M selected from the medical treatment database 26. Again, and with reference to the rules above, the system 10 does not act as an advisory system, but only presents proposed medical treatments and/or medical diagnoses (or other medical related information) based on a comparison of information entered (preferably in the form of answers to questions presented to the medical professional, as will be discussed in greater detail below) with rules. Those skilled in the art will appreciate that the medical professionals M are not limited to the medical treatments listed in the medical treatment database 26, but rather may also select medical treatments that are not listed in the medical treatment database. This advantageously allows the medical professional M a great deal of latitude to experiment with alternative medical treatments, if desired, thereby generally advancing the practice of medicine.

Some of the information in the medical treatment database 26 may be related to medications. The medication information may include proper dosing, conflict warnings and a medication conflict check to analyze medications currently being used by the patient (which should be listed in the patient information database 22) for treatment conflicts. The medication information may also include insurance coverage, affordability, other alternative medications, i.e., generic medications, and availability.

Further, various medications may be presented to the medical professional M in a predetermined order such that the most commonly prescribed medication is presented to the medical professional first. Problem medications may be flagged so that such a problem is made aware to the medical professional M before prescribing the medication. The medications may also be presented in an order of affordability, i.e., present generic medications prior to non-generic medications, for example. Affordability may also be determined by insurance coverage of the patient. For example, one type of medication may be covered by a predetermined insurance policy, but not by others. This may be considered a rule that the medical professional must follow when prescribing a medication, for example. Any discussion above related to prescribing medications may also be applied when dealing with medical treatments, procedures, or other medical related decisions, as understood by those skilled in the art.

Other medical information that may be included in the medical treatment database 26 may be directed to medical tests. More particularly, the information may include various rules that typically govern the requirements necessary before a medical test may be ordered. Test options may be presented to the medical professional M, with the most common tests used for a particular diagnosis being presented to the medical professional first. The presentation of the medical tests to the medical professional M may be sorted depending upon the diagnosis, the current medications being used by the patient, contraindications, i.e., medical tests that may conflict with the patient's condition, insurance coverage, and other pertinent information, as understood by those skilled in the art.

Additional medical information that may be included in the medical treatment database 26 may be directed to medical procedures. More specifically, the information may include various rules that typically govern the requirements necessary before a medical procedure is ordered by a medical professional M. Compliance with the rules may be determined based on a comparison of information entered by the medical professional M to the rules. For example, the medical professional M may enter answers to questions presented. The answers may be compared to the rules before a medical procedure is authorized to ensure that the procedure is in compliance with the rules. These procedures may be presented to the medical professional M for review in a particular order. This order may be dependent upon the diagnosis, other available forms of therapy, contraindications, available insurance coverage, or any other number of related variables, as understood by those skilled in the art.

The medical treatment database 26 may also include information directed to medical recommendations. More specifically, the information may include various rules that typically govern the requirements necessary before a medical professional M makes a particular medical recommendation. These recommendations may include taking no action, making a summary of previous actions for the patient, providing the patient the results of previous actions, assigning a diagnosis category to the patient, i.e., resolved, inactive, stable, etc., communicating with other medical professionals M, or any other number of medical related recommendations, as understood by those skilled in the art.

The medical professional monitoring system 10 of the present invention may advantageously coordinate work flow between various medical professionals M. More particularly, the medical professional monitoring system 10 may coordinate work flow between departments in a medical facility, e.g., between a physician and a pharmacist, or between medical professionals practicing in different areas of medicine, e.g., between a cardiologist and an anesthesiologist. Those skilled in the art will appreciate that coordination of work flow can include coordination between any number of various medical professionals M. Coordination such as this advantageously enhances medical treatment by ensuring that necessary steps are taken in the proper order when administering medical treatment. Further, this advantageously enhances medical treatment by ensuring that various steps of a proposed medical treatment are not duplicated. Additional features to minimize, and possibly prevent, duplicative steps are discussed in greater detail below.

The medical professional monitoring system 10 according to the present invention also illustratively includes a server 30 in communication with the global communications network 20 that is accessible by medical professionals M. Those skilled in the art will appreciate that the server 30 may either be an on-site server or an off-site server. On-site servers are advantageous from a maintenance point of view. In other words, on-site servers may advantageously be readily maintained in the office of the medical professional M. An on-site server is preferably positioned in communication with other servers of the medical professional monitoring system 10 via the global communications network 20.

On-site servers may download updates to the medical professional monitoring system 10 from off-site servers when necessary, or any other source, as understood by those skilled in the art. More specifically, updates may be automatically sent to the on-site servers or, alternately, a medical professional M may transmit a request to an off-site server for available updates. Additional information on updating the medical professional monitoring system 10 is described in greater detail below. Updating information to be used in connection with the medical professional monitoring system 10 is preferably automated to advantageously enhance reliability of the system.

The server 30 illustratively includes a memory 32 and a recording system 34 to record medical treatments selected by the medical professional M. The recording system 34 may also track the selected medical treatments for compliance with at least one predetermined standard (or rule) selected from a plurality of predetermined standards (or rules). The recording system 34 may also monitor the frequency with which a medical professional M makes an incorrect or improper diagnosis. Accordingly, a medical professional M may be rated based upon their frequency of incorrect or improper diagnoses and/or the frequency of non-compliance with the predetermined standards. Many steps are taken before it is determined that a medical professional M has made an incorrect or improper diagnosis. A medical professional M may have several reasons for making a diagnosis or prescribing a particular medical treatment that may be viewed as incorrect or improper. More specifically, a medical professional M may desire to experiment with alternate treatment, or may make a finding that an existing treatment is outdated. In such cases, the medical professional monitoring system 10 advantageously allows the medical professional M with the ability to override any indications that the medical professional has made an improper or incorrect diagnosis. In some embodiments, such an error message may prevent the medical professional M from moving forward with using the system. This, however, can also be overridden by the medical professional. Any overriding of such an indication, however, is recorded by the recording system.

The medical professional monitoring system 10 of the present invention fully accounts for the fact that medical professionals M advance the practice of medicine by experimenting with alternative medical treatments. The recording system 34 may illustratively be provided by recording software, but those skilled in the art will appreciate that any other type of system capable of recording, tracking, and/or monitoring medical treatments selected by the medical professionals M may also be suitable.

To be specific, the medical professional monitoring system 10 may be provided by software, and the recording system may be an add on to the software, or may be integrated into the software. Those skilled in the art will appreciate that the medical professional monitoring system 10 may be provided in disk form, i.e., stored on a computer readable medium, or may be stored on a central server that is accessible by a user or medical professional M and available for download.

The medical professional monitoring system 10 also illustratively comprises a standards database 28 in communication with the global communications network 20. The standards database 28 preferably includes a plurality of predetermined standards. The predetermined standards are preferably medical standards, such as hospital standards, insurance standards, medical treatment standards, i.e., practice guidelines, pharmaceutical standards, medical office standards, emergency response standards, or any other type of medical standard, as understood by those skilled in the art. Those skilled in the art will also appreciate that insurance standards may be provided by insurance guidelines, such as medical necessity guidelines, coding guidelines, and approval guidelines. The standards stored on the standards database 28 may also be defined as rules.

The standards database 28 is preferably updatable so that new standards may be added to the standards database, and so that the new standards are recognized by the medical professional monitoring system 10. For example, hospitals may update certain standards, such as medical procedures, protocols, and acceptable medications, based on new medical research or findings. Accordingly, it is advantageous to update the standards database 28 based upon that information. Further, and also for example, as new medications become available, it may be desirable to update pharmaceutical standards in the standards database 28.

The medical professional monitoring system 10 may further include a reporting system 36. The reporting system 36 may be carried by the memory 32 of the system server 30, and may identify medical professionals M that select a medical treatment that is not compliant with at least one of the predetermined standards in the standards database 28. The reporting system 36 may advantageously request additional information directed to a medical professional's M reason for selecting a medical treatment that is not in compliance with at least one of the plurality of predetermined standards, or rules, in the standards database 28. Of course, it is not necessarily improper for a medical professional M to select a medical treatment that is not in compliance with at least one of the predetermined standards, or rules, in the standards database 28. Experimentation with alternative medical treatments advantageously advances the practice of medicine.

Therefore, the medical professional monitoring system 10 of the present invention allows a medical professional M to override a proposed medical diagnosis and medical treatment. Further, after the medical professional M has selected or made a medical diagnosis for a patient's particular condition, the diagnosis and medical treatment may be cross referenced against both the information in the patient information database 22 and the standards database 28 to determined if the proposed medical procedure is a procedure that is covered by the patient's insurance, for example.

More specifically, the medical professional monitoring system 10 of the present invention advantageously includes an automated audit process. For example, and insurance company may audit a medical chart to make sure that various tests and procedures ordered by the medical professional M meet certain criteria. Those skilled in the art will appreciate that this auditing process is carried out with full disclosure of the information in the medical chart. The criteria that are referenced during the auditing process may be located in the standards database 28, for example. Similarly, tests and procedures ordered by the medical professional M may also be audited for compliance with other standards set forth in the standards database 28.

Accordingly, and with reference to the auditing capabilities provided to insurance companies, the medical professional M is able to determine whether or not a procedure or test is covered by insurance prior to performing the procedure or test. More particularly, the medical professional M may determine the amount covered according to the patient's policy and the doctor's contract (or any other contract for medical services), and what can be done about the difference between the amount charged and the amount approved for payment by the insurance carrier, i.e., contractual write off, bill the patient partially or in full, etc. For example, in some cases, an insurance company may request that a medical professional M first perform a procedure before making a determination of whether the procedure is a covered procedure. If it is determined by the insurance company that the procedure is not covered, then the medical professional M may only be able to receive payment for the procedure from the patient. In some cases, the patient may be unable to pay. The auditing capabilities of the medical professional monitoring system 10 of the present invention advantageously provides both the medical professional M and the patient with knowledge and peace of mind as to whether or not the procedure will be covered by insurance prior to carrying out the procedure.

The auditing capabilities of the medical professional monitoring system 10 of the present invention may advantageously be automated. This allows for determinations as to the appropriateness of a procedure and/or test to be made in a more rapid fashion. Further, automation of the auditing process advantageously enhances the efficiency of the medical professional monitoring system 10. Accordingly, the automation of the auditing process of the medical professional monitoring system 10 advantageously allows certain procedures to be pre-approved. Of course, those skilled in the art will appreciate that if it is determined that a procedure or test is not pre-approved, the patient may still have the option to move forward with the procedure.

In some cases, the medical treatment that the medical professional M determines to be the best course of action for a patient may not be affordable to the patient, i.e., the proposed medical treatment is not covered by the patient's insurance, and the patient may not have any other way to pay for the proposed treatment. The medically professional monitoring system 10 of the present invention therefore advantageously suggests alternate medical treatments to the medical professional M. Further, the medical professional monitoring system 10 also advantageously allows the patient to make a determination as to whether or not to proceed with the medical treatment.

Accordingly, the reporting system 36 may advantageously determine if a deviation in medical treatment from at least one of the predetermined standards in the standards database 28 produces a better result, i.e., an improvement in medical treatment. If, however, it is determined that the proposed medical treatment does not produces a better treatment result, and it is not in compliance with at least one of the standards, or rules, in the standards database, then the medical professional M that is prescribing the particular medical treatment may be identified by the reporting system 36. After such a medical professional M is identified by the reporting system 36, the medical professional may be reported to a reporting agency. In some cases, the reporting system 36 may monitor the outcome of a prescribed medical treatment, and may make a report based on the outcome. To monitor the outcome of a prescribed medical treatment, it may be necessary for a medical professional M, or other user of the system 36 to input the outcome of the treatment.

The reporting agency is preferably provided by a quality assurance department that may be found in a medical facility. Those skilled in the art, however, will also appreciate that the reporting agency may, for example, be a hospital administrator, a medical professional review board, or any other type of reporting agency that monitors the fitness of a medical professional M. The reporting agency may also be in place to determine the feasibility and applicability of the rules and standards, as well as medical procedures, medications, medical tests, and other medical related issues. This advantageously ensures that the system 10 is as up to date as possible as the field of medicine advances. The reporting system 36 may illustratively be provided by reporting software, but those skilled in the art will appreciate that any other type of system capable of reporting information regarding a medical professional M to a reporting agency may also be suitable.

A processor (not shown) may be used to process information on the server 30 of the medical professional monitoring system 10. Accordingly, the processor may process information on the patient information database 22, the diagnosis database 24, the treatment database 26 and the standards database 28 so that a medical professional M may properly use the medical professional monitoring system 10 to provide enhanced medical care.

Use of the medical professional monitoring system 10 may begin when a medical professional M accesses and updates the patient information database 22 with patient information. This can be patient information that the medical professional M obtains from the patient, or patient information that the medical professional observes. The patient information may be gathered using a question and answer format. In other words, the medical professional monitoring system 10 may present a series of questions to the medical professional M, the answers to which are used to update patient information in the patient information database 22. Those skilled in the art will appreciate that the patient information to be inputted into the patient information database 22 may also be imported from another patient information database, or from another source.

Those skilled in the art will also appreciate that the question and answer format described above may be used to record medical observations and also may be used to select medical treatments. The rules aspect of the present invention may be used to prevent the medical professional M from moving forward with an examination if an improper finding is made in an answer to a question. More details regarding the rules aspect of the invention will be discussed in greater detail below.

Thereafter, the medical professional M may either select a medical diagnosis from the diagnosis database 24, or a processor located on the system server 30 may be used to process patient information and provide the medical professional with a diagnosis. After the medical professional M has made a determination as to a diagnosis of a patient's condition, the medical professional may engage in any number of medical treatments, such as prescribing medications, performing additional medical tests, performing medical procedures, or simply making medical recommendations. After the medical professional M has administered the medical treatment, i.e., prescribed medication, performed a procedure, made a medical recommendation, etc., the new information may be inputted into the patient information database 22 so that the patient information in the patient information database remains up to date.

All of the databases of the medical professional monitoring system 10, i.e., the patient information database 22, the diagnosis database 24, the treatment database 26 and the standards database 28, may all include a question and answer format. More particularly, a medical professional M that is using the system 10 may be presented with a question from any one of the databases in order to provide additional information that may be necessary, or to further process the patient for receipt of suitable medical care. Further, a processor located on the server 30 may automatically generate a question to be presented to the medical professional M when providing medical treatment to thereby advantageously enhance medical treatment.

After the medical professional M has made a determination as to a desired question to ask of the patient regarding the patient's medical condition, the medical professional may receive an answer from the patient that is expected and that may already exist in the database in an answer format. After the answer is properly determine the system 10 may determine if additional information is necessary and, if so, may prompt the medical professional to ask additional questions. This may advantageously assist the medical professional in narrowing a possible medical diagnosis which may be selected from the diagnosis database 24, or selecting a medical treatment, such as prescribing medications, performing additional medical tests, performing medical procedures, or simply making medical recommendations, which may be selected from the medical treatment database 26, for example. The questions presented to the medical professional M are not necessarily questions that are to be relayed to the patient, but rather may be questions that are designed for the medical professional to answer. The medical professional M may thereafter update the patient information database 22 with information directed to the prescribed medical treatment.

Throughout the procedure of using the medical professional monitoring system 10 of the present invention, all of the above referenced steps are preferably validated. For example, the patient information that is inputted into the patient information database 22 may be validated as being accurate. Also for example, the diagnosis selected by the medical professional M, as well as the selected medical treatment may be validated by comparison with the predetermined standards, or rules, in the standards database 28. If, during this validation process, additional information is necessary to assist in the diagnosis or treatment of the patient, the system 10 may present questions directed to obtaining the additional information to the medical professional M. The medical professional M may thereafter determine whether or not it is necessary to ask the patient those questions. In other words, the medical professional M advantageously maintains control of medical treatment. As described above, these standards, or guidelines/rules, may, for example, include individual standards, practice standards, facility standards, and standards set by an insurance company.

The selected medical treatments may be tracked for quality assurance purposes, and errors made by a medical professional M may be reported. These errors may be reported even if the medical professional monitoring system 10 corrects the errors pursuant to information provided to the medical professional M by the medical professional monitoring system. The medical treatments and procedures selected by the medical professional M may then be transmitted to an insurance company, for example, for immediate payment. Those skilled in the art will appreciate that this information does not necessarily have to be transmitted to an insurance company for payment, but rather may be transmitted to any party responsible for payment of the medical treatment and/or procedures.

The medical professional monitoring system 10 may also include a medical professional identification system 38. The medical professional identification system 38 may be carried by the memory 32 of the system server 30. More specifically, the medical professional identification system 38 preferably identifies the medical professional M that has accessed at least one of the patient information database 22, the diagnosis database 24, the treatment database 26, and the standards database 28. The medical professional identification system 38 may be provided by identifying software, but those skilled in the art will appreciate that any other type of system capable of identifying the medical professionals M may also be suitable. The identification software may prompt a user for a user ID and a password to authenticate and identify each medical professional M accessing one of the patient information database 22, diagnosis database 24, treatment database 26, or standards database 28. This advantageously enhances security of the medical professional monitoring system 10. The present invention also contemplates the use of fingerprint scanning of a medical professional M or user to ensure the identity and authority of someone using the system.

The medical professional monitoring system 10 may also include a notification system 40 in communication with the global communications network 20. More specifically, the notification system 40 may be carried by the memory 32 of the systems server 30. The notification system 40 preferably notifies an insurance company of patient treatment. Accordingly, the time that it normally takes for an insurance company to transmit payment for a medical treatment to the medical professional M may advantageously be decreased.

The notification system 40 may also advantageously reduce administrative costs of insurance carriers. More particularly, the notification system 40 preferably validates information as it is being transmitted to the insurance carrier. This advantageously greatly reduces administrative costs associated with validation of medical treatments or procedures when received by the insurance carrier. The notification system 40 may be provided by notifying software, or any other type of system that provides a rapid notification of medical treatment to the insurance company as understood by those skilled in the art.

The medical professional monitoring system 10 may also illustratively include a medical treatment conflict check system 42 in communication with the global communications network 20. The medical treatment conflict check system 42 may be carried by the memory 32 of the systems server 30.

The medical treatment conflict check system 42 may check a medical treatment selected by a medical professional M for any conflicts with a patient's existing medical treatments. More specifically, the medical treatment conflict check system 42 preferably checks prior diagnoses, current and previous medications, previous physicians, and related treatments. For example, the medical treatment conflict check system 42 may compare a medication prescribed by the medical professional M with patient information in the patient information database 22 to determine whether or not the patient is allergic to the medication.

The medical treatment conflict check system 42 may also identify other errors that may be caused by a lack of action on the part of the medical professional M. For example, the medical treatment conflict check system 42 may detect an incomplete medical history, an incomplete physical examination, a missed diagnosis, other needed medications that were not prescribed, other necessary medical tests that were not ordered, other needed medical procedures that were not recommended or performed by the medical professional M, and instructions that were not provided to the patient. Those skilled in the art will appreciate that other types of medical conflicts may also be checked by the medical treatment conflict check system 42. The medical treatment conflict check system 42 may be provided by medical treatment conflict checking software, or any other type of system capable of checking for medical conflicts between existing medical treatments and new medical treatments as understood by those skilled in the art.

As discussed above, the patient information database 22, the diagnosis database 24, the medical treatment database 26, and the standards database 28 may all be updatable. Accordingly, the medical professional monitoring system 10 advantageously includes up to date information so that a medical professional M may make an appropriate diagnosis of the patient condition, and prescribe the most up to date medical treatment available.

Referring now additionally to FIGS. 3-6, several uses of the medical professional monitoring system 10 at several different medical professional user sites 12 are now described in greater detail. For example, the medical professional monitoring system 10 may be used in a physician's office (FIG. 4), in a laboratory (FIG. 5), or a pharmacy (FIG. 6), for example. The medical professionals M may be physicians, physician assistants, nurses, pharmacists, dieticians, laboratory technicians, emergency responders, or any other type of medical professional as understood by those skilled in the art. As described above, any medical professional M is considered a user of the system. Those skilled in the art, however, will appreciate that a user of the system does not necessarily need to be a medical professional. Further, the medical professional monitoring system 10 may, for example, be used by an emergency responder in the field. Accordingly, the medical professional monitoring system 10 allows for communication between many medical professional user sites 12 as well as between many medical professionals M. The medical professional monitoring system 10 advantageously enhances communications between medical professionals M.

For example, a pharmacist may be instantly notified when a physician changes a patient's prescription. In some cases, a pharmacy may automatically send a patient his or her medications. The enhanced communication between medical professionals M provided by the medical professional monitoring system 10 advantageously prevents this type of redundancy and/or waste. A pharmacy, for example, may also be enabled with the ability to check whether the medical professional M. still desires a patient to receive the medication, or if it has been cancelled or changed before dispensing.

The medical professional monitoring system 10 may, for example, also advantageously provide a physician access to several different medications available to be prescribed for a certain condition. Accordingly, the physician may be able to prescribe a generic medication, which, in turn, may save money for patients. The medical professional monitoring system 10 may, for example, further advantageously prevent insurance fraud. For example, the enhanced communication provided by the medical professional monitoring system 10 between medical professionals M prevents non-medical professionals from accessing certain databases and making changes, e.g., calling a fraudulent prescription into a pharmacy.

The medical professional monitoring system 10 of the present invention also advantageously includes searching and indexing capabilities. For example, the searching and indexing capabilities advantageously allows a medical professional M using the medical professional monitoring system 10 to search patient information on the patient information database 22. Those skilled in the art will appreciate that the searching and indexing capability of the medical professional monitoring system 10 is secured. Accordingly, medical professionals M may advantageously access information on the system 10 in a manner that allows for the security of patient information, for example, to be maintained.

More specifically, the indexing and searching capabilities of the medical professional monitoring system 10 may operate similar to a search engine. In other words the indexing and searching capabilities allow a user of the medical professional monitoring system 10 to search for information directed to a particular patient stored on other databases, even if the databases are not a part of the medical professional monitoring system. For example, the searching and indexing capabilities of the medical professional monitoring system 10 advantageously allows a medical professional M using the medical professional monitoring system to search for patient information that may be stored on a computer system of another medical professional, even if the other medical professional is not a user of the medical professional monitoring system. Those skilled in the art will appreciate that the indexing capabilities of the medical professional monitoring system 10 allows for patient information to be located regardless of the location of the information, i.e., the information does not necessarily need to be stored at a medical facility. Those skilled in the art will appreciate that privacy of patient information will always be maintained. Therefore, patient information will not be obtainable unless the patient has waived the right to privacy of the information, or has provided specific consent to release such information.

The system can also allow a user to search for medical related information directed to a particular patient, no matter where that information is located. For example, with one search, a patient's complete medical records can be searched. This can include doctor records, a therapy records, pharmacy records, etc. Searches can be performed either globally or regionally, and can also be limited to particular fields. In other words, a search can be performed for pharmacy records on a patient in a particular geographical location.

A medical professional M using the medical professional monitoring system 10 of the present invention in a pharmacy may advantageously search the patient information database 22 to check if a prescription is valid. Upon determining that the prescription is valid, the medical professional M may validate the prescription. This advantageously reduces fraud that may occur in the medical field, e.g., fraudulent prescriptions.

Figure 7:
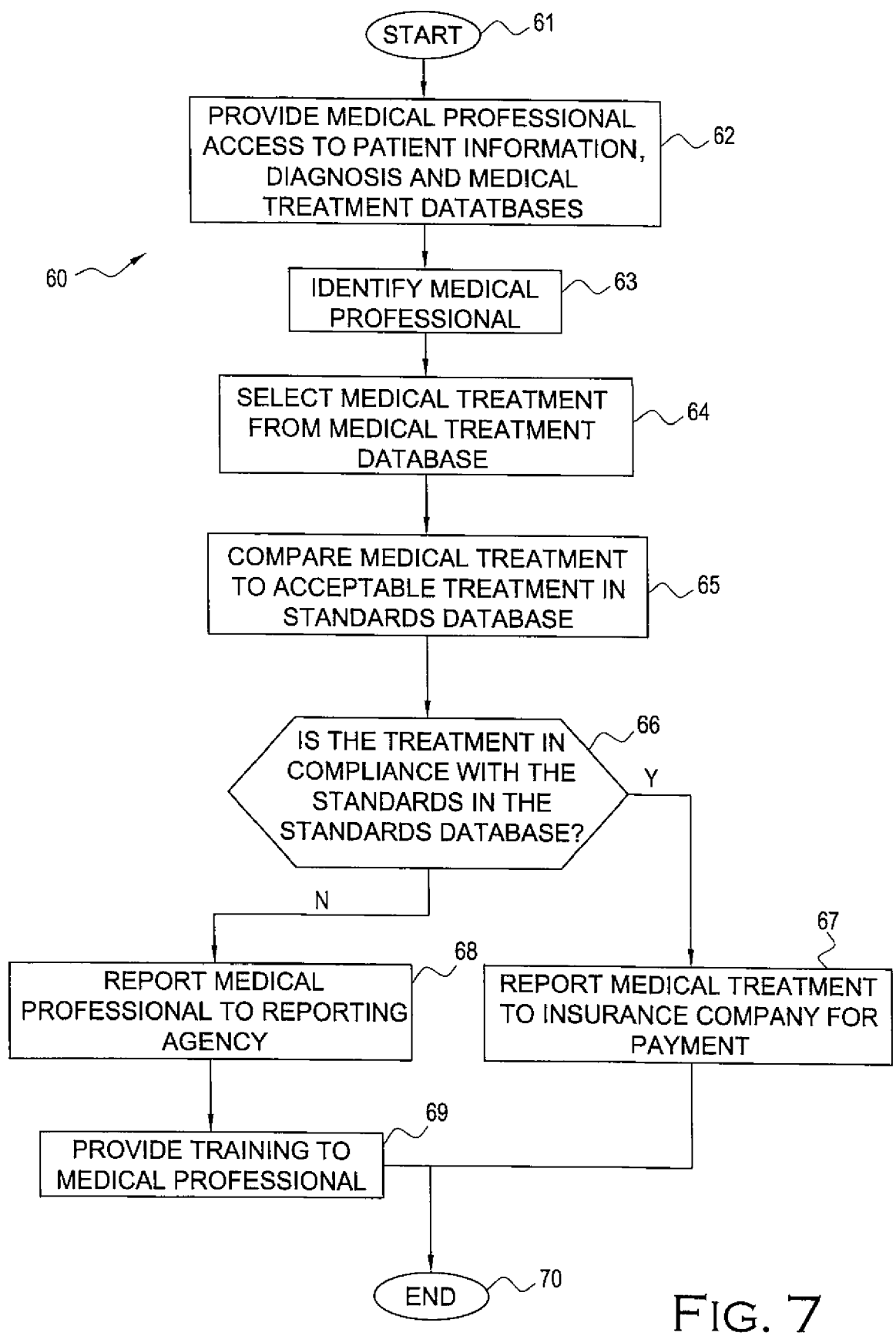
FIG. 7 is a flow chart illustrating a method for monitoring a medical professional according to the present invention.

Referring now additionally to the flowchart 60 of FIG. 7, a method of monitoring a medical professional M is now described. From the start (Block 61), a medical professional M is provided access to the patient information database 22, the diagnosis database 24, and the medical treatment database 26 at Block 62. At Block 63, the medical professional M is identified. A medical treatment is selected from the medical treatment database 26 at Block 64.

At Block 65, the medical treatment is compared to acceptable medical treatments in the standards database 28. At Block 66 it is determined whether the selected medical treatment is in compliance with the standards in the standards database 28. If it is determined at Block 66 that the selected medical treatment is in compliance with the standards in the standards database 28, then the medical treatment is reported to an insurance company for payment at Block 67. After having had the benefit of this disclosure, those skilled in the art will appreciate that payment for medical services through an insurance company generally must be in compliance with rules and standards set forth by the insurance company. These rules may, for example, be defined as insurance reimbursement rules. If, however, it is determined at Block 66 that the selected medical treatment is not in compliance with the standards in the standards database 28, then the medical professional M is reported to a reporting agency at Block 68, and training is provided to the medical professional at Block 69. Thereafter, the method is ended at Block 70.

Figure 8:
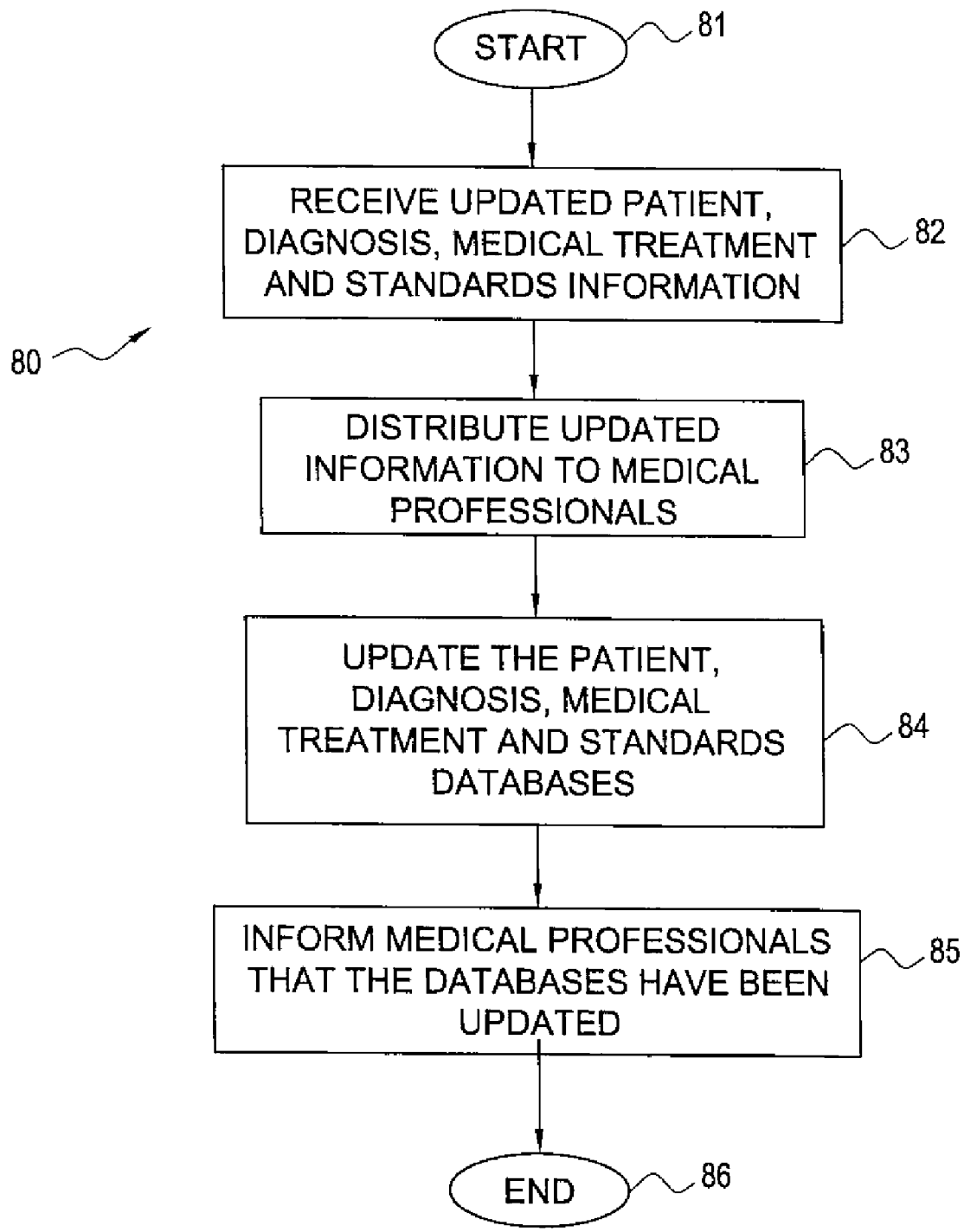
FIG. 8 is a flow chart illustrating a method for updating databases of the medical professional monitoring system according to the present invention.

Referring now additionally to the flowchart 80 of FIG. 8, a method for updating databases is now described in greater detail. From the start (Block 81), updated patient information, diagnosis information, medical treatment information, and standards information is received at Block 82. This information may be provided, for example, by consultants, committees, peer reviewers, insurance carriers, or any other agency or group related to the medical field and that may have valuable input as to proposed diagnosis, treatment, and standards information, as understood by those skilled in the art. Further, patients may provide medical professionals M with updated patient information so that the patient information database 22 may be updated.

At Block 83, the updated information is distributed to the medical professionals M. At Block 84, the patient information database 22, the diagnosis database 24, the medical treatment database 26, and the standards database 28, are each updated with the new information. It is preferable that a medical professional M performs the update of the medical professional monitoring system 10, but those skilled in the art will appreciate that anyone familiar with the system, such as a system technician, for example, may also update the databases of the system. Medical professionals M are informed that the databases have been updated at Block 85. Thereafter, the method is ended at Block 86.

Figure 9:
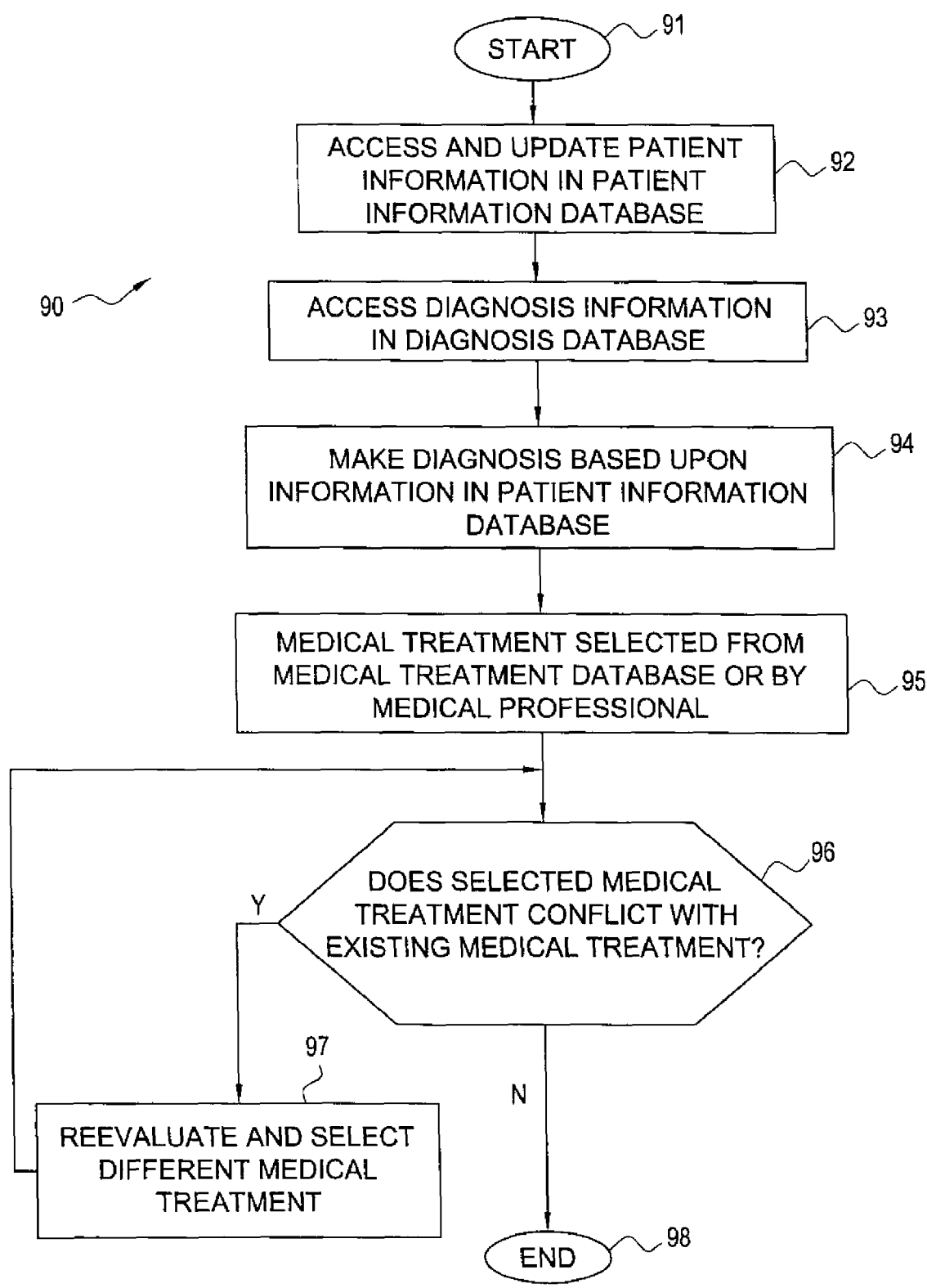
FIG. 9 is a flow chart illustrating a method for selecting a medical treatment according to the present invention.

Referring now additionally to the flowchart 90 of FIG. 9, a method for selecting a medical treatment is now described in greater detail. From the start (Block 91), patient information in the patient information database 22 is accessed and updated at Block 92. At Block 93, diagnosis information in the diagnosis database 24 is accessed. A diagnosis is made based upon information in the patient information database 22 at Block 94. At Block 95, a medical treatment is selected from the medical treatment database 26 or by a medical professional M.

At Block 96, it is determined whether the medical treatment selected from the medical treatment database 26 or by the medical professional M conflicts with a patients existing medical treatment. If it is determined at Block 96 that the selected medical treatment conflicts with a patients existing medical treatment, then the medical treatment is reevaluated at Block 97 and a different medical treatment is selected. Thereafter, it is determined whether the new medical treatment conflicts with a patient's existing medical treatment at Block 96. If a selected medical treatment does not conflict with a patient's existing medical treatment, then the method is ended at Block 98.

Several terms are used throughout this disclosure that may have several interpretations. The information relating to some of these terms provided herein is not meant to be limiting but rather exemplary. Patient information is meant to include any information relating to a patient such as, for example, patient history information, patient address, patient insurance information, or any other information relating to a patient as understood by those skilled in the art. A patient diagnosis is meant to relate to the act or process of identifying or determining the nature and cause of a disease or injury through evaluation of patient history, examination and review of laboratory data. This can also include a medical related opinion derived from an evaluation of a patient. Again, this is not meant to be limiting, but rather exemplary of a patient diagnosis. Medical recommendations are meant to include any healthcare related recommendation made by any healthcare provider. These recommendations may include, but are not necessarily limited to medical procedures, medical tests, surgeries, medications, physical therapy, education, lifestyle changes, diet changes, environmental changes, etc. Similarly, healthcare professionals include, but are not limited to, doctors, nurses, physical therapists, physicians assistants, pharmacists, etc.

Best practice guidelines are meant to refer to guidelines that should be followed based on recommendations of an issuing authority. These may be, but are not limited to, a doctor, a practice, a hospital, a clinic, an Emergency Room, an academy, a medical society, or any other issuing authority as understood by those skilled in the art. Insurance guidelines are meant to refer to guidelines that should be followed in order to meet reimbursement criteria based on requirements set forth by the payer. Again, this is intended to be exemplary in nature and not limiting.

Rules refer to statements or orders that dictate how medical related information is handled. This includes how a medical related procedure is carried out, how medical related information is collected, how a diagnosis is made, how medication is prescribed, when a test is appropriate, determination of whether or not a patient is a candidate to receive a medication or a test, determining if it is proper to discharge a patient, determining whether or not a diagnosis is appropriate, or any other number of criteria relating to the medical industry in general. Rules can also be considered a prescribed guide for medical related conduct or action, or a regulation or bylaw governing procedures or controlling conduct. Rules can also be directed to the insurance industry, i.e., insurance reimbursement rules. In short, a rule is considered a regulating principle. There can be several different types of rules. For example, rules may be directed to insurance coverage, insurance reimbursement, medical practices, medical diagnoses, medical procedures, medications, testing, patient information, healthcare providers, medical facilities, medical societies, regulatory requirements, medical therapies, and evidence based rules.

A medical condition as used herein is directed to a diagnosis, symptom or finding, e.g., clinical, test, laboratory or other. The present invention advantageously provides a medical professional with override authority. Override authority advantageously allows the medical professional with the ability to override a system requirement. This is not something that a medical professional can engage in simply because the medical professional is not satisfied with the result or indications received from the system. Instead, override authority is closely monitored and requires the medical professional to enter acceptable reasoning why the override is being used.

As described above, and as will be described in greater detail below, the present invention uses a plurality of databases to carry out the functionality of the system. These databases are stored on a computer readable medium, or are accessible via a global communications network. The databases may, for example, take several forms, such as tables, computer readable forms, values or, in general, any repository of information from which various pieces of information may be accessed. After having had the benefit of this disclosure, those skilled in the art will also appreciate that the databases or database information may be downloaded by a user from a central server.

Figure 10:
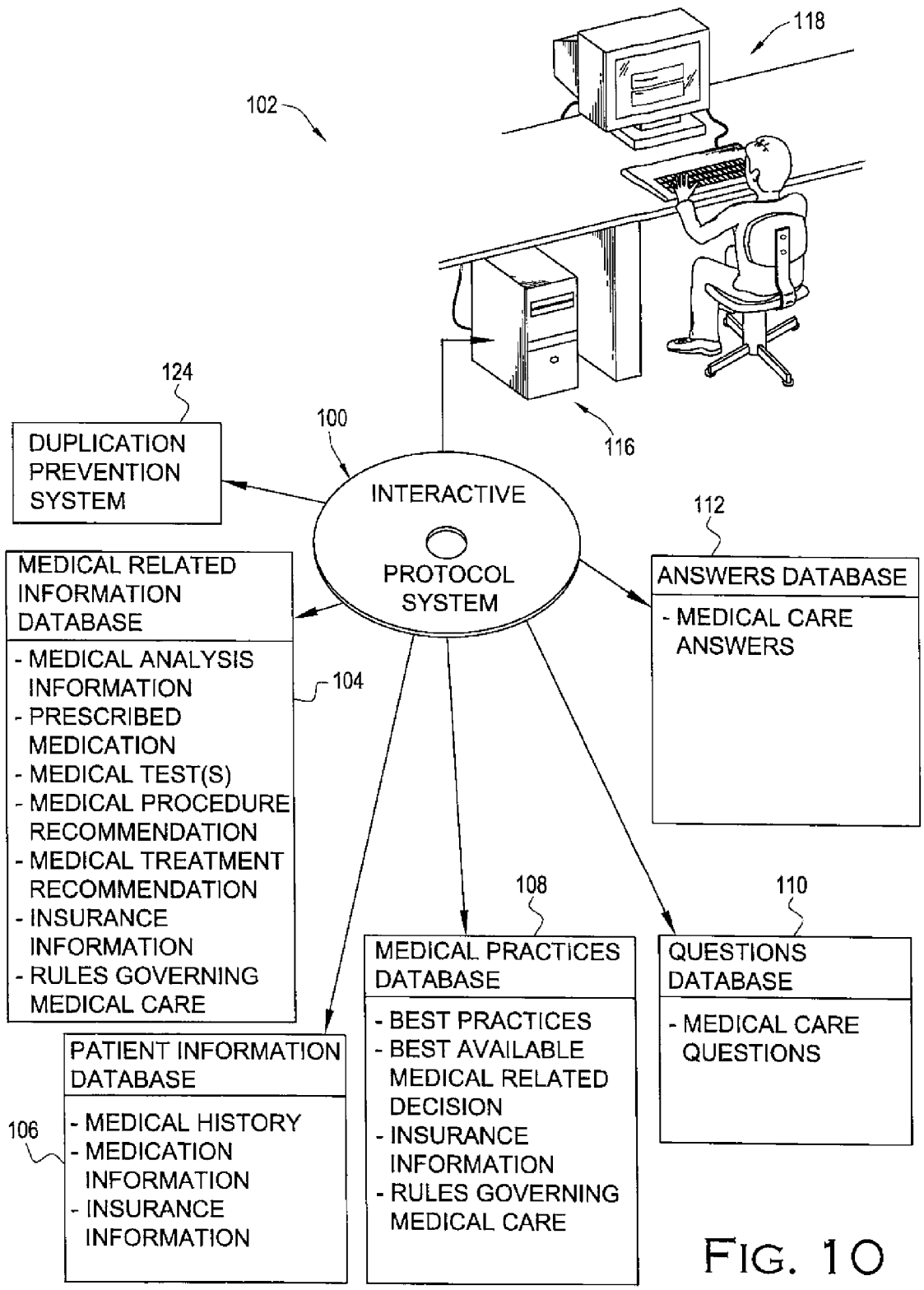
FIGS. 10-11 are schematic views of an interactive protocol system according to the present invention providing a user with best practices information.
Figure 11:
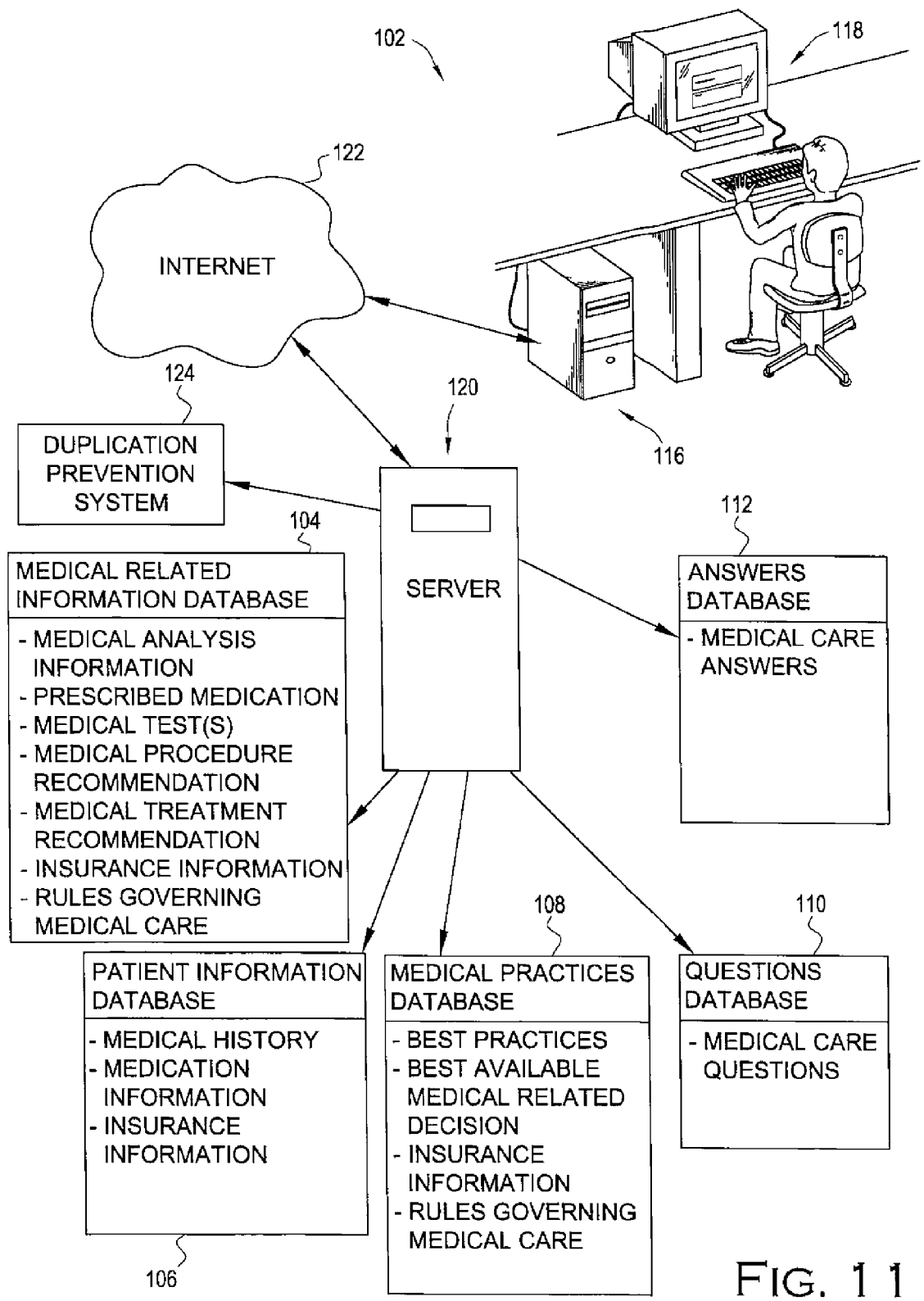

Referring now to FIGS. 10 and 11, an interactive protocol system 100 for a medical decision system 102 is now described in greater detail. The interactive protocol system 100 preferably includes a plurality of medical related information databases 104 containing medical related information and rules governing medical care. This system 100 also preferably includes a patient information database 106 including patient information and a medical practices database 108 including information relating to medical practices. The medical practices database 108 also includes insurance information. Accordingly, the medical practices database 108 may include best practices as understood by those skilled in the art, best available medical related decisions based on certain scenarios, best available insurance information necessary for making a medical related decision, and rules. Those skilled in the art will appreciate that the rules on the medical practices database govern medical care, i.e., these are rules that must generally be followed in order to assure that the best medical decision for each patient can be made. The interactive protocol system 100 according to the present invention further preferably includes a questions database 110 including questions to be presented to a user relating to medical care, and an answers database 112 including answers related to the respective questions in the questions database.

After having had the benefit of reviewing this disclosure, those skilled in the art will appreciate that the questions and answers of the present invention contemplate any way in which information is relayed to the system about a patient or medical care in general. In other words, and for example, information about a patient does not necessarily need to be inputted into the system as an answer to a question. A user may simply input information about a patient when not prompted. This applies with any medical related information inputted into the system. Another example is that a user may make a medical observation that can be used by the system of the present invention to provide medical information. More particularly, the information may be considered as an answer and inputted into the answers database, patient information database, or any other appropriate database of the system according to the present invention. The medical observation may, for example, be used to provide any kind of medical observation, such as a diagnosis, an indication of a medical procedure recommendation, an indication of a prescription medication recommendation, an indication relating to a test recommendation, an indication relating to a therapy recommendation, or any other medical related information.

After having had the benefit of reviewing this disclosure, the skilled artisan will also appreciate that the present invention contemplates applying rules to any medical related information regardless of the way that the information came to be in the system, i.e., regardless of whether the information was provided as an answer in response to a question, an observation made by a user, or any other way to accumulate medical related information to be used in the system. The present invention also advantageously contemplates that test results may be considered as answers that may be used to provide medical related information to be used in connection with the system according to the present invention. Other information that is contemplated as being used by the system according to the present invention includes medical observations, medical findings, medical conditions, medical diagnoses, or any other related medical information.

As illustrated in FIG. 10, the plurality of medical information databases 104, the patient information database 106, the medical practices database 108, the questions database 110 and the answers database 112 may be stored on a computer readable medium 114. After having had the benefit of this disclosure, those skilled in the art will appreciate that the computer readable medium 114 may, for example, be a disc, or any other computer storage medium capable of being read on a computer 116. The computer readable medium 114 may be loaded onto a computer 116 so that the databases 104, 106, 108, 110, 112 may be accessed using a user interface 118. The user interface 118 illustrated in FIG. 10 is a keyboard to access the computer 116 upon which the interactive protocol system 100 has been loaded. Those skilled in the art, however, will appreciate that the user interface 118 may be provided by any device suitable for accessing the interactive protocol system 100 such as, for example, a personal digital assistant (PDA), a portable computer, or any other type of user interface as understood by those skilled in the art.

As perhaps best illustrated in FIG. 11, the plurality of medical related information databases 104, the patient information database 106, the medical practices database 108, the questions database 110 and the answers database 112 may also be stored on a computer memory, such as, for example, a server 120 that may be accessed by a user using a user interface 118. In the example illustrated in FIG. 11, the user is using a user interface 118 to use a computer 116 to access the interactive protocol system 100 stored on a server 110 through the Internet 122. Those skilled in the art will appreciate, however, that the interactive protocol system 100 may be accessible by a user using a user interface 118 through a global communications network such as, for example, the Internet 122, or any other type of communications network as understood by those skilled in the art.

The medical practices database 108 may include a plurality of protocols. Each of the plurality of protocols may include a different plurality of narrowing questions to be presented to the user. The questions preferably relate to one of the plurality of protocols to be presented to the user, and are based on the answers to the questions provided by the user. The narrowing questions are to be answered by the user to provide the user an indication relating to medical practices. In other words, as the user is using the interactive protocol system 100 of the present invention, plurality of questions may be presented to the user from the questions database 110. The user may be prompted to answer the questions using either answer stored in the answers database 112, i.e., predetermined answers, or may submit customized answers. It is preferable that the customized answers relate to answers stored in the answers database 112, but those skilled in the art will appreciate that a customized answer provided by user may not necessarily relate to a predetermined answer stored on the answers database. Those skilled in the art will also appreciate that a customized answer entered by the user may be added to the answers database 112 so that the customized answer is available for selection in subsequent uses of the interactive protocol system. The interactive protocol system 100 according to the present invention advantageously allows a user to rapidly narrow the vast amount of information contained in the plurality of medical related information databases 104 to more readily provide the user an indication relating to medical practices. Such a system advantageously reduces redundancies and further reduces duplicative efforts on the part of the user.

The indication relating to medical practices provided to the user may, for example, be a diagnoses selected from a plurality of diagnoses stored on one of the plurality of medical related information databases 104. The indication relating to medical practices may also include any number of medical related indications, as understood by those skilled in the art. For example, the indication may include suggested medical treatments, suggested prescription medicines, suggested medical procedures, or any other medial related indications as understood by those skilled in the art.

The plurality of medical related information databases 104 may include medical analysis information used to make medical related decision. The medical related decision may include a prescribed medication, a medical test, a medical procedure recommendation, a medical treatment recommendation, a procedure protocol, prior authorization protocols, disability protocols, medication prior authorization protocols, insurance protocols, hospital standard protocols, or any other medically related decision as would be understood by the skilled artisan after having had the benefit of reading this disclosure. Those skilled in the art, however, will appreciate that this is an exemplary list, and this disclosure is not meant to be limited by this list. Instead, the medical related decision may include any number of medical related decisions. The indication relating to medical practices advantageously provides the user information necessary to make the medical related decision.

More specifically, the indication relating to medical practices may be a medical related decision selected from a plurality of medical related decisions stored on one of the plurality of medical related information databases 104. The medical related decision is preferably based on a comparison of the rules governing medical care stored on one of the plurality of medical related information databases 104 with the answers to the questions provided by the user. In other words, as the user is presented with questions from the questions database 110, and provides answers to those questions (sometimes from the answers database 112), the answers are compared with rules governing medical care that are stored on the medical related information databases 104. As a user is using the interactive protocol system 100, if an answer does not comply with at least one of the rules stored on the medical related information databases 104, then the user may be prompted for an alternate answer. The system of the present invention contemplates that the rules may be any medical related rules. For example, the rules may be insurance reimbursement rules, medical practice rules, medical diagnosis rules, medical procedure rules, medication rules, medical testing rules, medical therapy rules or any other type of medical related rules.

Accordingly, the interactive protocol system 100 of the present invention is not an advisory program, but rather requires the user to meet certain criteria in the form of compliance with rules before proceeding further with medical related decisions. After having had the benefit of this disclosure, however, those skilled in the art will appreciate that a user may override the rules stored on the medical related information databases 104 for any number of reasons. For example, a user may determine that an answer selected from the answers database 112 may be suitable for a new medical treatment that may be available, but that may not necessarily comply with the rules stored on the medical related information database 104. Accordingly, to advantageously advance the practice of medicine, the user may be able to override the rules in to allow for selection of a new medical treatment, or to make any other medical related decision as deemed necessary.

The selected medical related decision may represent one of a plurality of best practices. A best practice may be defined as a best available medical related decision as determined by a medical professional peer, and as updated on the plurality of medical related information databases. A best practice may advantageously provide a medical professional M, or any other user, with the most updated medical related information available so that a user of the interactive protocol system 100 is insured that he or she is not operating using outdated medical related information. The plurality of medical related information databases 104 may be automatically updated with the best practices.

The user may enter patient information into the patient information database 106 responsive to a prompted indication using the user interface 118. The prompted indications may, for example, request patient history information, personal information regarding the patient, insurance information, or any other type of information necessary for the user to make a medical related decision for a particular patient. Those skilled in the art will also appreciate that the present invention contemplates the possibility of importing patient information into the patient information database 106 from an external source. For example, it is contemplated that a patient may seek treatment from a user of the interactive protocol system 100, but may have previously received medical treatment from a medical professional that did not use the interactive protocol system. The patient's medical records, however, may be readily imported into the patient information database 106 so that the user may readily use the interactive protocol system 100 to make a medical decision relating to the patient.

The interactive protocol system 100 according to the present invention also advantageously includes a duplication prevention system 124. After having had the benefit of reading this disclosure, those killed in the art will appreciate that when a patient is in need of several protocols at the same time, different protocols may include common questions. For illustrative purposes only, several different protocols may need a patient's blood pressure, or some other common medical observation to be entered. The duplication prevention system 124 may advantageously prevent presentation of a prompted indication, i.e., a question from the questions database 110, requiring entry of patient information that is currently stored in the patient information database 106. In other words, the duplication prevention system 124 advantageously eliminates the need for a user of the interactive protocol system 100 to enter the same information more than once. For example, when a user is gathering information from a patient in order to make a medical related decision, and engaging in the question and answer system according to the interactive protocol system 100 of the present invention, the duplication prevention system 124 advantageously prevents the presentation of questions requiring a response identical to information already inputted by the user, i.e., patients date of birth, pulse, blood pressure, etc. The duplication prevention system 124 of the interactive protocol system 100 of the present invention advantageously reduces duplication that may be associated with typical medical examinations and, as such, advantageously enhances time savings for the user.

After having had the benefit of this disclosure, those skilled in the art will appreciate that the duplication prevention system 124 according to the present invention does not necessarily prevent duplicate medical information entries from being entered into the system by the user. For example, a medical professional may desire to monitor a patient's blood pressure over time. Such a desire, however, would technically require duplicate entry of the medical related information. Accordingly, the medical professional may have the option of allowing duplicate entries when desirable. Further, the duplication prevention system 124 may be set up to allow for various pieces of medical information to be duplicated, while preventing other pieces of medical information from being duplicated. This advantageously allows the medical professional to customize the duplication prevention system 124 as needed to suit their practice.

Information entered by the user using the user interface 118 may, for example, include medical history information, medication information and insurance information. The information entered by the user may be entered into one of the plurality of medical related information databases 104, or the patient information database 106. Those skilled in the art, however, will appreciate that any other type of medical related information may also be entered by the user using the user interface 118.

A method aspect of present invention is for making a medical related decision using an interactive protocol system 100. The method may include presenting questions to a user from the questions database 110. The method may also include prompting the user for an answer relating to the question, and determining a protocol from amongst a plurality of protocols to be presented to the user based on the answers to the questions. The method may further include presenting the user with additional narrowing questions from the questions database 110 relating to the protocol, and providing the user an indication relating to medical practices based on the answers to the narrowing questions. The indication relating to medical practices may, for example, be a medical related recommendation, a medical procedure a medication to be prescribed, a series of medial related procedures, a medical test or any other type of medical recommendation.

Figure 12:
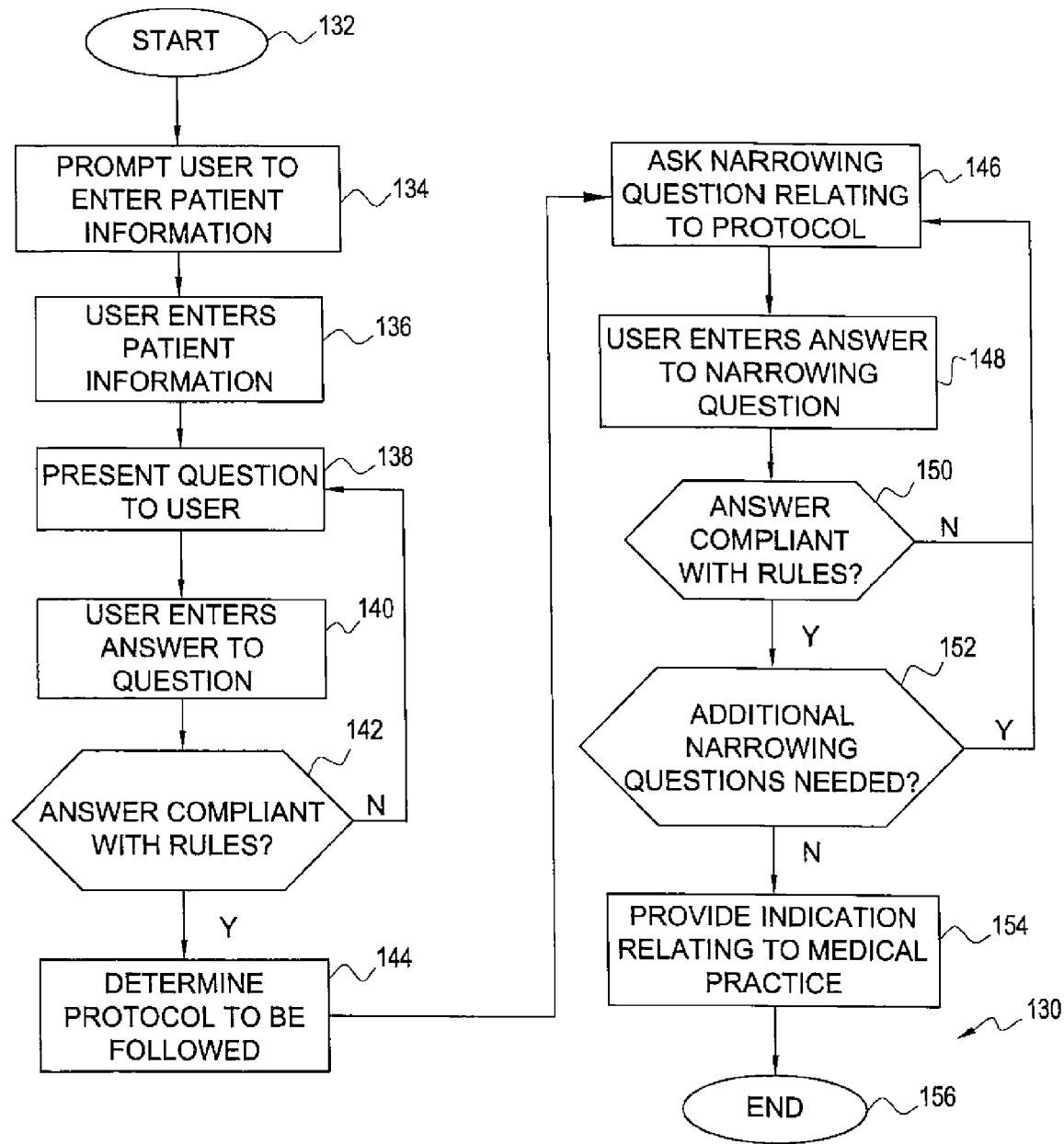
FIGS. 12-15 are flow charts illustrating methods of making a medical decision using the interactive protocol system illustrated in FIGS. 10-11.

Referring now additionally to the flowchart 130 illustrated in FIG. 12, a method aspect of the present invention is now described in greater detail. More specifically, the method illustrated in the flowchart 130 of FIG. 12 is directed to making a medical related decision using the interactive protocol system 100. From the start (Block 132), a user is prompted to enter patient information at Block 134. At Block 136, the user enters the patient information into the patient information database 106. At Block 138, a question from the questions database 110 is presented to the user. The user enters an answer to the question at Block 140. The answer to the question may be selected from the answers database 112, or maybe a customized answer entered by the user.

At Block 142, it is determined whether or not the answer is compliant with one of the rules stored on one of the plurality of medical related information databases 104. Throughout this disclosure, it is to be understood that the rules stored on the plurality of medical related information databases 104 may be any number of rules stored on any number of the medical related information databases. If it is determined at Block 142 that the answer entered by the user at Block 140 is not compliant with one of the rules in one of the medical related information databases 104, then the question from the questions database 110 is again presented to the user at Block 138.

To be more specific, if it is determined at Block 142 that the answer entered by the user at Block 140 is not compliant with one of the rules in one of the medical related information databases 104, then an error message is preferably presented to the user so that the user may be prompted to select another answer to the question presented to the user at Block 138. The error message may, for example, set forth reasons why the answer entered by the user at Block 140 is not in compliance with one of the rules stored on one of the medical related information databases 104. Those skilled in the art will appreciate that the interactive protocol system 100 of the present invention contemplates that an error message need not necessarily be provided to a user if the answer entered to the question at Block 140 is not compliant with the rules stored on one of the medical related information databases 104. Alternately, a user may chose to have all errors presented together at a predetermined time when using the system. For example, it may be preferably for a user to elect to have all errors encountered when using the system presented towards the end of use, i.e., towards the end of the examination of the patient.

Those skilled in the art will also appreciate that if it is determined that the answer entered by the user is not in compliance with one of the rules stored on one of the plurality of medical related information databases 104, the user is preferably prevented from moving forward with the question and answer system. The user may, however, override the error message and move forward. The override capability of the question and answer system advantageously allows the user to select and alternate medical treatment, select an alternate diagnosis, prescribe an alternate medication, or make any number of alternate medical related decisions. This advantageously advances the practice of medicine through new and experimental treatments, for example. It is preferred that if the user overrides an error because an answer entered by the user is not in compliance with one of the rules, that the user enter reasons for overriding the error.

If it is determined at Block 142 that the answer entered by the user at Block 140 is in compliance with one of the rules stored on one of the plurality of medical related information databases 104, then it is determined which protocol is to be followed a Block 144. Those skilled in the art will appreciate that the determination of which protocol to be followed can advantageously be made in an automated fashion by the system or manually by the user. This advantageously provides a user of the system with varying customizable options on how to determine which protocol to follow. At Block 146, after a particular protocol is determined at Block 144, a narrowing question from the questions database 110 is presented to the user relating to the protocol determined at Block 144. At Block 148, the user may enter an answer to the narrowing question presented at Block 146. As described above, the answer entered by the user at Block 148 may be selected from the answers database 112, or maybe a customized answer entered by the user.

At Block 150, it is determined whether the answer to the narrowing question entered by the user at Block 148 is in compliance with one of the rules stored on one of the medical related information databases 104. If it is determined at Block 150 that the answer entered by the user at Block 148 is not in compliance with the rule, then the narrowing question at Block 146 is again presented to the user. Determining compliance of the answer entered by the user at Block 148 with one of the rules stored on one of the medical related information databases 104 is similar as the described above.

If it is determined at Block 150 that the answer entered by the user to the narrowing question at Block 148 is in compliance with one of the rules stored on one of the medical related information databases 104, then it is determined at Block 152 whether additional narrowing questions need to be presented to the user from the questions database 110 in order to provide an indication relating to a medical practice. If it is determined at Block 152 that additional narrowing questions need to be presented to the user from the questions database 110 in order to provide an indication relating to a medical practice, then additional narrowing questions relating to the protocol determined at Block 144 are presented to the user at Block 146. If, however, it is determined at Block 152 that additional narrowing questions are not needed, then an indication relating to a medical practice is provided to the user at Block 154. Thereafter, the method is ended at Block 156.

Figure 13:
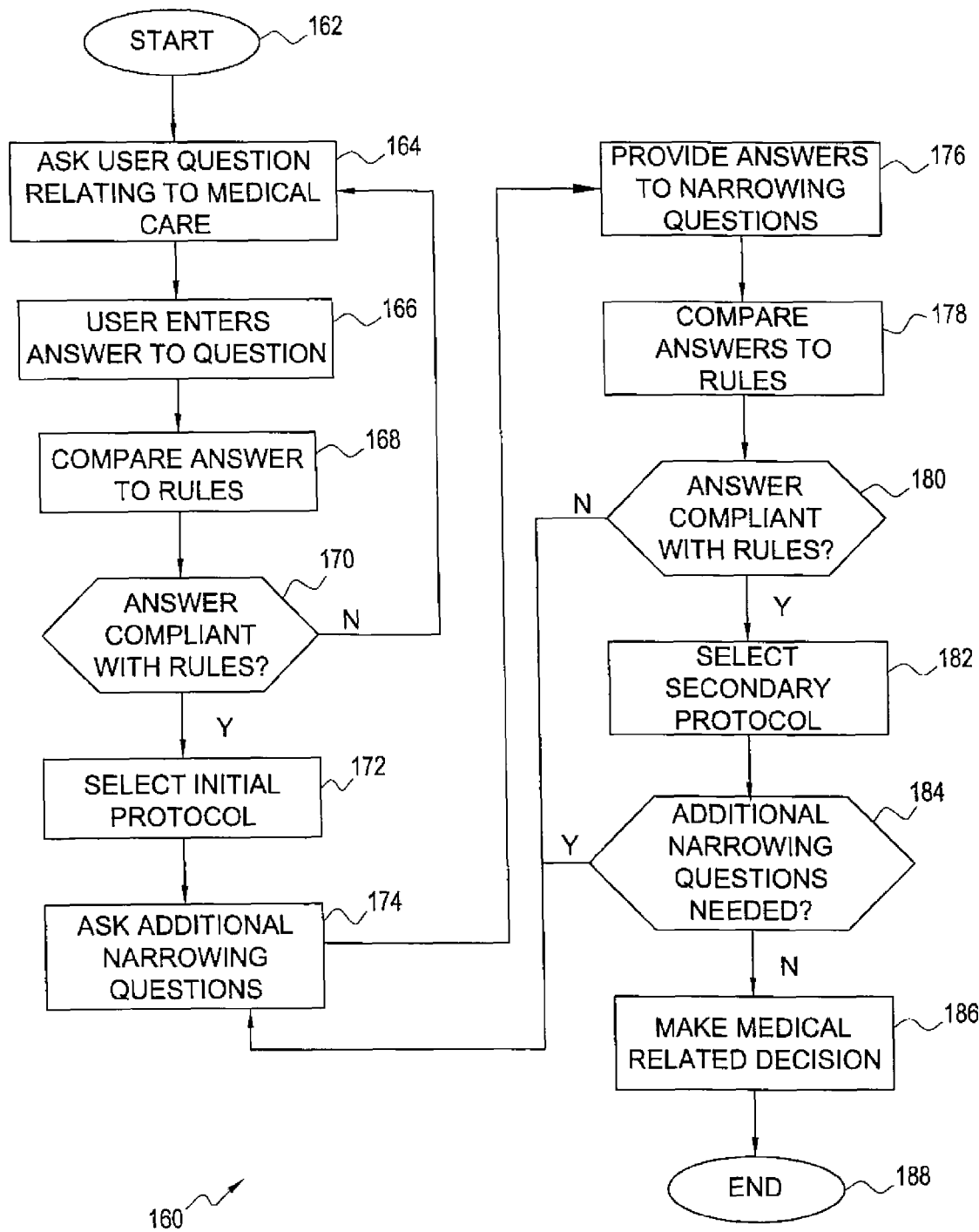

Referring now to the flowchart 160 illustrated in FIG. 13, an additional method aspect of the present invention is now described in greater detail. More specifically, this method aspect of the present invention is directed to using an interactive protocol system 100 to make a medical related decision wherein multiple protocols are used to arrive at the medical related decision. From the start (Block 162), a user is presented a question relating to medical care from the questions database 110 at Block 164. At Block 166, the user may enter an answer to a question presented at Block 164. As described above, the answer may be selected from the answers database 112, or may be a customized answer entered by the user. At Block 168, the answer entered by the user at Block 166 is compared to one of the rules stored on one of the medical related information databases 104. Those skilled in the art will appreciate the rules stored on one of the medical related information databases 104 may be any medical related rule used in making a medical related decision.

At Block 170, it is determined whether the answer entered by the user at Block 166 is compliant with one of the rules stored on one of the medical related information databases 104. If it is determined that the answer entered by the user at Block 166 is not in compliance with one of the rules, then the question is again presented to the user at Block 164. As described above, an error message may be displayed to the user prompting the user to enter another answer to the question from the questions database 110. Throughout this disclosure, those skilled in the art will appreciate that when it is determined that an answer entered by a user is not in compliance with one of the rules stored on one of the medical related information databases 104, an error message may be displayed to the user indicating that the answer entered by the user is not in compliance with one of the rules.

If it is determined at Block 170 that the answer entered by the user at Block 166 is in compliance with one of the rules stored on one of the medical related information databases 104, then an initial protocol is selected at Block 172. At Block 174, additional narrowing questions from the questions database 110 may be presented to the user. At Block 176, answers to the narrowing questions presented to the user from the questions database 110 at Block 174 may be entered by the user at Block 176. At Block 178, the answers to the narrowing questions entered by the user at Block 176 are compared to the rules stored on the medical related information databases 104. At Block 180, it is determined whether or not the answers provided to the narrowing questions at Block 176 are in compliance with the rules stored on the medical related information databases 104. If it is determined that the answer entered by the user at Block 176 is not in compliance with the rules stored on the medical related information databases, then the additional narrowing questions are again presented to the user at Block 174.

If, however, it is determined at Block 180 that the answer entered by the user to the narrowing questions stored on the questions database at Block 176 are in compliance with one of the rules stored on the medial related information databases, then a secondary protocol may be selected at Block 182. At Block 184, it is determined whether additional narrowing questions need to be presented to the user in order for the user to make a medical related decision. If it is determined that additional narrowing questions need to be presented to the user at Block 184, then the user may be presented additional narrowing questions at Block 174. If, however, it is determined that additional narrowing questions do not need to be presented to the user at Block 184, then the user may make a medical related decision at Block 186. The method is thereafter ended at Block 188.

Those skilled in the art will appreciate the use of an initial protocol followed by a secondary protocol. More specifically, when a user initially examines a patient, for example, an initial finding may lead the user to use an initial protocol. Thereafter, during the examination, the user may uncover additional medical related information that can be used to narrow the initial protocol into one of a plurality of sub-protocols, or a secondary protocol. This process can continue, i.e., additional sub-protocols, until the user is able to make the medical related decision.

Figure 14:
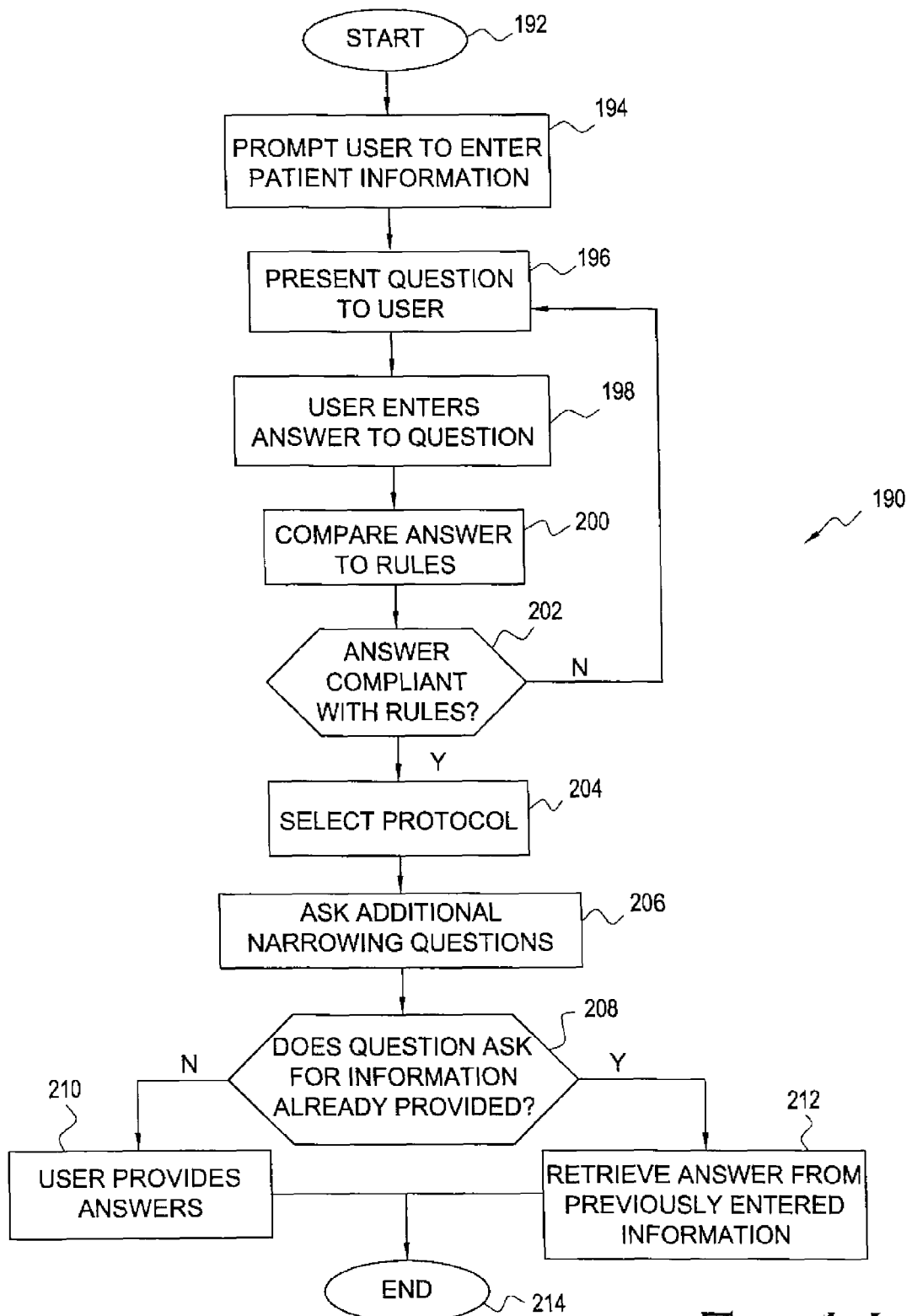

Referring now additionally to the flowchart 190 illustrated in FIG. 14, yet another method aspect of the present invention is now described in greater detail. The method aspect of the invention illustrated in the flowchart 190 of FIG. 14 is directed to use of a duplication prevention system 124 of the interactive protocol system 100 according to the present invention. From the start (Block 192), a user may be prompted to enter patient information at Block 194. The patient information is preferably entered into the patient information database 106. At Block 196, a user may be presented with a question from the questions database 110. The user may enter an answer to the question at Block 198. As described above, the answer may be selected from the answers database 112, or may be a customized answer entered by the user.

The present invention advantageously contemplates, however, that in some instances, it may be desirable for questions to be duplicated. Accordingly, a user may set parameters to ensure that some questions are duplicated and not prevented from being presented by the duplication prevention system 124. For example, a user may use the system over a long period of time, i.e., during a hospital stay of a patient, and may desire to know the blood pressure of the patient over a certain time interval, i.e., every hour. In such a case, it is not desirable for the duplication prevention system to prevent a question relating to the patient's blood pressure from being presented. Therefore, the user may set parameters to allow for duplicate questions to be asked when necessary.

At Block 200, the answer entered by the user at Block 198 is compared with rules stored on the medical related information databases 104. At Block 202, it is determined whether the answer entered by the user at Block 198 is in compliance with the rules. If it is determined at Block 202 that the answer entered by the user at Block 198 is not in compliance with the rules, then the user is again presented with the question at Block 196. If, however, it is determined at Block 202 that the answer entered by the user is in compliance with the rules stored on the medical related information databases 104, then a protocol may be selected at Block 204. At Block 206, additional narrowing questions relating to the protocol selected at Block 204 are presented to the user.

At Block 208, it is determined whether the additional narrowing question presented to the user at Block 206 request information that has already been provided by the user, or that may already exist within the interactive protocol system 100. If it is determined at Block 208 that the narrowing question presented to the user at Block 206 requests duplicative information, then the answers, i.e., the duplicative information, is retrieved from previously entered information at Block 212. If, however, it is determined at Block 208 that the narrowing questions presented to the user at Block 206 do not request duplicative information, then the user may provide an answer to the narrowing questions at Block 210. Those skilled in the art will appreciate that the duplication prevention system 124 according to the present invention does not necessarily require that the question requesting duplicative information be presented to the user. Instead, the question can either be skipped, or may be displayed to the user having the answer already filled in. Thereafter, the method is ended at Block 214.

The interactive protocol system 100 according to the present invention advantageously contemplates providing a protocol for prior authorization for medical related costs, i.e., medical procedures, medical examinations, prescribed medicines, etc. The state of the prior art is cumbersome in that it sometimes involves requiring the medical professional, or the staff of the medical professional, to fill out forms, transmit the forms to the insurance carrier, and await authorization. If authorization is not received prior to the medical related cost being encountered, then it is possible that the patient may not be reimbursed by the insurance company. This scenario, however, assumes that the patient has paid the medical professional and is waiting for the insurance company to provide a reimbursement. Typically, that is not the case. Instead, the medical professionals sometimes advance their services in hopes of being reimbursed by the insurance company. Absent a pre-approval process, however, there generally is no guarantee for payment to the medical professional. Accordingly, using the interactive protocol system 100 according to the present invention to provide pre-approvals of insurance reimbursement is advantageous.

The interactive protocol system 100 may be automated to accomplish this process. More particularly, the interactive protocol system 100 according to the present invention may be positioned in communication with the rules database, which may include insurance related rules carried thereon. The insurance related rules may, for example, be directed to rules governing reimbursement of a medical related cost to be encountered by the medical professional, the patient or both.

One contemplated method of operation of the insurance reimbursement aspect of the interactive protocol system is to provide an authorization number pursuant to information received from the medical professional. For example, the medical professional may conduct an examination of the patient and determine that it is appropriate to prescribe a particular medication to a patient. The medical professional may, for example, engage in the question and answer format described above to come to the conclusion that the patient has a particular diagnosis, and that it is appropriate to treat the patient with a particular medication. After the medical professional has entered the information into the system, the rules engine determines if the medication prescribed by the medical professional meets the requirements of the rules relating to insurance reimbursement.

If the proposed medication to be prescribed does not meet the minimum requirements for the rules relating to medical reimbursement, then the medical professional is provided with an indication that the proposed prescribed medication is not pre-approved. After having had the benefit of this disclosure, those skilled in the art will appreciate that this does not prevent the medical professional from prescribing the medication, but rather provides an early indication to both the medical professional and the patient that the proposed prescribed medication will not be covered by insurance. If, however, the proposed prescribed medication does meet with the minimum requirements outlined by the rules relating to medical reimbursement, then the medical professional may, for example, be provided with an authorization code.

The interactive protocol system 100 according to the present invention contemplates that the patient may use the authorization code provided to the medical professional to obtain the medication. In other words, the system may provide the authorization code to the medical professional provided that the information entered by the medical professional is in compliance with the rules relating to insurance reimbursement, and the medical professional may thereafter provide the authorization to the patient evidencing that the prescribed medication has been approved for medical reimbursement.

The rules relating to insurance reimbursement may take several factors into account and may vary from patient to patient. Of course, one of the biggest factors that may be taken into account is the level of medical insurance that the patient carries. Another factor that is likely to be considered, in the example of a prescribed medication provided above, is an analysis of the type of medication being prescribed.

The interactive protocol system 100 also contemplates providing the medical professional with the ability to override an indication of non-approval of insurance reimbursement. The override capability may provide the medical professional with the ability to enter a reason why the negative indication was provided by the system. The system 100 may compare the reason entered by the medical professional against a list of approved override reasons, for example, or may take the override under consideration. From the perspective of automation and ease of use, however, it is preferred that the system 100 provides a response and an authorization code to the medical professional in response to the override with as little human intervention as possible.

In the case of an override issued by the medical professional that requires human intervention, i.e., review by a person at the insurance company, and the override is approved, the interactive protocol system 100 according to the present invention contemplates that the approved override may become a rule. Accordingly, this advantageously decreases the need for duplication of efforts with respect to human intervention to analyze and make determinations on overrides issued by the medical professional, thereby minimizing the time necessary for an override to be approved, or for an authorization code to be received.

Although the above provides an example directed to prescribing medication, those skilled in the art will appreciate that the system may be used to obtain insurance reimbursement pre-approval for any medical related cost. For example, the interactive protocol system 100 may be used to obtain insurance pre-approvals for issuing orders for durable medical equipment, issuing referrals for physical therapy, performing a medical procedure, or any other medical related cost.

Figure 15:
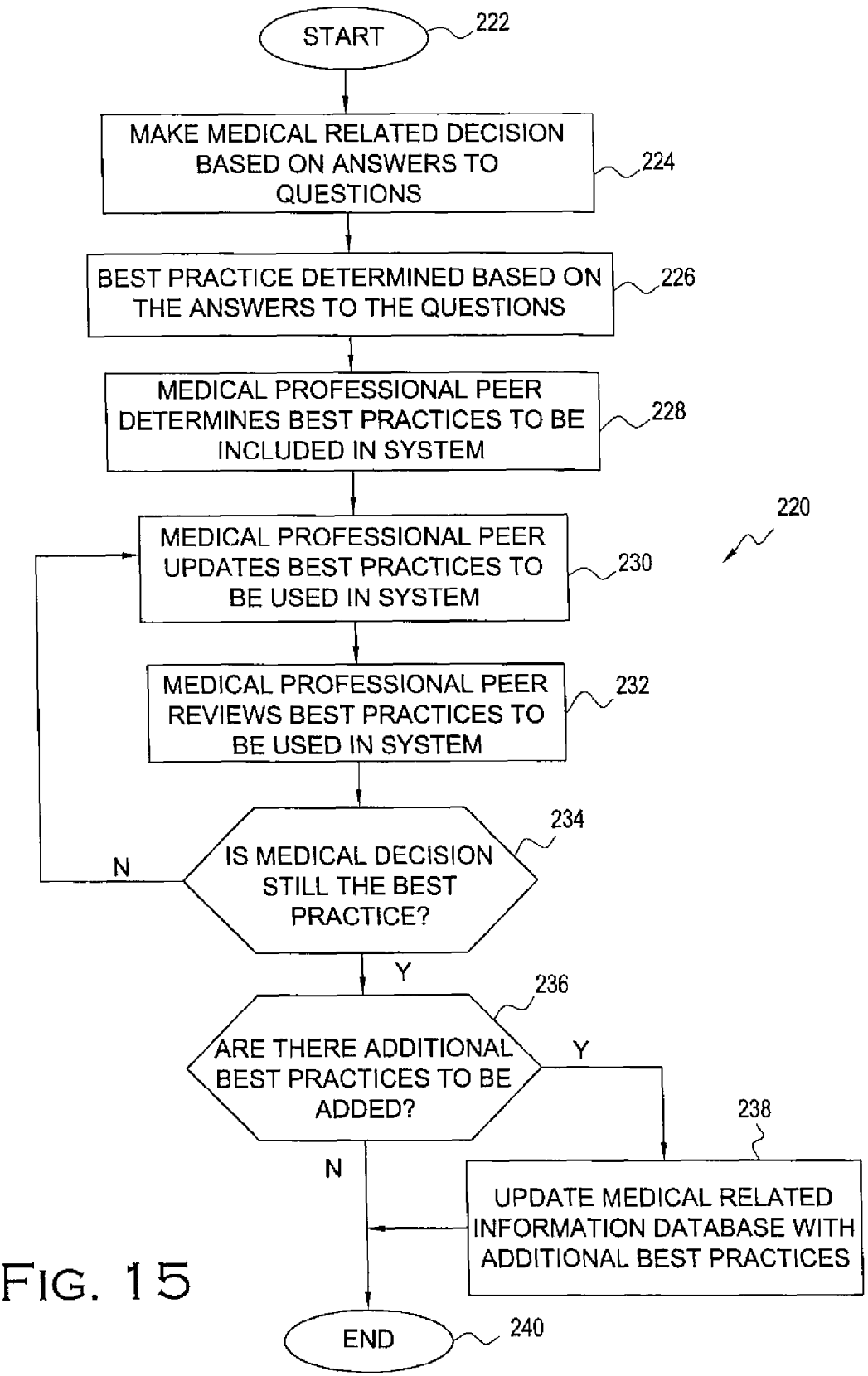

Referring now additionally to the flowchart 220 illustrated in FIG. 15, still another method aspect according to the present invention is now described in greater detail. The method aspect of the invention illustrated in FIG. 15 is directed to determining a best practice, as defined above. More specifically, the method aspect of the invention illustrated in FIG. 15 is directed to determining how medical practices are included on the system as best practices and further includes the method in which a medical professional peer decides whether or not a best practice is updated.

From the start (Block 222), a medical related decision is made by the medical professional based on answers to questions at Block 224. For example, and as illustrated in FIG. 14 and discussed above, the medical professional, or user, may make a medical related decision based on answers to questions entered by the user. At Block 226, a best practice directed to the medical related decision is determined based on the answers to the questions. In other words, the best practice relating to the medical related decision made at Block 224 is made based on the answer to the questions. At Block 228, a medical professional peer may determine what a best practice is to be defined as. More particularly, at Block 228, a medical professional peer determines which medical practices should be considered best practices and, as such, be included on the system.

At Block 230, the medical professional peer may update the best practices to be included in the system, and at Block 232, the medical professional peer may review the best practice to be included in the system. At Block 234, it is determined whether or not the medical decision made by the user is still considered a best practice. If it is determined at Block 234 that the medical decision made by the user at Block 224 is not a best practice, then the medical professional peer may update the best practice at Block 230. If, however, it is determined at Block 234 that the medical decision made by the user is a best practice, then it is determined at Block 236 whether or not additional best practices need to be added to the interactive protocol system 100. If it is determined at Block 236 that additional practices need to be added to the system 100, then the medical related information databases 104 may be updated with additional best practices at Block 238. Thereafter, the method is ended at Block 240.

The process of including medical professional peers in reviewing and adding best medical practices to be included in the system is advantageous for many reasons. For example, using medical professional peers to review and add best medical practices ensures a certain level of reliability in the best practice. The review of the best medical practices conducted by the medical professional peer also ensures that the most up to date medical practices are included on the system. The use of medical professional peers also allows for a user to select from a variety of protocols based on, for example, the author, reputation of an institution updating the best practice, the number of users using a particular protocol, a protocol rating, or any number of other factors. Accordingly, the best practices module of the present invention advantageously provides a great deal of information relating to each protocol. Once a user selects the protocol to be used, the rules contained in the databases may be run against the protocol again. This is advantageous as different rules may apply to different protocols. It is to be understood that the rules, as mentioned above, relate to any number of medical related aspects, such as, for example, medications, procedures, insurance regulations, suggested treatments, or any other number of medical related aspects as understood by those skilled in the art. Rules relating to the best practices may, for example, be determined by the medical professional peer selecting the best practice to be included on the system. Rules relating to insurance reimbursement matters may, for example, be determined by insurance companies.

Figure 16:
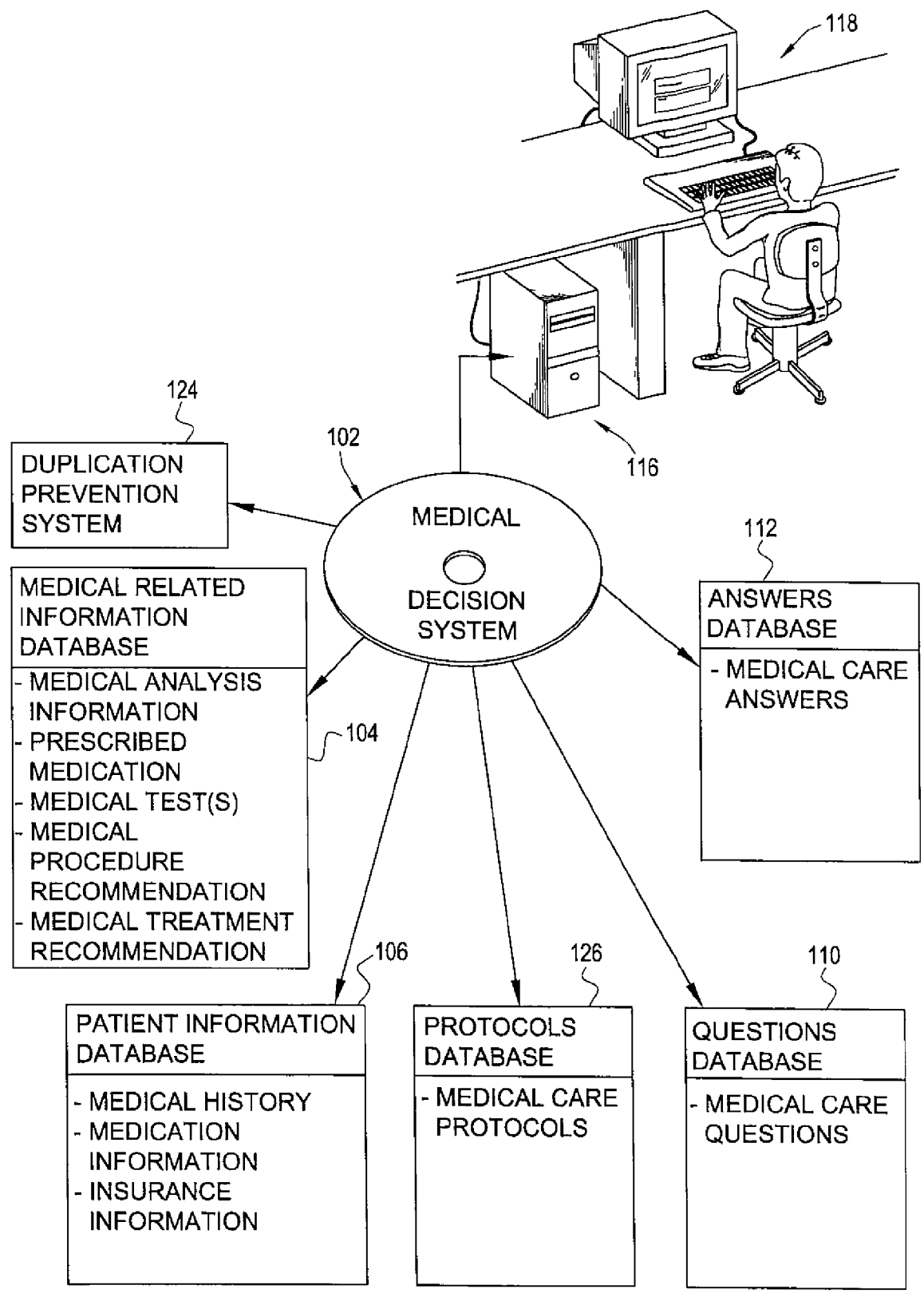
FIGS. 16-17 are schematic views of a medical decision system wherein a questions database and answers database cross reference a medical related information database to provide a user a plurality of protocols relating to a selected medical condition.
Figure 17:
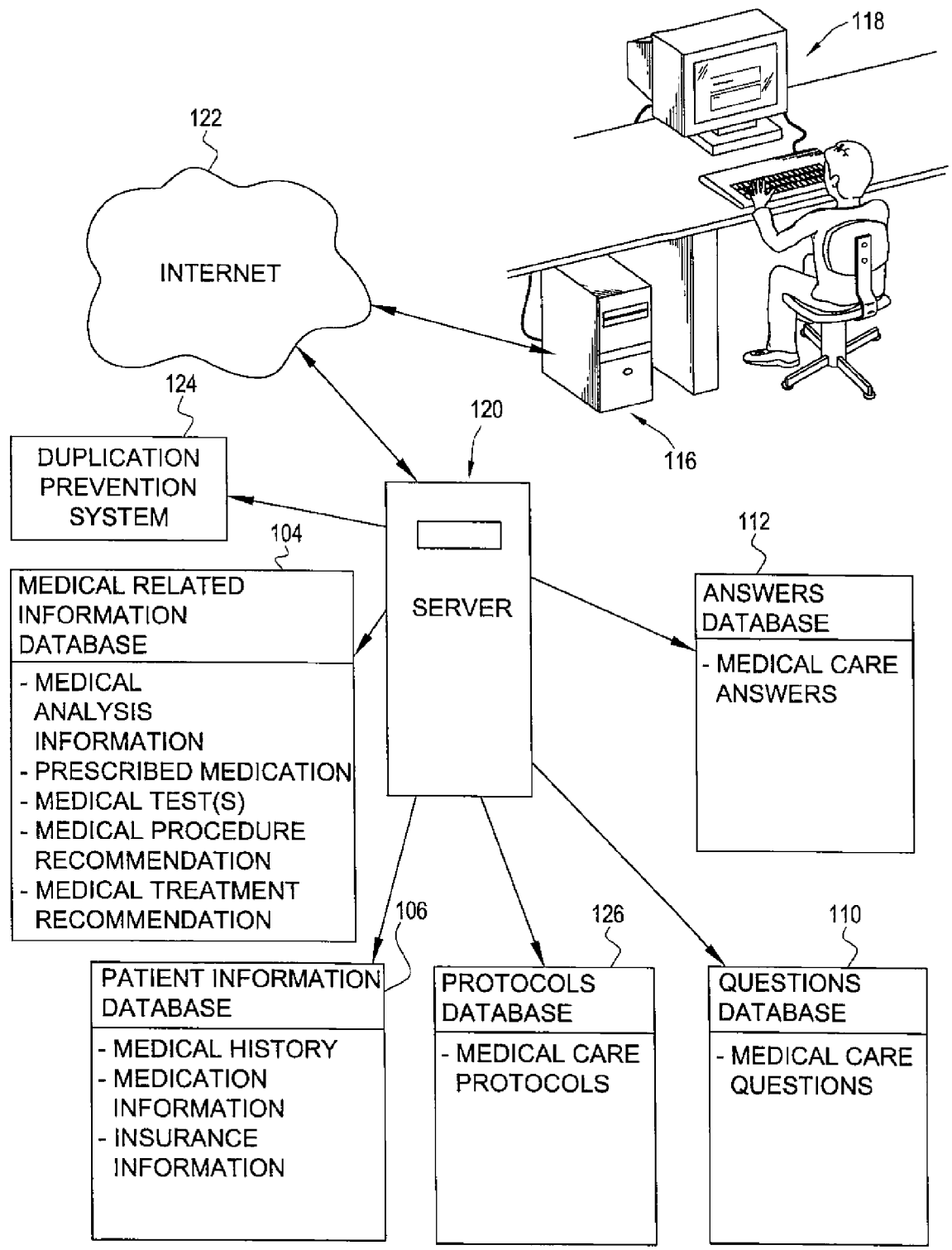

Referring now additionally to FIG. 16-17, additional features of a medical decision system 102 according to the present invention are now described in greater detail. The medical decision system 102 illustrated in FIG. 16-17 may include a patient information database 106 including patient information. The present invention, however, contemplates that the patient information database 106 may be optional and that the system may fully function to allow a user to make a medical decision without need of the patient information database. To be specific, the patient information database 106 me be considered an added feature to the medical decision system 102 according to the present invention in that it is not necessary for the user to make the medical decision. Instead, the patient information database may be used to customize a medical decision to the information in the patient information database. For example, the medical decision system 102 according to the present invention is intended to provide a user with all possible medical recommendations for a selected medical decision. After viewing all possible medical recommendations for a selected medical decision, the user may compare all the medical recommendations to the information in the patient information database 106 to eliminate some of the medical recommendations from consideration. As a specific example, a user may select a medical condition that has multiple types of medical recommendations associated therewith, some of which may be age specific, i.e., some medical recommendations may be appropriate for a geriatric patient, while other medical recommendations may be appropriate for pediatric patients. In that case, the user may enter patient information relating to the patient's age as retrieved form the patient information database, and the recommendations associated with the selected medical condition may be narrowed to the recommendations that are appropriate for the patient.

The medical decision system 102 also includes a questions database 110 including a plurality of questions to be presented to a user relating to medical care. The medical decision system 102 according to the present invention further includes an answers database 112 including a plurality of answers relating the plurality of questions in the questions database 110. Those skilled in the art will appreciate that the answer may be selected from the answers database 112, or may be a customized answer entered by the user. In a case where a user enters a customized answer, the customized answer may thereafter be included as a part of the answers database 112. In other words, the answers database 112 may be updated with new customized answers entered by the user. This advantageously allows the medical decision system 102 according to the present invention to be more customized to the user's needs. The answers in the answers database 112 related to the selected medical condition. In other words, the answer to the question may be the selected medical condition, or may, for example, be a code relating to the medical condition to be selected, as understood by those skilled in the art, after having had the benefit of this disclosure.

The medical decision system 102 also includes a plurality of medical related information databases 104. The plurality of medical related information databases 104 may include medical related information and rules governing medical care. The medical related information included in the medical related information databases 104 may include a plurality of medical conditions to be presented to the user for selection based on the answers to the questions from the questions database 110 selected by the user. Each of the plurality of medical related information databases are preferably in communication with one another. The medical related information databases 104 may also include the plurality of medical recommendations to be presented to the user based on the selected medical condition. The medical recommendations can, for example, be any type of recommendation that may relate to the selected medical condition. This can range from a test, to a procedure, to a lifestyle change, i.e., quit smoking, lose weight, etc., to medication, or any other type of recommendation as understood by those skilled in the art having had the benefit of this disclosure.

The medical decision system 102 may also optionally include a protocols database 126 including a plurality of protocols to be presented to the user. The plurality of protocols preferably relate to the medical condition selected by the user. Those skilled in the art that have had the benefit of this disclosure will appreciate that protocols relate to specific medical conditions, and provide guidelines relating to a medical related decision made by a user. More particularly, a protocol can include information relating to compliance with a prior authorization according to an insurance reimbursement guideline, for example. Further, the protocol may also include information relating to compliance with respect to a procedure, medication, admission or discharge to or from a medical facility, disability benefits, authorizations, etc.

The medical decision system 102 according to the present invention is fully operational and functional without use of the protocols database 126 and the protocols database is intended as an added feature that may optionally allow a user to narrow the medical recommendations based on a comparison of the selected medical condition with a particular protocol. For example, a user may select a medical condition and may compare that medical condition against a hospital protocol. That hospital protocol may eliminate some of the medical recommendations from consideration. In that case, the protocol selected by the user acts as a rule to be run against the medical recommendations. The use of rules with this medical decision system 102 will be discussed in greater detail below.

The patient information database 106 (when used), the questions database 110, the answers database 112, the plurality of medical related information databases 104 and the protocols database 126 (when used) are in communication with one another. As illustrated in FIG. 16, the databases 104, 106, 110, 112, 126 may be stored on a computer readable medium which may be readily used on a computer, and accessed by a user using a user interface 118. Those skilled in the art will appreciate that the computer readable medium may, for example, be a disc, a pin drive, a USB device, or any other medium capable of being read by a computer. As perhaps best illustrated in FIG. 17, the databases 104, 106, 110, 112, 126 may also be stored on a computer memory, such as a server 120, for example. A user may advantageously access the medical decision system 102 using a user interface 118, such as a computer 116, for example, via a global communications network, such as the internet, for example.

The questions database 110 and the answers database 112 advantageously cross-reference the medical related information in the plurality of medical related information databases 104 to present the plurality of medical recommendations relating to the selected medical condition to the user. More specifically, after a user selects a medical condition from among a plurality of medical conditions stored on one of the plurality of medical related information databases 104 based on the answers to the questions selected by the user from the answers database 112, or, after a user enters a medical condition in response to a question, all medical recommendations relating to the selected medical condition are presented to the user.

The medical recommendations on the plurality of medical related information databases 104 advantageously relate to the selected medical condition and provide the user with medical recommendations that can be followed when dealing with the selected medical condition. As briefly discussed above, the medical recommendations can include any recommendation that may relate to a selected medical condition. This is not meant to be a limiting term, but rather an inclusive term of any type of recommendation that can be provided with respect to a selected medical condition.

The medical recommendations may, for example, include treatment plans, or any other information that may guide a decision and criteria regarding a diagnosis, management and treatment of a specific area of healthcare. Those skilled in the art will appreciate that the protocols preferably identify, summarize and evaluate the best evidence and most current data regarding prevention, diagnosis, prognosis, therapy including dosage of medications, risk/benefit and cost effectiveness in all related fields of healthcare, and that different medical recommendations may be used with respect to different protocols to achieve various goals with respect to a selected medical condition.

The system according to the present invention advantageously contemplates that a user may arrive at a selected medical condition upon engaging in the question and answer procedure described above. The present invention also contemplates that a selected medical condition may be selected by a user at any time. The rules component of the medical decision system 102 according to the present invention may be used to prevent a user from finalizing a selected medical decision until a rule has been complied with. In other words, a user may select a medical condition, but the system of the present invention may determine that the selected medical condition is not in compliance with the rules governing medical care. In such a case, an error message may be presented to the user. If, however, it is determined that the rules governing medical care have been complied with, then the selected medical condition may be finalized. The rules aspect of the medical decision system, however, is an optional one. The medical decision system according to the present invention may be fully functional and may present the desired medical recommendations to the user regardless of whether the rules governing medical care are followed.

Upon selection of the medical condition by the user, the present invention contemplates that all medical recommendations relating to the selected medical treatment should be presented to the user. Accordingly, it is desirable for the medical recommendations to be routinely updated so that the most up to date and available medical recommendations may be presented to the user. All of the medical recommendations may not be suitable for each patient and, as such, the system according to the present invention contemplates cross referencing all of the available medical recommendations with information in the patient information database to eliminate, or limit presentation of, some of the medical recommendations. For example, if a patient is a pediatric patient, upon cross referencing the available medical treatments with the patient information database, all treatments for adults may be eliminated. Also for example, medical recommendations that are not covered by a patient's insurance may also be eliminated.

The rules engine of the medical decision system 102 according to the present invention may also be used to narrow the number of medical recommendations presented to the user that relate to the selected medical condition. More specifically, at least one rule can be applied to the medical recommendations presented to the user to limit the number of medical recommendations presented to the user. The application of the at least one rule can occur prior to presenting the user with the plurality of medical conditions, or after displaying the plurality of medical recommendations to the user. For example, a user may select a medical condition and the system may display all the medical recommendations available for the selected medical condition. Thereafter, the system may prompt the user to enter a rule to be applied to the selected medical treatment. Upon selection of a rule, the list of possible medical recommendations may be narrowed to those that are in compliance with the rules. The system according to the present invention also contemplates that the rules may be applied prior to displaying any of the medical recommendations to the user. For example, the user may select a medical condition, as well as the rule, and only the medical recommendations applying to the selected medical condition and in compliance with the rules may be displayed to the user. Accordingly, the medical decision system 102 according to the present invention advantageously allows a user several different options to view all medical recommendations relating to a selected medical condition.

The rules that may be applied to the selected medical condition may, for example, be an insurance rule, an insurance reimbursement rule, medical practices rules, medical diagnosis rules, medical procedure rules, medication rules, testing rules, a patient information rule, a healthcare provider rule, a medical facility rule, a medical society rule, a regulatory rule, a medical therapy, and an evidence based rule. For exemplary purposes, the insurance rule may be used to filter medical recommendations that are not accepted by a particular insurance. Similarly, the insurance reimbursement rule may be used to filter medical recommendations that will not be paid, either fully, or by a percentage amount, by an insurance company. In other words, any of the rules based above can be used to minimize, filter, reduce or organize the medical recommendations presented to the user based on the selected medical condition.

The present invention contemplates that more than one rule may be applied to the results presented to the user. More specifically, a user may apply one of the above referenced rules to the medical recommendations presented relating to the selected medical condition. If the user desires, the user may further limit the results by applying one or more additional rules to the results in order to further narrow the number of medical recommendations presented relating to the selected medical condition.

The present invention also advantageously contemplates an organizational element based on any number of factors. The organizational element according to the present invention advantageously allows all the medical recommendations displayed to the user to be displayed in any order based on various factors. The factors that can be used to organize the medical recommendations may, for example, be the rules described above. These factors may be weighed so that a combination of factors may be taken into account when showing the medical recommendations to the user. For example, it may be desirous to relate each of the medical recommendations to insurance carriers to make the medical recommendations insurance specific, i.e., for every medical recommendation selected, the insurance carrier that covers that particular medical recommendation may also be displayed adjacent thereto. Accordingly, the medical professional can sort the medical recommendations by insurance carrier. This advantageously provides the user with filtering capabilities so that the user may filter out medical recommendations that are not covered by a patient's insurance carrier. Other factors that can be used to organize the medical recommendations displayed to the user may, for example, include the patient's age, medical history, patient's gender, religious beliefs (some religions do not allow for certain medical treatments), or any other number of factors that will be appreciated by those skilled in the art after having had the benefit of reading this disclosure.

The present invention contemplates, however, that it may be desirous to show all available medical recommendations and allow a user to limit the medical recommendations based on predetermined parameters. This advantageously allows a user to present a medical recommendations that may not be covered by the patient's insurance, for example, to the patient in the case where the patient wishes to pay for the medical recommendation outside of the insurance. There may be several other ways that will be understood by one having skill in the art after having had the benefit of this disclosure in which to limit the number of treatments presented to the user. Accordingly, the present invention contemplates using filtering capabilities to filter the number of medical recommendations that may be used and/or available relating to the selected medical condition.

Many protocols may place treatment alternatives into different classes to help a user in deciding which recommendation to use. The goal of the protocols is to standardize medical care, to raise quality of medical care, and to reduce risk to the patient, healthcare provider, and medical insurer. The protocols also advantageously assist the user in achieving a balance between cost and medical parameters such as, for example, effectiveness, specificity, sensitivity, etc. Another advantage of the protocols is that they may be used to show results that other medical professionals have had when using the protocol in a similar situation. The protocols may advantageously provide a user with a check list of recommended procedures based on the selected medical condition. Those skilled in the art, having had the benefit of this disclosure, will appreciate that a recommended procedure is an exemplary term and it not meant to be limiting. Instead, a procedure can include, for example, instructions, such as medical risk management, tests, medication, operations, or any number of medical related procedures, or orders, for example, as understood by those skilled in the art.

As discussed above, the plurality of medical related information databases 104 may include medical analysis information used to make a medical related decision. The medical related decision may include a medical condition determination, a prescription medication, a medical test, a medical procedure recommendation and a medical treatment recommendation. Those skilled in the art will appreciate that all of these medical related decisions may have medical recommendations and protocols associated therewith. The medical recommendations associated with these medical related decisions may be stored on one of the plurality of medical related information databases 104 and the protocols associated with these medical related decisions are stored on the protocols database 126 for use by the user.

The medical related information databases 104 may be updatable by the user with new medical recommendations not previously presented to the user. Further, the plurality of medical recommendations presented to the user from the medical related information databases may be based on a comparison of the rules with the answers to the questions and the selected medical treatment. The plurality of medical recommendations may be automatically updated by a medical professional peer. These medical recommendations may be considered verified medical recommendations upon confirmation by a medical professional peer or a system administrator, or through another process to verify that the medical recommendation is a valid one with respect to the selected medical treatment.

The protocols database 126 may be updateable by the user with new protocols. More specifically, a new protocol may be defined by a protocol that was not presented to the user when the plurality of protocols are presented based on the medical condition selected by the user. The new protocol may be defined as a verified protocol. A verified protocol is preferably reviewed and approved by at least one system administrator. Those skilled in the art will appreciate that, similar to the best practices described above, the verified protocols may be reviewed by medical professional peers. In some instances, a protocol reviewing committee may review protocols to ensure that protocols remain verified. For example, there may be cases where a protocol may include a treatment that becomes outdated. In such a case, a protocol reviewing committee may decide to delete such a protocol, or may provide an indication to a user that the protocol may include a treatment parameter that is considered outdated.

Protocols are meant to refer to a code or correct conduct relating to various medical practices. These may, for example, include safety protocols and academic protocols. A protocol may include a predefined written procedural method to establish standards that can be adequately assessed by peer review and provide for successful replication or results by others in the field. A protocol may also include a rule, guideline, or document which guides how an activity can or should be performed. Protocols can be used to guide a medical professional, inform a medical professional of standards, determine if a standards are being followed, or inform a medical professional of medical practices that others have engaged in with respect to similar medical scenarios. Protocols may also inform medical professionals of historical outcomes of various choices within a protocol and may inform a medical professional of new and available medical practices and procedures.

Protocols may further be used to describe all available options for a diagnosis and identify a subset of choices based on specific characteristics of the patient. There characteristics may be pointed out to the medical professional by highlighting the characteristics, showing them in a different color, display them in order of specificity, sensitivity, outcome, contractual agreement fees, reimbursements, costs, or any other number of factors as understood by those skilled in the art.

Protocols may further be used to coordinate care amongst various medical departments, providers and other medical related personnel. The protocol system as described in the present invention advantageously ensures that the level of care provided to patients is appropriate. More particularly, when a medical professional needs to interact with a patient, the system according to the present invention is preferably accessed by the user via a computer so that it can be determined whether or not the level of care being provided to the patient is appropriate for the service that is being provided.

The protocol system according to the present invention also advantageously ensures that certain tasks relating to medical treatment are performed in a specific order. When adding a new protocol to the system, a user has the option of completing the information necessary before it is added to the protocol on the system. The user may also add information to the protocol directly before compiling a large amount of information, i.e., add each individual piece of information to the protocol separately. These options advantageously ensure that no duplicity takes place when revising or updating a protocol.

Those skilled in the art will appreciate that the medical decision system 102 may include a protocol verification system. The protocol verification system may operate in any number of ways to verify existing protocols, to review existing protocols, or to verify new proposed protocols. The medical decision system 102 according to the present invention contemplates the possibility that the protocol verification system may be updated with medical related information directed to outdated medical procedures, tests, medications, or any other type of medical related information. This outdated medical information may be cross-referenced against the protocol stored in the protocols database 126. Thereafter, protocols stored on the protocols database 126 that have been identified as including outdated medical information may be flagged for review by a system administrator or a medical professional peer. Alternately, the identified protocols including the outdated medical information may be automatically removed from the protocols database 126 or may be automatically updated with new medical information.

The plurality of protocols presented to the user from the protocols database 126 may be based on a comparison of the rules governing medical care stored on one of the plurality of medical related information databases 104 with the answers to the questions in the questions database 110 as provided by the user. As described in great detail above, the comparison of the answers to the rules during the question and answer process engaged in by the user when using the medical decision system 102 advantageously ensures that the user makes a proper medical decision, and that an appropriate protocol is selected based on that properly made medical decision.

A method aspect of the present invention may be for making a medical related decision using a medical decision system including a questions database, an answers database and a plurality of medical related information databases including rules governing medical care, a plurality of medical conditions, and medical recommendations relating to the plurality of medical conditions. Each of the questions database, answers database and plurality of medical related information databases may be positioned in communication with one another and stored on at least one of a computer readable medium and a computer memory. The method may include presenting a user with at least one question relating to medical care and prompting the user for an answer relating to the at least one question. The answer preferably relates to selection of a medical condition. The method may further include presenting the user with all the medical recommendations relating to the selected medical condition.

Another method aspect of the present invention is also for making a medical related decision. The method may include prompting a user to select a medical condition stored on at least one of the plurality of medical related information databases and presenting the user with all medical recommendations relating to the selected medical condition from the medical related information databases. Each of the medical recommendations is preferably considered an acceptable medical recommendation relating to the selected medical condition. The method may further include automatically updating the medical recommendations by a medical professional peer. The medical recommendations may be defined by a respective plurality of medical recommendations available to be selected by the user and relating to the medical condition determined by the user.

Still another method aspect of the present invention is for making a medical related decision using the medical decision system 102 according to the present invention. The method may include presenting a user with a question from the questions database 110 relating to medical care. The method may also include prompting the user for an answer relating to the question. The answer may be stored on the answers database 112, or, as described above, may be a customized answer entered by the user. The method may further include prompting the user to select a medical condition from the plurality of medical conditions stored on one of the plurality of medical related information databases 104. The medical condition may be selected by the user based on a comparison of the rules governing medical care stored on the medical related information databases 104 with the answers relating to the question. The method may still further include presenting the user with a plurality of protocols from the protocols database 126.

Figure 18:
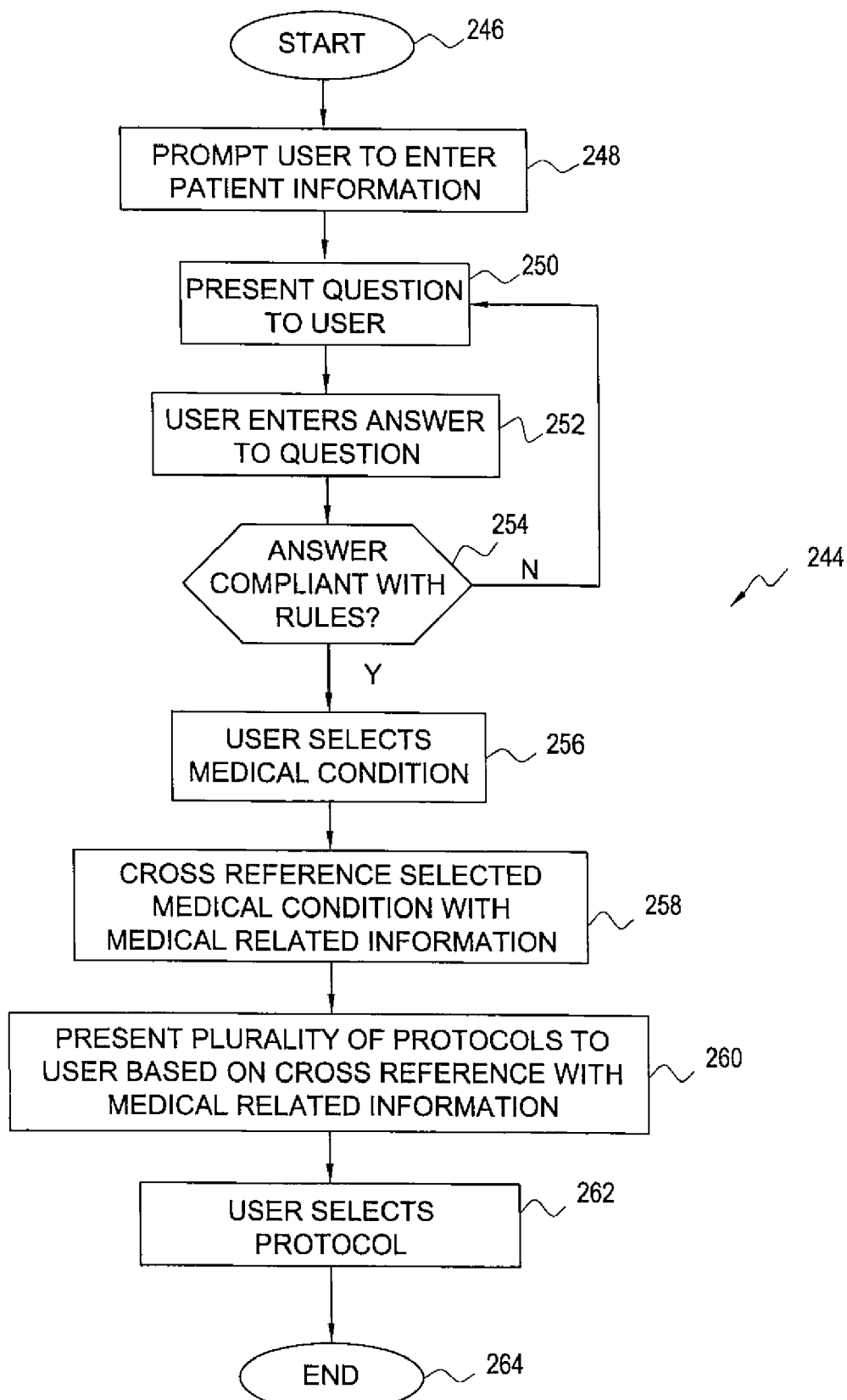
FIGS. 18-20 and 18A-20A are flow charts illustrating methods of making a medical decision according to the present invention.

Referring now to the flowchart 244 of FIG. 18, another method aspect of the present invention is now described in greater detail. The method aspect illustrated in the flowchart 244 of FIG. 18 is directed to using a medical decision system 102 to make a medical related decision. From the start (Block 246), the user may enter patient information at Block 248. At Block 250, a question may be presented to the user from the questions database 110. At Block 252, the user may enter an answer to the question presented at Block 250. As described above, the user may select the answer at Block 252 from the answers database 112, or may enter a customized answer.

At Block 254, it is determined whether or not the answer entered by the user at Block 252 is compliant with one of the rules stored on the medical related information databases 104. If it is determined at Block 254 that the answer entered by the user at Block 252 is not in compliance with one of the rules stored on one of the medical related information databases 104, then the user is again prompted with the question at Block 250.1f, however, it is determined at Block 254 that the answer entered by the user at Block 252 is compliant with one of the rules stored on one of the medical related information databases 104, then the user may select a medical condition at Block 256. At Block 258, the selected medical treatment may be cross-referenced with the medical related information in the medical related information databases 104.

In some cases, a medical condition may have already been established for a patient. As such, a medical professional select a protocol to be completed based on the medical condition that has already been established. This can occur after the patient has been identified as a patient having an established medical condition, which may, for example, be based on the answers to the previously presented questions. In either a case where a patient has an established medical condition, or a medical condition is selected by the user based on the questions and the answers to the questions, the user may be presented with a plurality from the protocols database 126 based on the comparison of the selected medical condition with the medical related information in the medical related information databases 104 at Block 260. At Block 262, the user may select one of the protocols from the protocols that were presented to the user at Block 260. The method is ended at Block 264.

Those skilled in the art will appreciate that the protocol selected by the user at Block 262 may, for example, be a primary, or an initial, protocol. It may be necessary for the user to select a secondary protocol depending on additional cross-referencing of the selected medical condition with medical related information stored in the medical related information databases 104. More particularly, a user may select as many protocols as necessary to narrow the medical related information to thereby allow the user to make a more concise medical related decision.

Figure 18A:
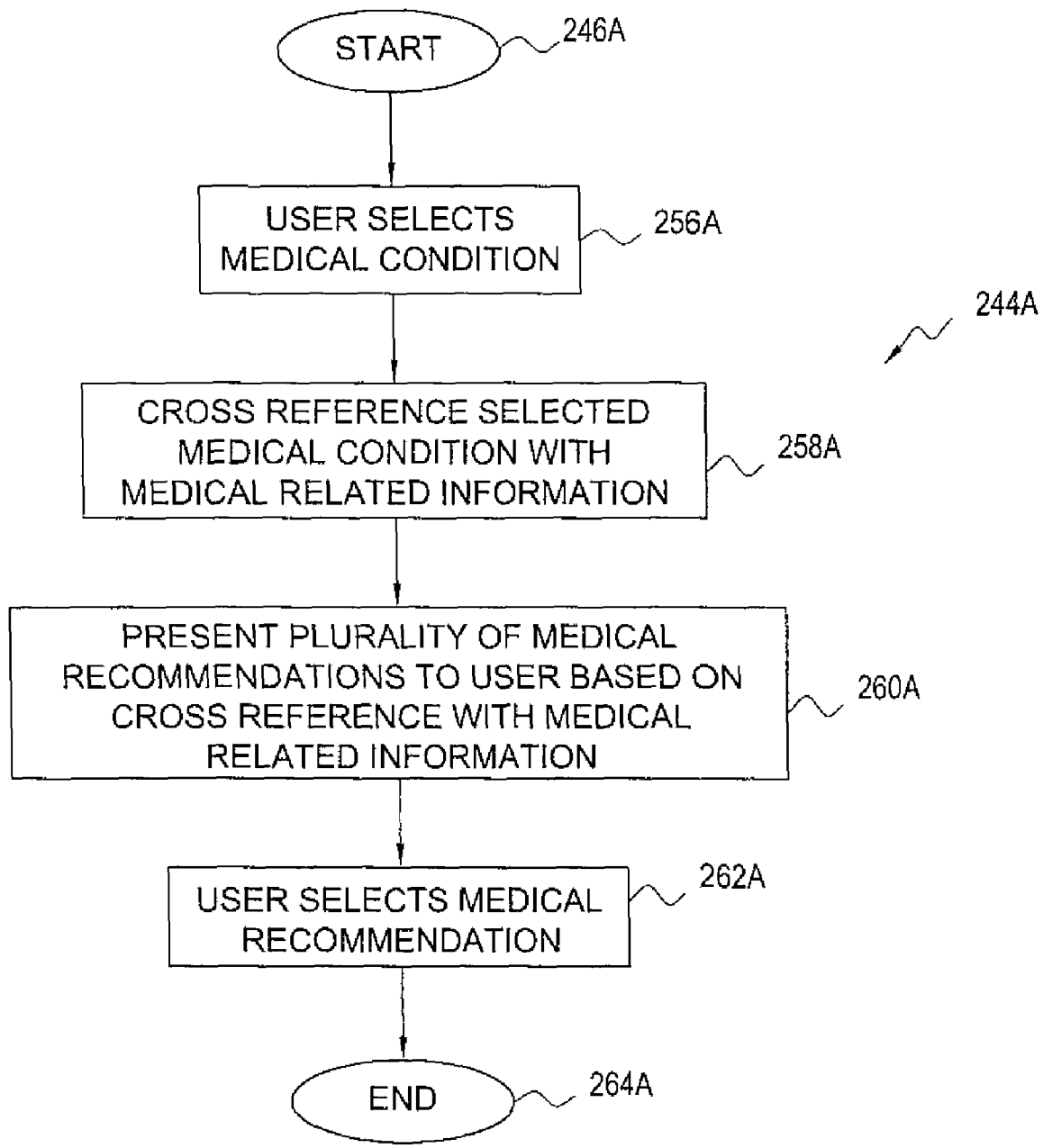

Referring now to the flowchart 244A of FIG. 18A, another method aspect of the present invention is now described in greater detail. The method aspect illustrated in the flowchart 244A of FIG. 18A is directed to using a medical decision system 102 to make a medical related decision. From the start (Block 246A), the user may select a medical condition at Block 256A. At Block 258A, the selected medical treatment may be cross-referenced with the medical related information in the medical related information databases 104.

After selecting a medical condition, the user may be presented with a plurality from the medical recommendations based on the comparison of the selected medical condition with the medical related information in the medical related information databases 104 at Block 260A. At Block 262A, the user may select one of the medical recommendations. The method is ended at Block 264A. Those skilled in the art will appreciate that the medical recommendations may be narrowed by applying a rule to the medial recommendations, as discussed in greater detail above.

Figure 19:
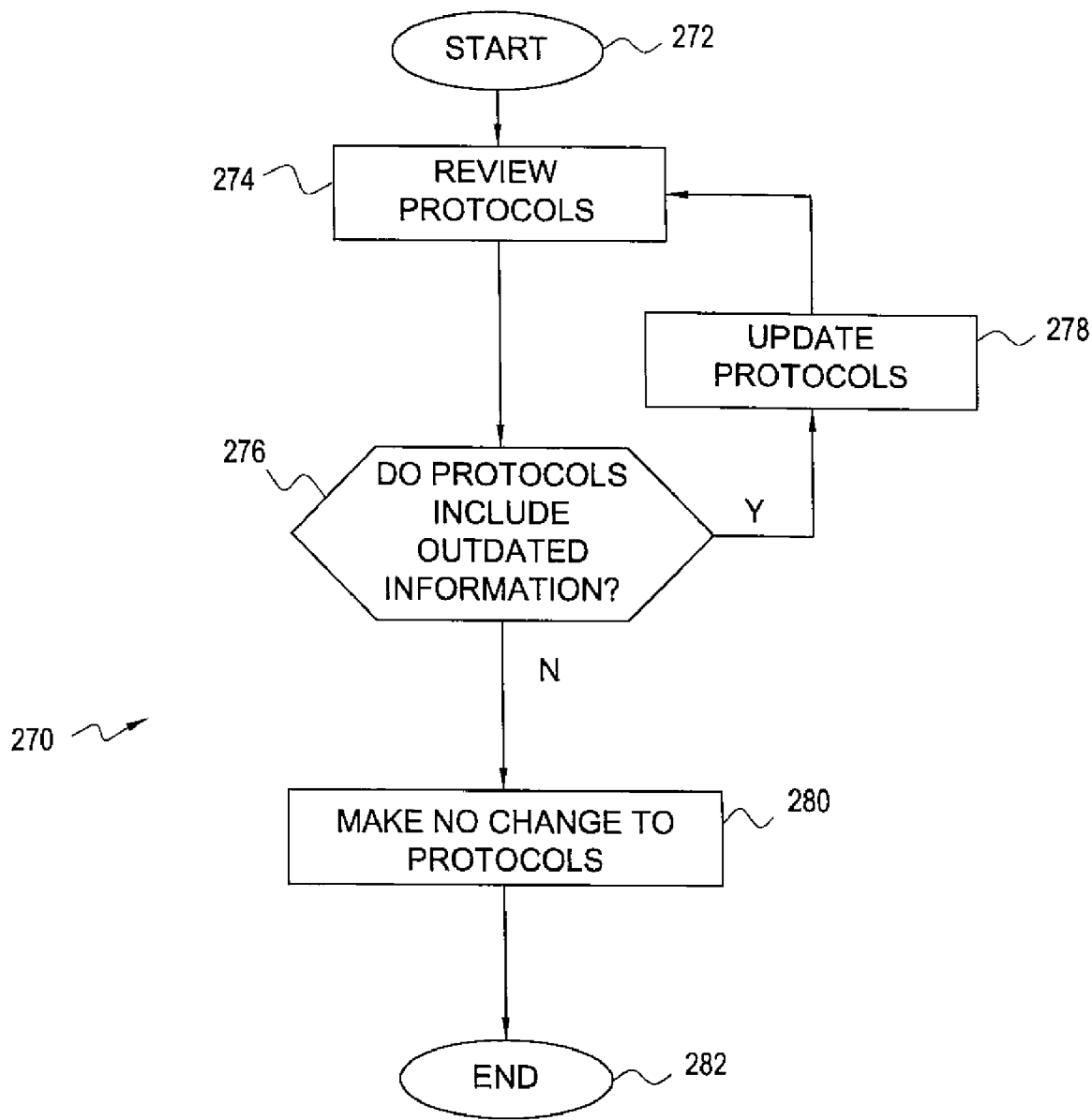

Referring now additionally to the flowchart 270 illustrated in FIG. 19, another method aspect of the present invention is now described in greater detail. More specifically, the method illustrated in the flowchart 270 of FIG. 19 is directed to reviewing and updating protocols when using the medical decision system 102 according to the present invention. From the start (Block 272), the protocols in the protocol database 126 are reviewed at Block 274. At Block 276, it is determined whether or not the protocols reviewed at Block 274 include outdated medical information. If it is determined at Block 276 that any of the protocols in the protocols database 126 include outdated medical information, then the protocols are updated at Block 278. Those skilled in the art will appreciate that the outdated medical information may be automatically updated. For example, if a new treatment is available for a particular medical condition, the protocols database 126 may be updated with the new treatment. When the protocols database 126 is updated with the information relating to the new treatment, the user may be presented with the information so that the user may update their protocols database 126. In some instances, each user's protocols database 126 may be automatically updated, but some user's may chose to review each update and select whether or not to update their database. Accordingly, the system according to the present invention may advantageously allow the user to customize and select which protocols to update. Thereafter, additional review of the protocols takes place at Block 274. If, however, it is determined that the protocols included in the protocols database 126 do not include outdated medical information, then no change is made to the protocols at Block 280. The method is ended at Block 282.

Figure 19A:
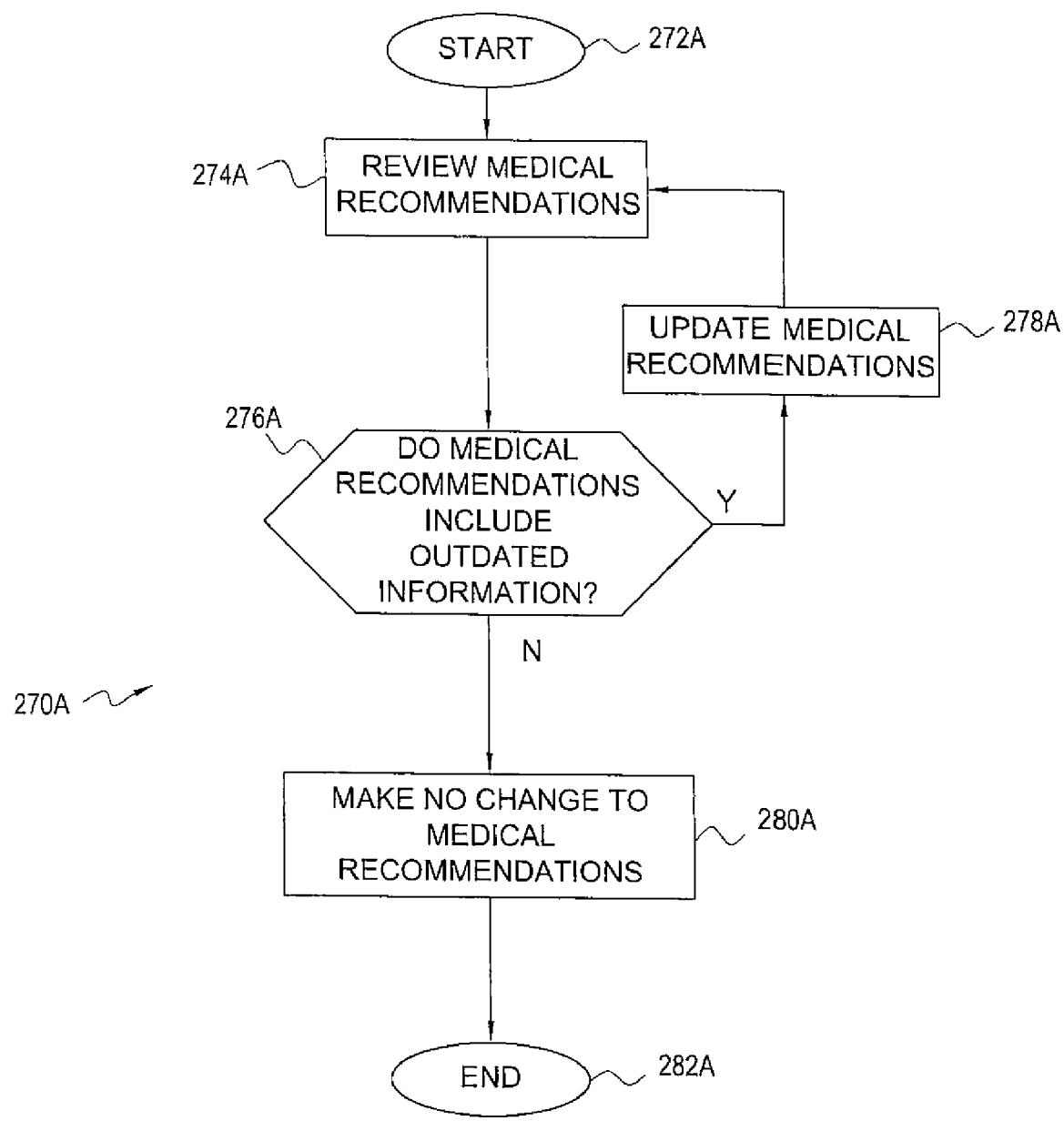

Referring now additionally to the flowchart 270A illustrated in FIG. 19A, another method aspect of the present invention is now described in greater detail. More specifically, the method illustrated in the flowchart 270A of FIG. 19A is directed to reviewing and updating medical recommendations when using the medical decision system 102 according to the present invention. From the start (Block 272A), the medical recommendations in the medical related information database are reviewed at Block 274A. At Block 276A, it is determined whether or not the medical recommendations reviewed at Block 274A include outdated medical information. If it is determined at Block 276A that any of the medical recommendations in the medical related information database include outdated medical information, then the medical recommendations are updated at Block 278A. Those skilled in the art will appreciate that the outdated medical recommendations may be automatically updated. For example, if a new medical recommendation is available for a particular medical condition, the medical related information database may be updated with the new medical recommendations. When the medical related information database is updated with the information relating to the new medical recommendations, the user may be presented with the information so that the user may update their medical related information database. In some instances, each user's medical related information database may be automatically updated, but some user's may chose to review each update and select whether or not to update their database. Accordingly, the system according to the present invention may advantageously allow the user to customize and select which medical recommendations to update. Thereafter, additional review of the medical recommendations takes place at Block 274A. If, however, it is determined that the medical recommendations included in the medical related information database do not include outdated medical information, then no change is made to the medical recommendations at Block 280A. The method is ended at Block 282A.

Figure 20:
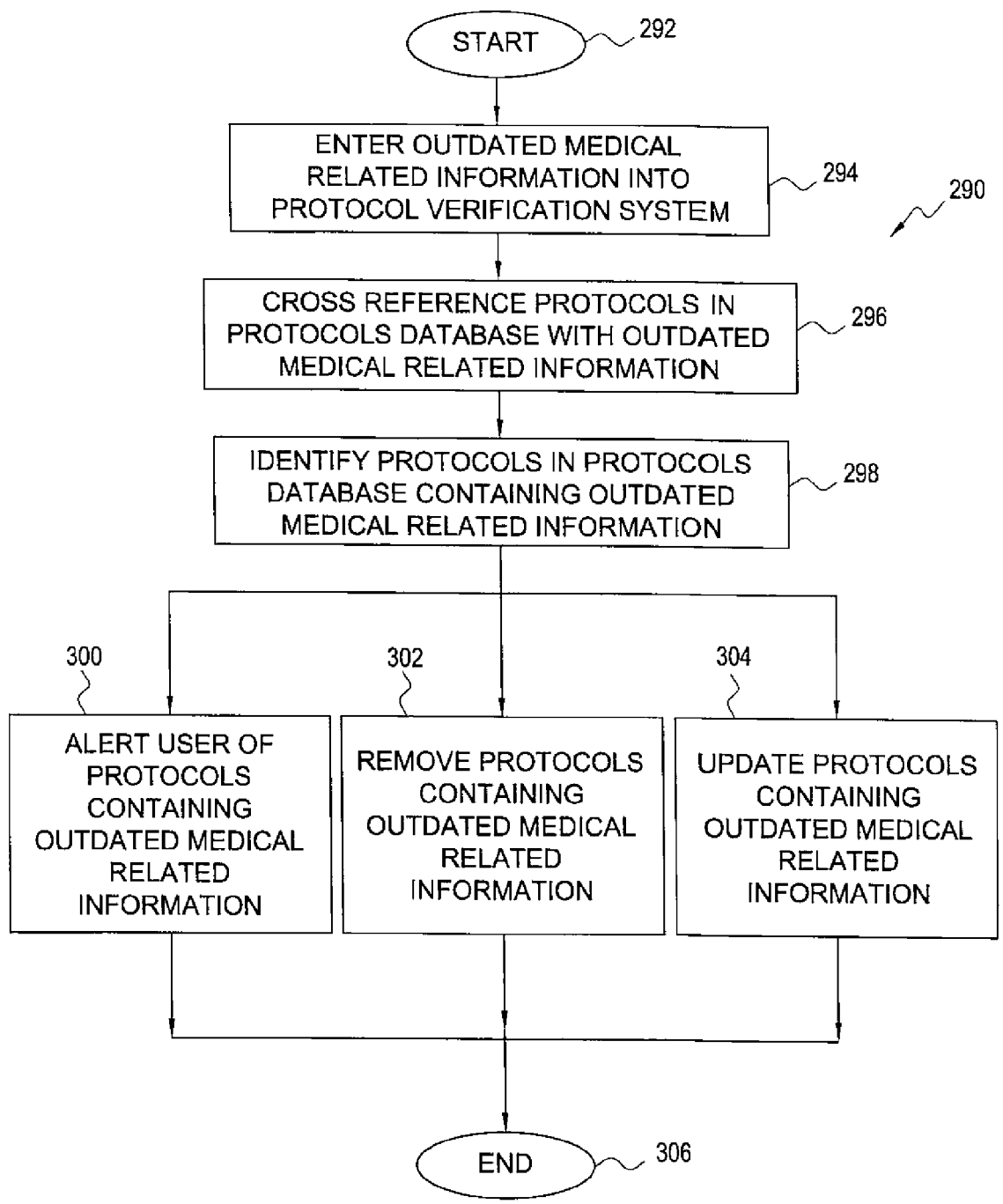

Referring now additionally to the flowchart 290 illustrated in FIG. 20, still another method aspect of the present invention is now described in greater detail. The method aspect of the invention illustrated in the flowchart 290 is directed to using a verification system of the medical decision system 102 to verify protocols. From the start (Block 292), outdated medical related information is entered into the protocol verification system at Block 294. At Block 296, the protocols stored on the protocols database 126 are cross-referenced with the outdated information entered at Block 294. At Block 298, protocols containing the outdated medical information entered at Block 294 are identified.

Upon identification of the protocols in the protocol's database 126 that may include the outdated medical related information entered at Block 294, any number of actions may illustratively occur. For example, an alert may be presented to the user at Block 300 indicating that a particular protocol stored on the protocols database 126 contains the outdated medical related information entered at Block 294. Alternately, the protocol that is identified as containing the outdated medical related information at Block 298 may automatically be removed from the protocols database 126 at Block 302. Yet another alternative is to automatically update the protocol identified as containing the outdated medical related information at Block 298 with updated medical related information at Block 304. Thereafter, the method is ended at Block 306.

Figure 20A:
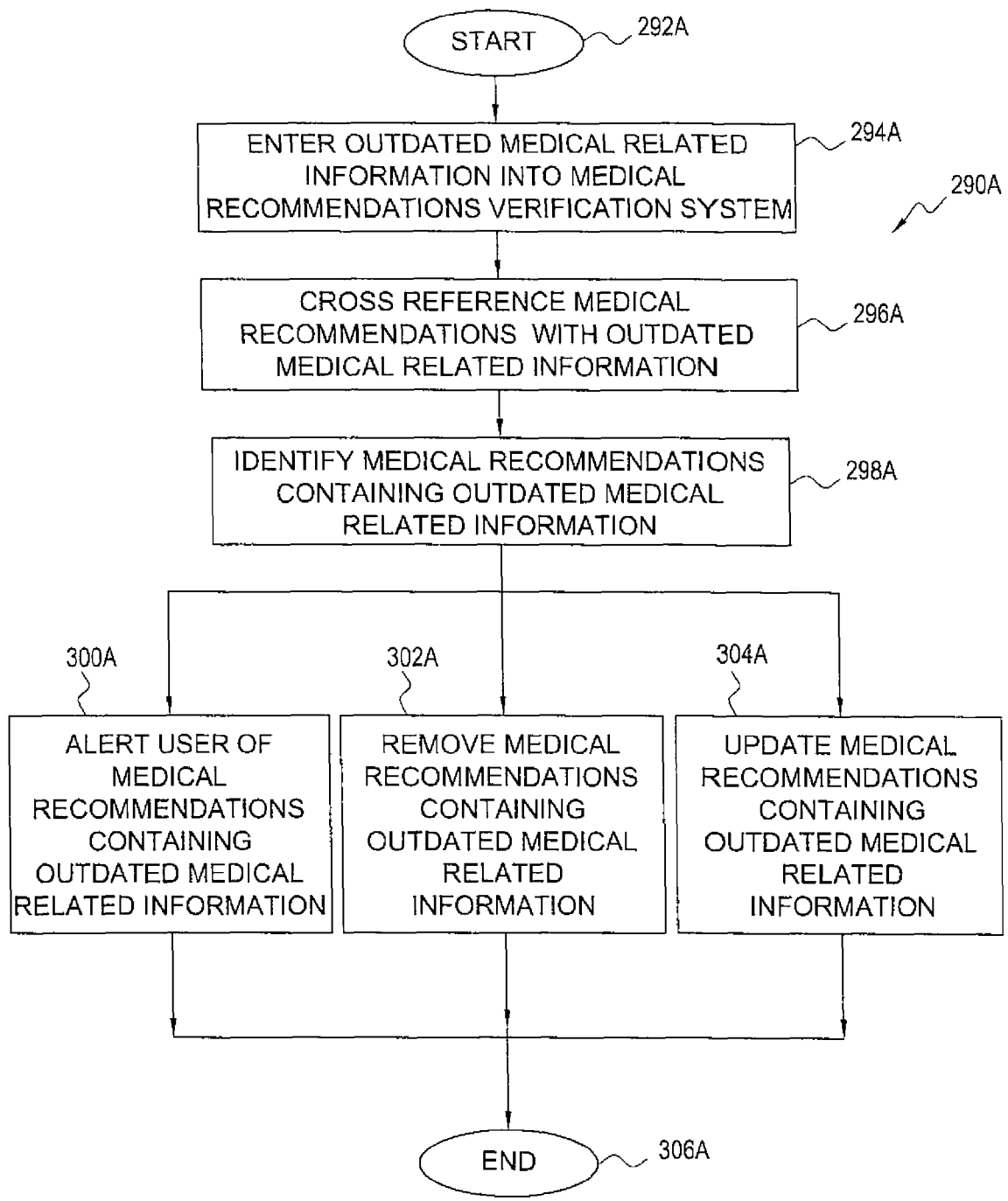

Referring now additionally to the flowchart 290A illustrated in FIG. 20A, still another method aspect of the present invention is now described in greater detail. The method aspect of the invention illustrated in the flowchart 290A is directed to using a verification system of the medical decision system 102 to verify medical recommendations. From the start (Block 292A), outdated medical related information is entered into the medical recommendations verification system at Block 294A. At Block 296A, the medical recommendations stored on the medical related information database 104 are cross-referenced with the outdated information entered at Block 294A. At Block 298A, medical recommendations containing the outdated medical information entered at Block 294A are identified.

Upon identification of the medical recommendations in the medical related information database 104 that may include the outdated medical related information entered at Block 294A, any number of actions may illustratively occur. For example, an alert may be presented to the user at Block 300A indicating that particular medical recommendations stored on the medical related information database 104 contains the outdated medical related information entered at Block 294A. Alternately, the medical recommendations that are identified as containing the outdated medical related information at Block 298A may automatically be removed from the medical related information database 104 at Block 302A. Yet another alternative is to automatically update the medical recommendations identified as containing the outdated medical related information at Block 298A with updated medical related information at Block 304A. Thereafter, the method is ended at Block 306A.

Figure 21:
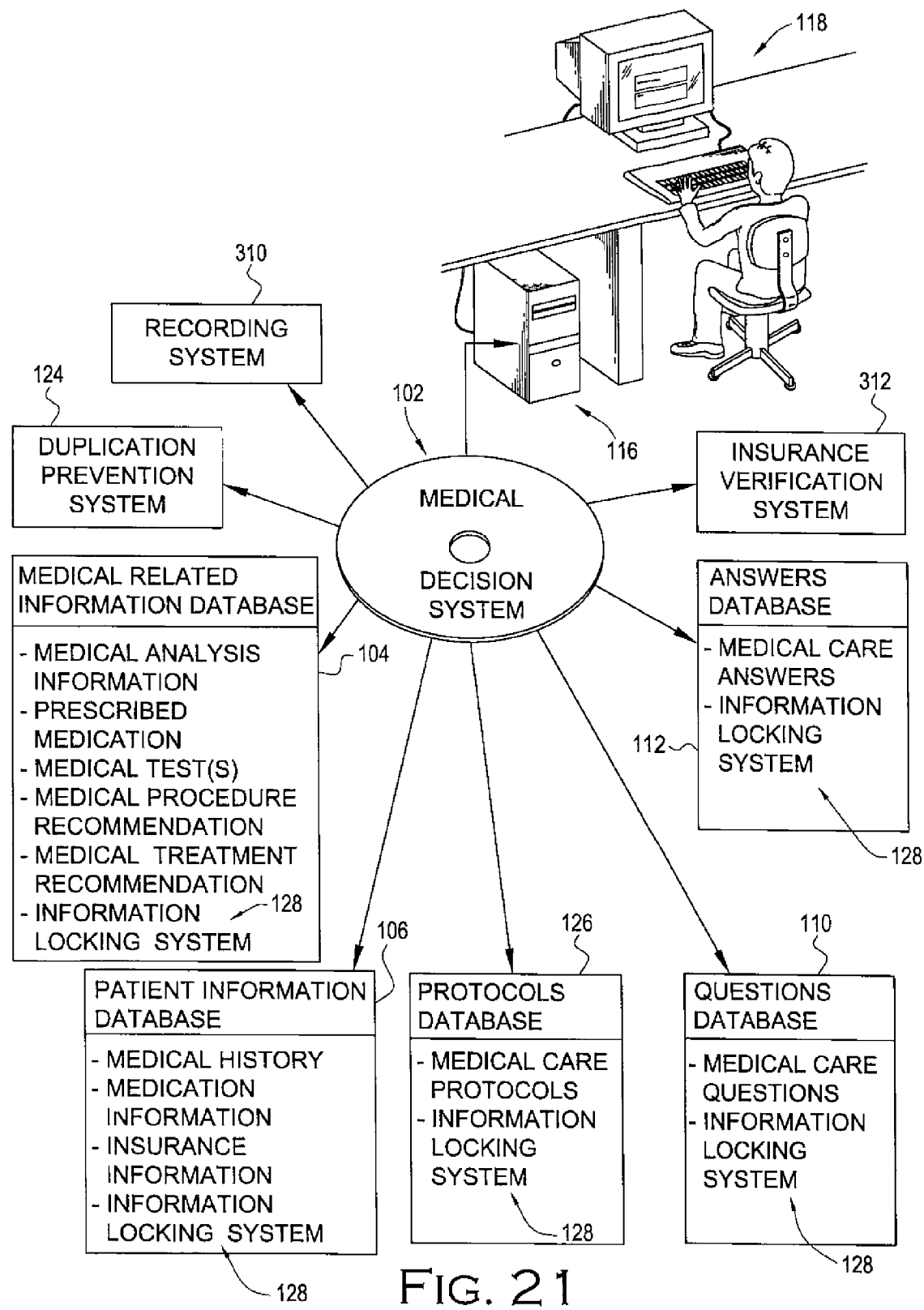
FIGS. 21-22 are schematic views of a medical decision system wherein databases are locked to reduce fraud.
Figure 22:
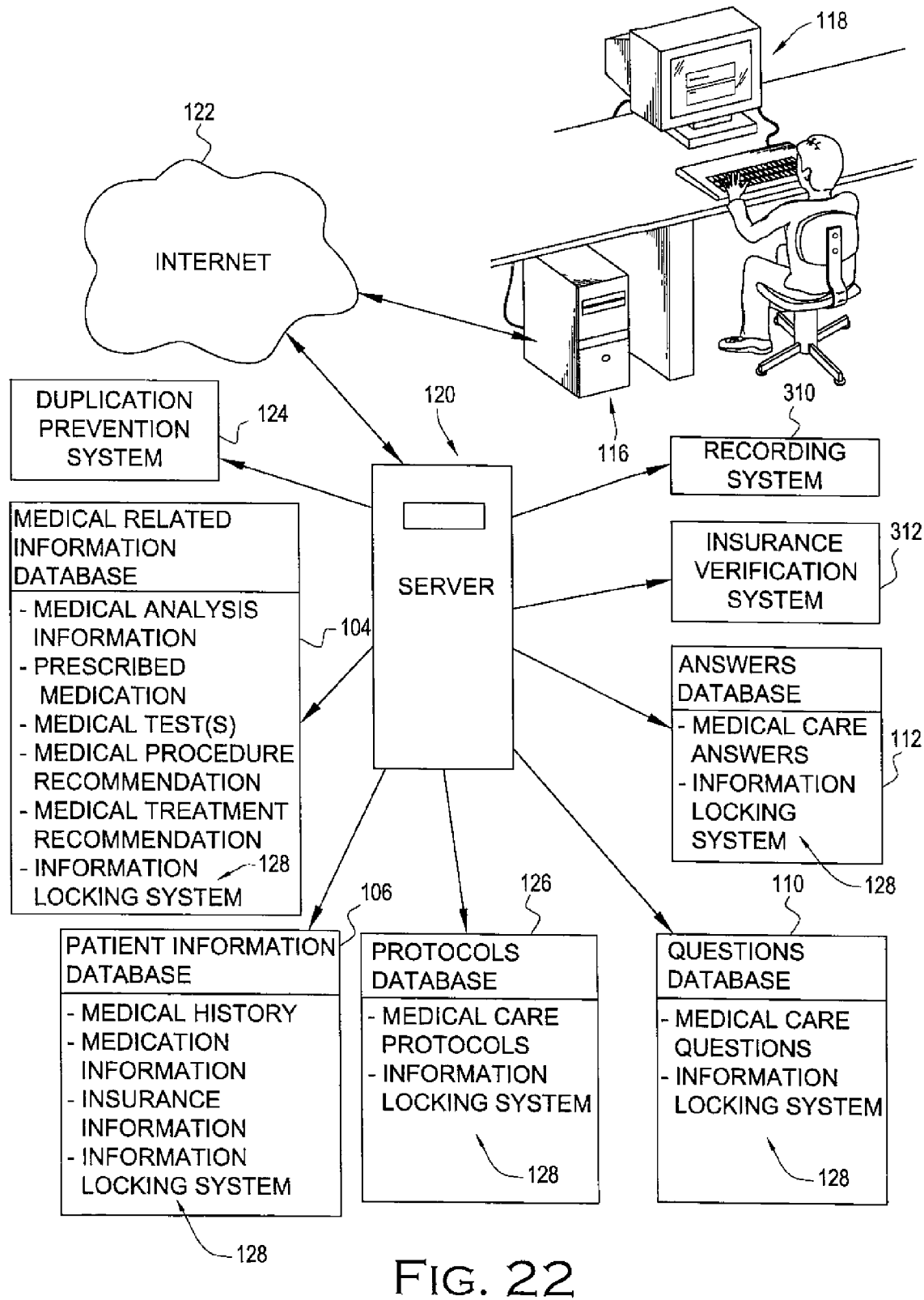

Referring now additionally to FIGS. 21-22, another feature of the medical decision system 102 according to the present invention is now described in greater detail. As illustrated in FIGS. 21-22, the medical decision system 102 may include information locking systems 128. The information locking systems 128 of the medical decision system 102 advantageously lock information in the plurality of databases to prevent alteration thereof, thereby reducing the risk of fraud.

More specifically, the questions database 110 may include a plurality of questions to be presented to a user relating to medical care. Each of the plurality of questions in the questions database 110 may have question text associated therewith and a predetermined question code associated with the question text. After having had the benefit of this disclosure, those skilled in the art will appreciate that various codes may be assigned to questions, or even concepts, in the questions database 110. In other words, codes may be assigned to any information that is stored in the questions database 110. The codes relate to the text of the questions, and are used in the processing of the information contained in the questions on the questions database 110. The answers database 112 includes a plurality of answers related to the plurality of questions in the questions database 110. The answers include answer text associated therewith and a predetermined answer code associated with the answer text. Similar to the question code and text, the predetermined answer code may be associated with the answer text to process the medical information contained in the answer text.

The plurality of medical related information databases 104 may include medical related information and rules governing medical care. The medical related information may be directed to a medical decision to be made by the user based on the answers to the questions. The plurality of medical related information databases 104 may be in communication with one another. The medical decision system 102 illustrated in FIG. 21 includes the answers database 112, the questions database 110, the protocols database 126, the patient information database 106, the medical related information databases 104, and a duplication prevention system 124 stored on a computer readable medium 114. The computer readable medium may be used on a computer 116 and may be accessed by a user using a user interface 118. The medical decision system 102 illustrated in FIG. 22 is preferably stored on a central computer, such as a server 120, and accessible by the user using a user interface 118 through a global communications network, i.e., the Internet 122.

The information locking system 128 advantageously locks any one of the question text, the answer text, the predetermined question code and the predetermined answer code to prevent alteration thereof. More specifically, the information locking system 128 advantageously prevents any alteration of the medical related information or any medical decision to thereby greatly reduce any chance of fraud.

After having had the benefit of reading this disclosure, those skilled in the art will appreciate that fraud may occur at a number of places during a number of different stages of using the medical decision system 102. For example, fraud may occur at a point of use of the medical decision system 102, or may occur after information is transmitted from the medical decision system to a processing center. The processing center may, for example, be an insurance processing center, a hospital administrator, a medical board, or any other place where medical information may be transmitted. Accordingly, it is preferable that the information locking system 128 locks the question text, the predetermined question code, the answer text, and/or the predetermined answer code at either the point of use of the medical decision system 102 or after the medical information has been transmitted to a processing center.

After having had the benefit of reading this disclosure, those skilled in the art will also appreciate that locking the answer text and predetermined answer code is applicable to answers that are stored on the answers database 112, and also applicable to answers that a user has entered, i.e., customized answers. Upon entering a customized answer a predetermined answer code may be assigned to the customized answer. The predetermined answer code assigned to the customized answer relates to the text of the customized answer. One way in which the customized answer text and the predetermined answer code may be locked is to automatically lock the customized answer text and the predetermined answer code after a predetermined amount of time has passed after the user has entered the customized answer. It is further possible to provide an indication that the answer text and the predetermined answer code have been entered or changed. The information locking system 128 may thereafter lock the indication so that the indication may not be removed in an effort to hide the fact that the answer text and/or the predetermined answer code have been altered.

After having had the benefit of reading this disclosure, those skilled in the art will further appreciate that a medical decision made by the user may include medical decision text associated therewith and a predetermined medical decision code associated with the medical decision text. The information locking system 128 may lock both the medical decision text and the predetermined medical decision code. These may be locked at the point of use, the processing center to which the medical decision text and the predetermined medical decision code are transmitted to, or both.

The present invention contemplates that the locking system 128 can be used if the questions and answers from the respective questions and answers databases are either used directly from the system of if the questions and answers are used to populate a customizable system. For example, a medical professional may wish to use information from the various databases of the medical decisions system 102 according to the present invention in conjunction with an existing system, i.e., use the information from the present invention to populate questions and answers on a customized form. In such a case, the question text, question code, answer text and answer code would all also be locked using the locking system 128 according to the present invention.

The medical decision system 102 may also include a recording system 310 to record medical observations made by the user. The recording system 310 may illustratively be in communication with the patient information database 106, the questions database 110, the answers database 112, and the plurality of medical related information databases 104. The medical observations made by the user and stored on the recording system 310 may include medical observation text associated therewith, as well as a predetermined medical observation code associated with the medical observation text. The medical observation may be transmitted from a point of use to a processing center. Accordingly, both the medical observation text and the predetermined medical observation code may be locked at the point of use, the processing center to which it is transmitted, or both. This advantageously prevents alteration of the medical observation text and code to advantageously reduce the chance of fraud by falsifying and/or changing the medical observation made by the user.

The medical decision system 102 also illustratively includes an insurance verification system 312 in communication with the patient information database 106, the questions database 110, the answers database 112 and the plurality of medical related information databases 104 to verify that the question text, the predetermined question code, the answer text, the predetermined answer code, the medical decision text, the predetermined medical decision code, the medical observation text and the predetermined medical observation code have not been altered. More particularly, the insurance verification system may be automated to automatically verify that none of the above texts or codes has been altered.

A method aspect of the present invention is for making a medical decision using a medical decision system 102. The method includes presenting the user with a question from the questions database 110 relating to medical care. The method also includes prompting the user for an answer relating to the question, and prompting the user to a select a medical condition from the plurality of medical conditions stored on one of the plurality of medical related information databases 104 based on one of the medical observations made by the user and a comparison of the rules governing medical care stored on one of the plurality of medical related information databases with the answers relating to the questions. The method may also include locking the question text, the predetermined question code, the answer text, the predetermined answer code, the medical observation text, the predetermined medical observation code, the medical decision text, and/or the predetermined medical decision code at the point of use, the processing center to which the information is transmitted, or both.

The information locking system 128 according to the present invention may ensure that the questions are locked when presented to the user. This is yet another level of security that prevents a user from altering either text or a code associated with a question to thereby minimize fraud and/or mistakes. Similarly, when the plurality of answers are presented to the user, the answer code and answer text are already locked to prevent a user from altering either the answer text or answer code. Again, this is another level of security that prevents a user from altering either the answer text or answer code to thereby minimize fraud and/or mistakes.

Figure 23:
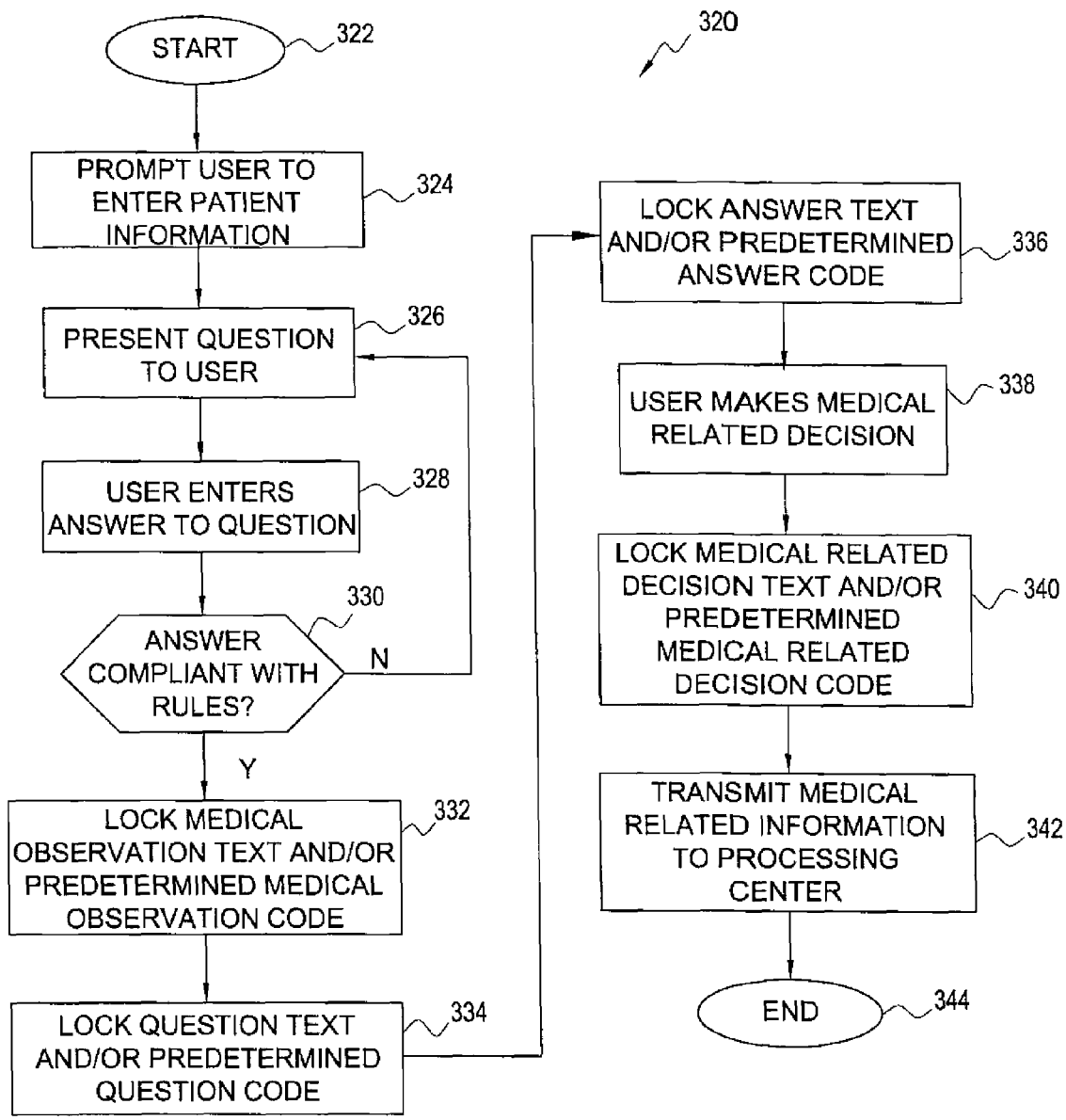
FIGS. 23-24 are flow charts illustrating methods of making a medical decision according to the present invention.

Referring now additionally to the flowchart 320 illustrated in FIG. 23, another method aspect of the present invention is now described in greater detail. More specifically, the method aspect of the invention illustrated in the flowchart 320 of FIG. 23 is directed to using an information locking system 128 in a medical decision system 102. From the start (Block 322) the user may enter patient information at Block 324. At Block 326, the user may be presented with a question from the questions database 110. At Block 328, the user may enter an answer to the question presented at Block 326. As discussed above, the answer may be selected from the answers database 112, or may be a customized answer entered by the user. At Block 330, it is determined whether or not the answer entered by the user at Block 328 is compliant with one of the rules stored on one of the medical related information databases 104.

If it is determined that the answer entered by the user at Block 328 is not in compliance with one of the rules stored on one of the medical related information databases 104, then the user is again prompted with the question at Block 326. If, however, it is determined at Block 330 that the answer entered by the user at Block 328 is compliant with one of the rules stored on one of the medical related information databases 104, then the medical observation text and/or predetermined medical observation code are locked at Block 332. Thereafter, at Block 334, the question text and/or predetermined question code are locked.

At Block 336, the answer text and/or predetermined answer code are locked, and at Block 338, the user may make a medical related decision based on the answers to the questions provided by the user. After the medical related decision is made at Block 338, the medical related decision text and/or predetermined medical related decision code may be locked at Block 340. Thereafter, at Block 342, the medical related information may be transmitted to a processing center. The method is ended at Block 344.

Figure 24:
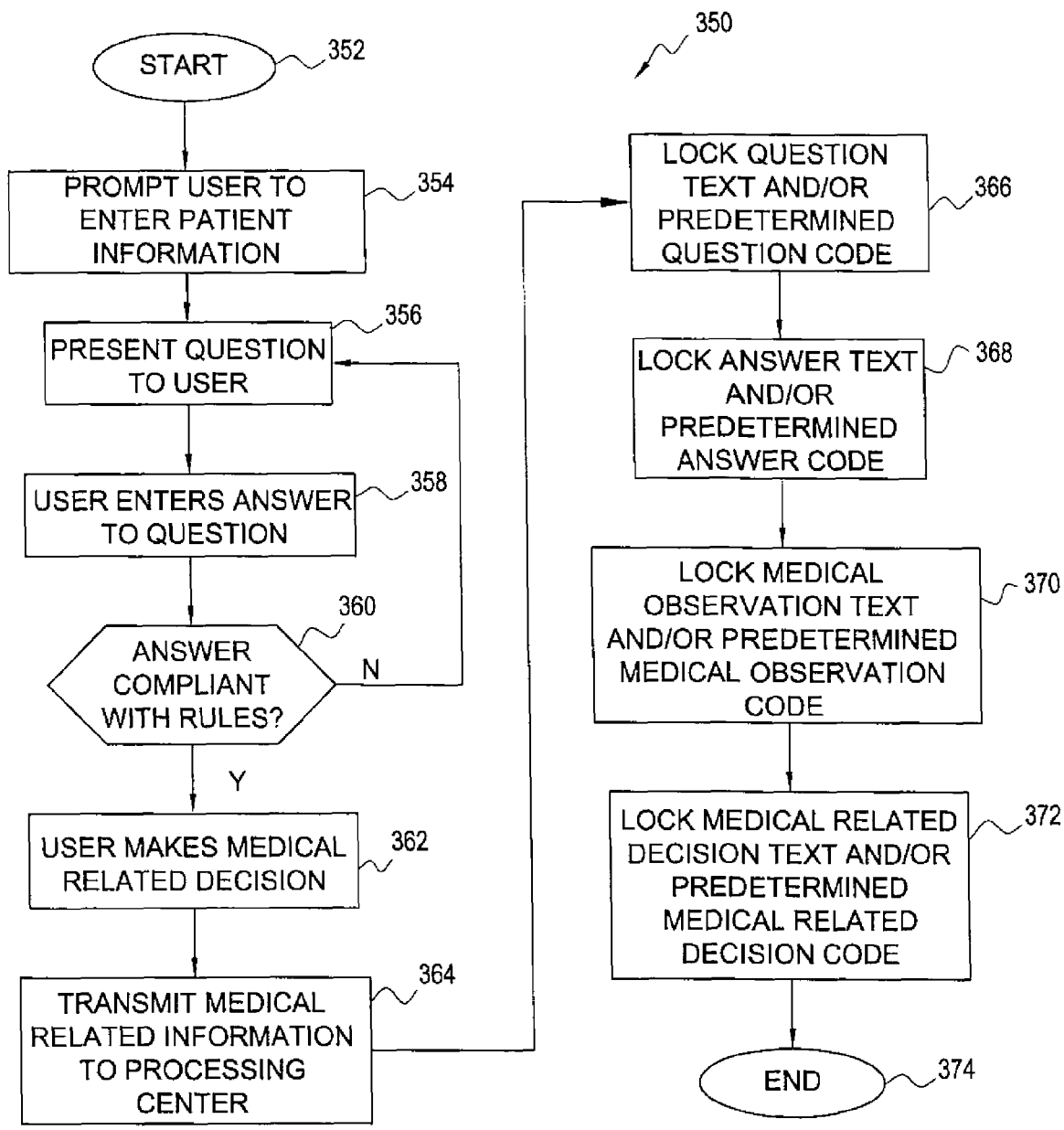

Referring now additionally to the flowchart 350 illustrated in FIG. 24, yet another method aspect of the present invention is now described in greater detail. The method aspect illustrated in the flowchart 350 illustrated in FIG. 24 is also directed to using an information locking system 128 of a medical decision system 102. From the start (Block 352), the user may enter patient information at Block 354. At Block 356, the user may be presented a question from the questions database 110. At Block 358, the user may enter an answer to the question presented at Block 356. As discussed above, the answer may be selected from the answers database 112, or may be a customized answer entered by the user. At Block 360 it is determined whether or not the answer entered by the user at Block 358 is compliant with one of the rules stored on the medical related information databases 104.

If it is determined at Block 360 that the answer entered by the user at Block 358 is not compliant with the rules stored on one of the medical related information databases 104, then the user is again prompted with the question at Block 356. If, however, it is determined at Block 360 that the answer entered by the user at Block 358 is compliant with one of the rules stored on one of the medical related information databases 104, then the user may make a medical related decision at Block 362. At Block 364, the medical related decision, and other medical related information, may be transmitted to a processing center. At Block 366, the question text and/or predetermined question code are locked after being transmitted to the processing center at Block 364. At Block 368, the answer text and/or predetermined answer code are locked, and at Block 370, the medical observation text and/or predetermined medical observation code are locked. At Block 372, the medical decision text and/or predetermined medical decision code are locked. Thereafter, the method is ended at Block 374.

With reference to the step of transmitting information to a processing center, it is to be understood that the present invention contemplates that transmitting may not necessarily all happen at one time. For example, a user may be using the system according to the present invention in an Internet setting, i.e., accessing an Internet site to enter information such as, for example, patient information, answers to the questions, medical decision selection, etc. In such a case, those skilled in the art will appreciate that information is being continuously transmitted. As such, it is to be understood that the information may be locked prior to transmission or after transmission, no matter when transmission occurs.

Those skilled in the art will appreciate that the system according to the present invention can be provided to a user in any language. Further, the system may advantageously allow for internal translation. This is especially advantageous in areas where a large amount of the population is bilingual. Internal translation may occur at any stage. More specifically, it is contemplated that, for example, the system may present a question to a user in a first predetermined language and the user may select to switch languages so that the question is presented in a second predetermined language. Thereafter, the answer may be selected or entered in any number of languages. This is especially helpful when more than one medical professional is using the system and some of the medical professionals speak different languages. For example, if two medical professionals are working with a patient that only speaks Spanish, and only one of the medical professionals speaks Spanish, the system can advantageously be used in Spanish so that the Spanish speaking one of the medical professionals can interact with the patient. Thereafter, the information being entered by the Spanish speaking one of the medical professionals may be instantly translated so that the second medical professional using the system can follow along, or can be translated at the end of the use so that the second medical professional can review the information entered into the system.

The present invention may also advantageously include a medical malpractice reduction system. Such a system allows a user to select a medical treatment based on compliance with the rules and present risks to a patient based on selected medical treatment. The system may require a patient to log in and indicate that the patient has understood the risks and agreed to the risks prior to undergoing the procedure. The system may also be used to calculate a probability of a poor outcome of a procedure based on several factors, i.e., patient's age, condition, or any other number of factors that may be used to calculate probabilities.

This calculated probability may be used for several different features of the system according to the present invention. For example, if the calculated probability exceeds a certain predetermined level, the user may be prevented from moving forward with a procedure, regardless of whether the patient wishes to move forward. Also for example, if a calculated probability exceeds a certain predetermined level, a patient may be prevented from indicating that they understand the risks and agreeing to the treatment for a certain amount of time, i.e., a cool off period. The present invention contemplates, however, that in some instances, such a cool off period may not be feasible and, as such, may include a feature that allows the user to perform a procedure regardless of the calculated risk percentage.

Any component of the present invention may be used as a stand alone system. Alternately, it is contemplated that each of the components of the present invention may be used together as a combination system. For example, finalization of a medical decision may stand alone, while displaying all medical treatments for a selected medical conditions may stand alone, as well as locking code and text may stand alone, and any of the several other features according to the system of the present invention may stand alone. This advantageously allows a user to customize their system depending on their needs. This also advantageously allows the system according to the present invention to be used in a wide range of facilities related to medical care, i.e., doctor's office, hospital, pharmacy, insurance company, etc.

The system according to the present invention also advantageously indicating to a user all contraindications, treatments, tests or procedures that may not be indicated for a specific diagnosis. As indicated above, each diagnosis, treatment and procedure may have various codes associated therewith. The system according to the present invention contemplates that these codes may be displayed for each diagnosis, treatment and procedure, and the codes may be insurance specific.

As discussed above, the system according to the present invention is a computer based system and, as such, requires a user interface to access the computer. Those skilled in the art will appreciate that the system may be accessed via a desktop computer, a laptop computer, a mobile communications device, a personal digital assistant, a handheld device, or any other type of device suitable for accessing and using the various components of the system. The method aspects of the present invention are preferably computer implemented methods. More particularly, all or some of the steps are preferably carried out using a computer.

The system according to the present invention may also advantageously include a medical fraud prevention system. The medical fraud prevention system can be used to prevent medical insurance fraud. The system may track the location of patients to make sure that a patient is within the vicinity of a medical professional or medical service provider that is reporting that medical services are being provided to the patient. The system can include a subscription service that tracks the patient's location using the patient's cell phone. The system can be provided by software that is downloadable onto a medical professional's system and that interacts with a central server, such as the insurance company servers, to track location of a patient.

The system can be a real time system that locates a patient at the instant when a medical decision is made by the medical professional to ensure that the patient is within the vicinity of the medical professional's location. The system can also be a non-real time system that monitors the location of a patient and checks if the patient was at the location of the medical professional office on the date, and possibly even around the time, when the medical service was rendered. The system can alert an insurance company of any discrepancies, and can be used to contact the patient to clear up discrepancies. If a patient does not wish to participate in the cell phone tracking feature, the patient may be provided with the possibility of allowing the insurance provider to call them on their cell phone to confirm that medical service was rendered. This call may, for example, be an automated call that allows the patient to confirm the rendering of medical service using a touchtone phone or by voice commands.

Many modifications and other embodiments of the invention will come to the mind of one skilled in the art having the benefit of the teachings presented in the foregoing descriptions and the associated drawings. Therefore, it is understood that the invention is not to be limited to the specific embodiments disclosed, and that modifications and embodiments are intended to be included within the scope of the appended claims.

That which is claimed is:

1. An interactive protocol system for a medical decision system comprising:
a plurality of medical related information databases including medical related information and rules required for a user to make a medical related decision;
a patient information database including patient information;
a medical practices database including information relating to medical practices;
a questions database including questions to be presented to a user relating to medical care; and
an answers database including answers related to the respective questions in said questions database, wherein the user provides at least one of an answer included within the answers database and a customized answer, wherein the customized answer includes the medical related information presented by the user related to the respective question in the questions database, and wherein the answers are compared to the rules contained within the plurality of medical related information databases;
wherein the plurality of medical related information databases, said patient information database, said medical practices database, said questions database and said answers database are stored on at least one of a computer readable medium and a computer memory, and are accessible by a user using a user interface;
wherein the medical practices database includes a plurality of protocols, and wherein each of the plurality of protocols includes a different plurality of narrowing questions to be presented to the user, and wherein the questions relating to at least one of the plurality of protocols are presented to the user based on the answers to the questions provided by the user, and wherein the narrowing questions in at least one of the plurality of protocols are to be answered by the user to provide the user an indication relating to medical practices;
wherein the answers inputted by the user using the user interface to the questions that are not in compliance with the rules generates an error message and prompts re-presentation of the questions using the user interface, wherein the error message is presented to the user using the user interface and indicates noncompliance of the answers to the questions with the rules, wherein presentation of the error message by the system to the user using the user interface prevents the user from entering information necessary to make the medical related decision, wherein entry of an answer in response to the question that is in compliance with the rules is required for presentation of another narrowing question, and wherein the answer that prompts presentation of questions relating to one of the plurality of protocols is in compliance with the rules prior to presentation of the protocol;
wherein the answers to the questions are compared to the rules using a processor that executes instructions to make a determination of whether the answers entered by the user using the user interface are in compliance with the rules and to determine whether or not to present the error message to the user on the user interface; and
wherein the user is presented with an option using the user interface to enable the user to enter the information necessary to make the medical related decision upon entering a predetermined number of answers that relates to the number of additional narrowing questions presented to the user on the user interface.

2. An interactive protocol system according to claim 1 wherein the rules are at least one of insurance reimbursement rules, medical practice rules, medical diagnosis rules, medical procedures rules, medication rules, testing rules and medical therapy rules.

3. An interactive protocol system according to claim 1 wherein the indication relating to medical practices is at least one of a diagnosis, a medical related recommendation, a medical procedure, a medication to be prescribed, a series of medical related procedures, a medical test, and an indication relating to insurance reimbursement.

4. An interactive protocol system according to claim 1 wherein the plurality of medical related information databases includes medical analysis information used to make a medical related decision; wherein the medical related decision includes at least one of a prescribed medication, a medical test, a medical procedure recommendation, and a medical treatment recommendation; and wherein the indication relating to medical practices provides the user information necessary to make the medical related decision.

5. An interactive protocol system according to claim 1 wherein the indication relating to medical practices is a medical related decision selected from a plurality of medical related decisions stored on at least one of the plurality of medical related information databases; and further comprising a selectable override command to be selected by the user to allow the user to override the error message and make the medical related decision, the override command requiring entry of a reason for selection thereof by the user.

6. An interactive protocol system according to claim 5 wherein the medical related decision is based on a comparison of the rules stored on at least one of the plurality of medical related information databases with the answers to the questions.

7. An interactive protocol system according to claim 5 wherein the selected medical related decision represents one of a plurality of best practices; and
  wherein a best practice is defined as a best available medical related decision as determined by at least one medical professional peer and as updated on the plurality of medical related information databases.

8. An interactive protocol system according to claim 7 wherein the plurality of medical related information databases are automatically updated with the best practices.

9. An interactive protocol system according to claim 1 wherein the user enters patient information into the patient information database responsive to a prompted indication using said at least one user interface.

10. An interactive protocol system according to claim 9 further comprising a duplication prevention system to prevent presentation of a prompted indication requiring entry of patient information that is currently stored in the patient information database.

11. An interactive protocol system according to claim 9 wherein information entered by the user using said at least one user interface includes at least one of medical history information, medication information and insurance information; and wherein the information entered by the user is entered into at least one of the plurality of medical related information databases and the patient information database.

12. A method of making a medical related decision using an interactive protocol system including a plurality of medical related information databases including medical related information and rules required for a user to make a medical related decision, and a medical practices database including a plurality of protocols, the plurality of medical related information databases being stored on at least one of a computer readable medium and a computer memory and accessible by a user using a user interface, the method comprising:
  presenting the user with at least one question relating to medical care stored on a questions database;
  prompting the user for an answer relating to the at least one question;
  determining at least one of the plurality of protocols to be presented to the user based on the answers to the questions;
  presenting the user with additional narrowing questions relating to the at least one protocol from the questions database to be answered;
  providing the user an indication relating to medical practices based on the respective answers to the narrowing questions; and
  wherein the answers to the questions include at least one of an answer included within the answers database and a customized answer, and wherein the customized answer includes the medical related information presented by the user related to the respective question in the questions database;
  wherein the answers inputted by the user using the user interface to the questions that are not in compliance with the rules generate an error message, and prompts re-presentation of the question using the user interface, wherein the error message is presented to the user using the user interface and indicates noncompliance of the answers to the questions with the rules, and wherein presentation of the error message by the system to the user using the user interface prevents the user from entering information necessary to make the medical related decision;
  wherein entry of an answer in response to the at least one question that is in compliance with the rules is required for determining at least one of the plurality of protocols to be presented to the user;
  wherein entry of an answer in response to the at least one question that is in compliance with the rules is required for presenting the user with additional narrowing questions;
  wherein entry of an answer that prompts presentation of additional narrowing questions relating to one of the plurality of protocols that is in compliance with the rules is required prior to presentation of the protocol;
  wherein the answers to the questions are compared to the rules using processor that executes instructions to make a determination of whether the answers entered by the user using the user interface are in compliance with the rules and to determine whether or not to present the error message to the user on the user interface; and
  wherein entry of answers relating to the additional narrowing questions that are in compliance with the rules is required prior to the user being enabled to enter the information necessary make the medical related decision using the user interface.

13. A method according to claim 12 wherein the rules are at least one of insurance reimbursement rules, medical practice rules, medical diagnosis rules, medical procedures rules, medication rules, testing rules and medical therapy rules.

14. A method according to claim 12 wherein providing the indication further comprises providing at least one of a diagnosis, a medical related recommendation, a medical procedure, a medication to be prescribed, a series of medical related procedures, a medical test stored on one of the plurality of medical related information databases and an indication relating to insurance reimbursement.

15. A method according to claim 12 wherein the plurality of medical related information databases includes medical analysis information used to make the medical related decision; wherein the medical related decision includes at least one of a prescribed medication, a medical test, a medical procedure recommendation, and a medical treatment recommendation; and wherein the indication relating to medical practices provides the user information necessary to make the medical related decision.

16. A method according to claim 12 wherein the indication relating to medical practices is a medical related decision selected from a plurality of medical related decisions stored on at least one of the plurality of medical related information databases; and further comprising allowing the user to override the error message and resume making the medical related decision, and requiring entry of a reason for entering the override of the error message by the user.

17. A method according to claim 16 wherein the medical related decision is based on a comparison of the rules stored on at least one of the plurality of medical related information databases with the answers in the answers to the questions.

18. A method according to claim 16 wherein the selected medical related decision represents one of a plurality of best practices; and wherein a best practice is defined as a best available medical related decision as determined by at least one medical professional peer; and further comprising updating the best practices on the plurality of medical related information databases.

19. A method according to claim 12 further comprising using the at least one user interface to enter patient information into a patient information database responsive to a prompted indication.

20. A method according to claim 19 further comprising preventing presentation of a prompted indication requiring entry of patient information that is currently stored in the patient information database.

21. A method according to claim 19 wherein information entered by the user using the at least one user interface includes at least one of medical history information, medication information and insurance information; and wherein the information entered by the user is entered into at least one of the plurality of medical related information databases and the patient information database.

22. A method of making a medical related decision using an interactive protocol system including a plurality of medical related information databases including medical related information and rules required for a user to make a medical related decision, and a medical practices database including a plurality of protocols, the plurality of medical related information databases being stored on at least one of a computer readable medium and a computer memory and accessible by a user using a user interface, the method comprising:
    presenting the user with at least one question relating to medical care stored on a questions database;
    prompting the user for an answer relating to the at least one question;
    determining at least one of the plurality of protocols to be presented to the user based on the answers to the questions;
    presenting the user with additional narrowing questions relating to the at least one protocol from the questions database to be answered;
    entering patient information into a patient information database using the at least one user interface responsive to a prompted indication; and
    preventing presentation of a prompted indication requiring entry of patient information that is currently stored in the patient information database;
    wherein the answers to the questions include at least one of an answer included within the answers database and a customized answer, and wherein the customized answer includes the medical related information presented by the user related to the respective question in the questions database; and
    wherein the answers inputted by the user using the user interface to the questions that are not in compliance with the rules generate an error message and prompts re-presentation of the questions using the user interface, wherein the error message is presented to the user using the user interface and indicates noncompliance of the answers to the questions with the rules, and wherein the presentation of the error message by the system to the user using the user interface prevents the user from entering information necessary to make the medical related decision;
    wherein entry of an answer in response to the at least one question that is in compliance with the rules is required for determining one of the plurality of protocols to be presented to the user;
    wherein entry of an answer in response to the at least one question that is in compliance with the rules is required for presenting the user with additional narrowing questions;
    wherein entry of an answer that prompts presentation of additional narrowing questions relating to one of the plurality of protocols that is in compliance with the rules is required prior to presentation of the protocol;
    wherein the answers to the questions are compared to the rules using a processor that executes instructions to make a determination of whether the answers entered by the user using the user interface are in compliance with the rules and to determine whether or not to present the error message to the user on the user interface; and
    wherein entry of answers relating to the additional narrowing questions that are in compliance with the rules is required prior to the user being enabled to enter the information necessary to make the medical related decision using the user interface.

23. A method according to claim 22 wherein the rules are at least one of insurance reimbursement rules, medical practice rules, medical diagnosis rules, medical procedures rules, medication rules, testing rules and medical therapy rules.

24. A method according to claim 22 further comprising providing the user an indication relating to medical practices based on the respective answers to the narrowing questions of the selected medical related decision; and further comprising allowing the user to override the error message and resume making the medical related decision, and requiring entry of a reason for entering the override of the error message by the user.

25. A method according to claim 24 wherein providing the indication further comprises providing at least one of a diagnosis, a medical related recommendation, a medical procedure, a medication to be prescribed, a series of medical related procedures, a medical test stored on one of the plurality of medical related information databases, and an indication relating to insurance reimbursement.

26. A method according to claim 24 wherein the plurality of medical related information databases includes medical analysis information used to make the medical related decision; wherein the medical related decision includes at least one of a prescribed medication, a medical test, a medical procedure recommendation, and a medical treatment recommendation; and wherein the indication relating to medical practices provides the user information necessary to make the medical related decision.

27. A method according to claim 26 wherein the selected medical related decision represents one of a plurality of best practices; and wherein a best practice is defined as a best available medical related decision as determined by at least one medical professional peer; and further comprising updating the best practices on the plurality of medical related information databases.

28. A method according to claim 26 wherein the selected medical related decision is based on a comparison of the rules stored on at least one of the plurality of medical related information databases with the answers to the questions.

29. A method according to claim 22 wherein information entered by the user using the at least one user interface includes at least one of medical history information, medication information and insurance information; and wherein the information entered by the user is entered into at least one of the plurality of medical related information databases and the patient information database.

* * * * *